US007135171B2

(12) United States Patent
Edelberg et al.

(10) Patent No.: US 7,135,171 B2
(45) Date of Patent: Nov. 14, 2006

(54) ENDOTHELIAL PRECURSOR CELLS FOR ENHANCING AND RESTORING VASCULAR FUNCTION

(75) Inventors: Jay Edelberg, New York, NY (US); Shahin Rafii, Great Neck, NY (US); Mun Hong, New York, NY (US); Robert P. Lanza, Clinton, MA (US); Michael D. West, Southborough, MA (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/367,639

(22) Filed: Feb. 13, 2003

(65) Prior Publication Data

US 2004/0001807 A1    Jan. 1, 2004

Related U.S. Application Data

(63) Continuation-in-part of application No. 10/215,271, filed on Aug. 8, 2002.

(60) Provisional application No. 60/357,328, filed on Feb. 15, 2002, provisional application No. 60/311,238, filed on Aug. 9, 2001.

(51) Int. Cl.
*A01N 63/00* (2006.01)
*A61K 48/00* (2006.01)
*A01N 43/04* (2006.01)
*C12P 21/06* (2006.01)
*C12N 5/00* (2006.01)
*C12N 16/63* (2006.01)

(52) U.S. Cl. .............. 424/93.1; 424/93.2; 424/93.21; 424/93.7; 514/44; 435/69.1; 435/325; 435/455

(58) Field of Classification Search .............. 435/69.1, 435/320.1, 325, 455; 536/23.1, 23.5; 514/44; 424/93.1, 93.2, 93.21

See application file for complete search history.

(56) References Cited

U.S. PATENT DOCUMENTS

| | | | | |
|---|---|---|---|---|
| 5,955,436 | A | 9/1999 | Kunkle, Jr. | 514/21 |
| 5,980,887 | A * | 11/1999 | Isner et al. | 424/93.7 |
| 6,077,987 | A | 6/2000 | Breitbart et al. | 623/11 |
| 6,086,866 | A | 7/2000 | Kouri | 424/85.1 |
| 6,235,713 | B1 | 5/2001 | Achen et al. | 514/12 |
| 6,350,731 | B1 | 2/2002 | Jehanli et al. | 514/12 |
| 6,398,816 | B1 | 6/2002 | Breitbart et al. | 623/23.72 |
| 2002/0197232 | A1 | 12/2002 | Snodgrass et al. | |

OTHER PUBLICATIONS

Itescu et al J. Mol. Med. 81;288-296, 2003.*
Rafii et al Nat. Med 9(6):702-712, 2003.*
Xaymaran et al Circ. Res. 94:e39-e45, 2004.*
Chiu RC. Expert Opin Biol Ther. 3(2):215-25 2003.*
Juengst BMJ, 326 :1410-11, 2003.*
Brown et al Blood 100(4) :1133-1140, 2002.*
Rosenberg et al, Science 287:1751, 2000.*
Touchette, Nat. Med. 2(1) 7-8, 1996.*
Edelberg et al, Young adult bone marrow-derived endothelial precursor cells restore aging-impaired cardiac angiogenic function. Circ Res. 90(10): E89-93. 2002.*
Ataliotis, P., et al., "Distribution and Function of Platelet-Derived Gowth Factos and Their Receptors during Embryogenesis", *International Review of Cytology*, 172, (1997), pp. 95-127.
Betsholtz, C., "Role of platelet-derived growth factors in mouse development", *Int. J. Dev. Biol.*, 39, (1995), pp. 817-825.
Christini, D., et al., "Direct biologically based biosensing of dynamic physiological function", *Am. J. Physiol. Heart Circ. Physiol.*, 280, (2001), pp. H2006-H2010.
Davis, T., et al., "Ex Vivo Expansion of Primitive Murine Hematopoietic Progenitor Cells on Procine Endothelial Cells", *Transplantation Proceedings*, 29, (1997), p. 2005.
Deuel, T., et al., "Human Platelet-derived Growth Factor", *The Journal of Biological Chemistry*, 256(17), (1981), pp. 8896-8899.
Edelberg, J., et al., "Enhanced myocyte-based biosensing of the blood-borne signals regulating chronotropy", *The Journal of Applied Physiology*, 92, (2002), pp. 581-585.
Edelberg, J. et al., "PDGF Mediates Cardiac Microvascular Communication", *Journal of Clinical Investigation*, 102(4), (1998), pp. 837-843.
Edelberg, J., et al., "Young Adult Bone Marrow-Derived Endothelilial Precursor Cells Restore Aging-Impaired Cardiac Angiogenic Function", *Circulation Research*, 90, (2002), pp. e89-e93.
Edleberg, J., et al., "Platelet-Derived Growth Facto-AB Limits the Extent of Myocardial Infarction in a Rat Model", *Circulation*, 105, (2002) pp. 608-613.
Hakuno, D., et al., "Bone Marrow-Derived Regenerated Cardiomyocytes (CMG Cells) Express Functional Adrenergic and Muscarinic Receptors", *Circulation*, 105, http://www.circulationaha.org,(2002), pp. 380-386.
Heldin, C., et al., "Chemical and Biological Properties of a Growth Factor From Human -Cultured Osteosarcoma Cells: Resemblance with Platelet-Derived Growth Factor", *Journal of Cellular Physiology*, 105, (1980), pp. 235-246.
Jackson, K., et al., "Regeneration of ischemic cardiac muscle and vascular endothelium by adult stem cells", *The Journal of Clinical Investigation*, 107(11), (2001), pp. 1395-1402.

(Continued)

*Primary Examiner*—Sumesh Kaushal
(74) *Attorney, Agent, or Firm*—Schwegman, Lundberg, Woessner & Kluth, P.A.

(57) ABSTRACT

The invention provides methods of treating and preventing loss of tissue vascularization that can occur, for example, upon aging.

2 Claims, 10 Drawing Sheets

OTHER PUBLICATIONS

Makino, S., et al., "Cardiomyocytes can be generated from marrow stromal cells in vitro", *The Journal of Clinical Investigation*, 103(5), (1999), pp. 697-705.

Malouf, N., et al., "Adult-Derived Stem Cells from the Liver Become Myocytes in the Heart in Vivo", *American Journal of Pathology*, 158(6), (2001), pp. 1929-1935.

Mohle, R., et al., "Expression of interleukin-5 by human bome marrow microvascular endothelial cells: implications for the regulation of eosinophilopoiesis in vivo", *British Journal of Haematology*, 99, (1997), pp. 732-738.

Orlic, D., et al., "Bone marrow cells regenerate infarcted myocardium", *Nature*, 410, (2001), pp. 701-705.

Palmer, T., et al., "Vascular Niche for Adult Hippocampal Neurogenesis", *The Journal of Comparative Neurology*, 425, (2000), pp. 479-494.

Rafii, S., et al., "Human Bone Marrow Microvascular Endothelial Cells Support Long-Term Proliferation and Differentiation of Myeloid and Megakaryocytic Porgenitors", *Blood*, 86(9), (1995), pp. 3353-3363.

Rafii, S., et al., "Regulation of Hematopoiesis by Microvascular Endothelium", *Leuk. Lymphoma*, 27, (1997), pp. 375-386.

Raines, E., et al., "Platelet-derived Growth Factor", *The Journal of Biological Chemistry*, 257(9), (1982), pp. 5154-5160.

Wang, T., et al., "Differential expression of nitric oxide synthases in EGF-responsive mouse neural precursor cells", *Cell Tissue*, 296, (1999), pp. 489-497.

Weinsaft, J., et al., "Aging-Associated Changes in Vascular Activity: A Potential Link To Geriatric Cardiovascular Disease", *The American Journal of Geriatric Cardiology*, 10(6), (2001), pp. 348-354.

Yourey, P., et al., "Vascular Endothial Cell Growth Factors Promote the In Vitro Development of Rat Photoreceptor Cells", *The Journal of Neuroscience*, 20(18), (2000), pp. 6781-6788.

Gill, Muhammad, et al., "Vascular Trauma Induces Rapid but Transient Mobilization of VEGFR2+ AC133+ Endothelial Precursor Cells.", *Circulation Research*, 88, (2001), 167-174.

Caplice, N. M., et al., "Growth Factors Released Into the Coronary Circulation After Vascular Injury Promote Proliferation of Human Vascular Smooth Muscle Cells in Culture", *J. Am Coll Cardiol*, 29 (7), American College of Cardiology. Published by Elsevier Science Inc.,(1997), 1536-1541.

D'Ippolito, G., et al., "Age-Related Osteogenic Potential of Mesenchymal Stromal Stem Cells from Human Vertebral Bone Marrow", *Journal of Bone and Mineral Research*, 14 (7), (1999), 1115-1122.

Edelberg, J. M., et al., "Restoration of Senescent Cardiac Angiogenic Activity", *Circulation*, 104 (17) Supplement, XP008049055, (Oct. 23, 2001),II.0.

Edelberg, J. M., et al., "Restoration of Senescent Cardiac Angiogenic Activity", *Circulation*, 104 (17) *Supplement*, XP008049056, (Oct. 23, 2001),II.155 pg.

Hiragun, T., et al., "A Fibrogenic Cytokine, Platelet-Derived Growth Factor(PDGF), Enhances Mast Cell Growth Indirectly Via a SCF- and Fibroblast-Dependent Pathway", *J. Invest. Dermotol.*, 111, The Society For Investigative Dermatology, Inc.,(1998),213-217.

Webb, N. J., et al., "Vascular Endothelia Growth Factor (VEGF) is Released From Platelets During Blood Clotting: Implications for Measurement of Circulating VEGF Levels in Clinical Disease", *Clinical Science (London)*, 94 (4), (Apr. 1998), 395-404.

Schmitz, B., et al., "Megakaryocytes and Fibroblast—Interactions as Determined in Normal Human Bone Marrow Specimens", *Leukemia Research*, 19(9), (1995), 629-637.

\* cited by examiner

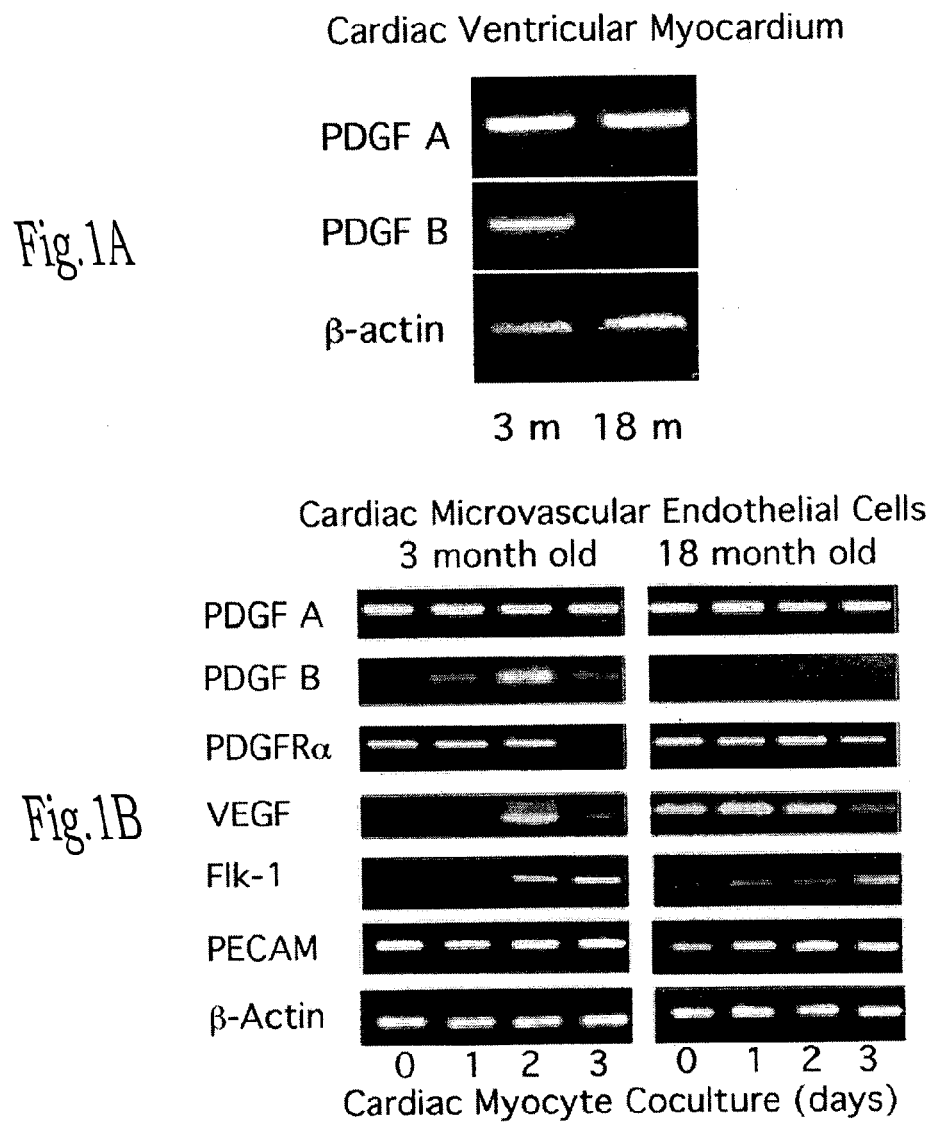
Fig.1A
Fig.1B
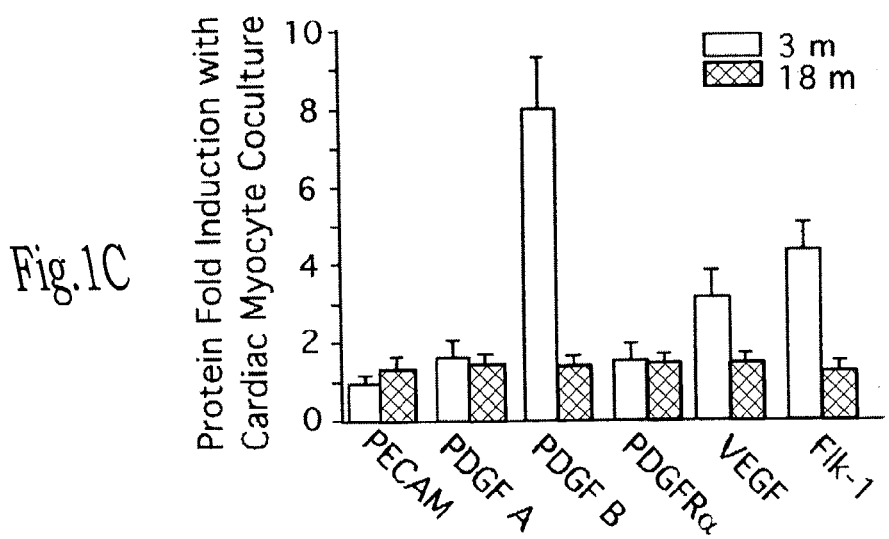
Fig.1C

| 3 month old | | 18 month old | | | |
|---|---|---|---|---|---|
| Transplant | heart | heart | silicon | lung | heart | heart |
| Pretreatment | - | - | - | - | VEGF | PDGF AB |
| Viability | 95% | 12% * | 100% | 75% | 17% | 100%** |

Fig.2A

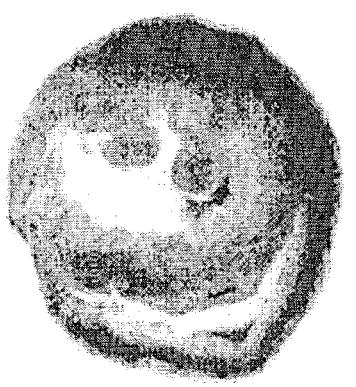
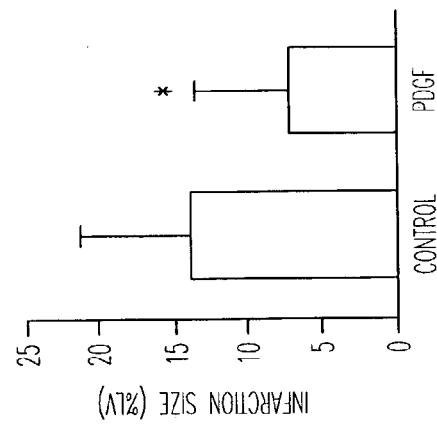
Fig.4A  Fig.4B  Fig.4C  Fig.4D

SEQUENCE LISTING

```
<160> NUMBER OF SEQ ID NOS: 36

<210> SEQ ID NO 1
<211> LENGTH: 204
<212> TYPE: PRT
<213> ORGANISM: Homo sapiens

<400> SEQUENCE: 1

Met Arg Thr Trp Ala Cys Leu Leu Leu Gly Cys Gly Tyr Leu Ala
1               5                   10                  15

His Ala Leu Ala Glu Glu Ala Glu Ile Pro Arg Glu Leu Ile Glu Arg
                20                  25                  30

Leu Ala Arg Ser Gln Ile His Ser Ile Arg Asp Leu Gln Arg Leu Leu
                35                  40                  45

Glu Ile Asp Ser Val Gly Ala Glu Asp Ala Leu Glu Thr Asn Leu Arg
    50                  55                  60

Ala His Gly Ser His Thr Val Lys His Val Pro Glu Lys Arg Pro Val
65                  70                  75                  80

Pro Ile Arg Arg Lys Arg Ser Ile Glu Glu Ala Ile Pro Ala Val Cys
                85                  90                  95

Lys Thr Arg Thr Val Ile Tyr Glu Ile Pro Arg Ser Gln Val Asp Pro
                100                 105                 110

Thr Ser Ala Asn Phe Leu Ile Trp Pro Pro Cys Val Glu Val Lys Arg
                115                 120                 125

Cys Thr Gly Cys Cys Asn Thr Ser Ser Val Lys Cys Gln Pro Ser Arg
                130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Ser Asn Leu Asn Pro Asp His Arg Glu Glu Glu
                180                 185                 190

Thr Gly Arg Arg Arg Glu Ser Gly Lys Lys Arg Lys
                195                 200

<210> SEQ ID NO 2
```

```
<211> LENGTH: 196
<212> TYPE: PRT
<213> ORGANISM: Mus musculus

<400> SEQUENCE: 2

Met Arg Thr Trp Ala Cys Leu Leu Leu Gly Cys Gly Tyr Leu Ala
 1               5                  10                  15

His Ala Leu Ala Glu Glu Ala Glu Ile Pro Arg Glu Leu Ile Glu Arg
            20                  25                  30

Leu Ala Arg Ser Gln Ile His Ser Ile Arg Asp Leu Gln Arg Leu Leu
            35                  40                  45

Glu Ile Asp Ser Val Gly Ala Glu Asp Ala Leu Glu Thr Ser Leu Arg
 50                  55                  60

Ala His Gly Ser His Ala Ile Asn His Val Pro Glu Lys Arg Pro Val
 65                  70                  75                  80

Pro Ile Arg Arg Lys Arg Ser Ile Glu Glu Ala Val Pro Ala Val Cys
                 85                  90                  95

Lys Thr Arg Thr Val Ile Tyr Glu Ile Pro Arg Ser Gln Val Asp Pro
                100                 105                 110

Thr Ser Ala Asn Phe Leu Ile Trp Pro Pro Cys Val Glu Val Lys Arg
            115                 120                 125

Cys Thr Gly Cys Cys Asn Thr Ser Ser Val Lys Cys Gln Pro Ser Arg
130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu Asp Leu Glu
                165                 170                 175

Cys Ala Cys Ala Thr Ser Asn Leu Asn Pro Asp His Arg Glu Glu Glu
            180                 185                 190

Thr Asp Val Arg
        195

<210> SEQ ID NO 3
<211> LENGTH: 241
<212> TYPE: PRT
<213> ORGANISM: Homo sapiens

<400> SEQUENCE: 3

Met Asn Arg Cys Trp Ala Leu Phe Leu Ser Leu Cys Cys Tyr Leu Arg
 1               5                  10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
            35                  40                  45

His Gly Asp Pro Gly Glu Glu Asp Gly Ala Glu Leu Asp Leu Asn Met
 50                  55                  60

Thr Arg Ser His Ser Gly Gly Glu Leu Glu Ser Leu Ala Arg Gly Arg
 65                  70                  75                  80

Arg Ser Leu Gly Ser Leu Thr Ile Ala Glu Pro Ala Met Ile Ala Glu
                 85                  90                  95

Cys Lys Thr Arg Thr Glu Val Phe Glu Ile Ser Arg Arg Leu Ile Asp
                100                 105                 110

Arg Thr Asn Ala Asn Phe Leu Val Trp Pro Pro Cys Val Glu Val Gln
            115                 120                 125

Arg Cys Ser Gly Cys Cys Asn Asn Arg Asn Val Gln Cys Arg Pro Thr
130                 135                 140
```

-continued

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Lys Gly Lys His Arg
    210                 215                 220

Lys Phe Lys His Thr His Asp Lys Thr Ala Leu Lys Glu Thr Leu Gly
225                 230                 235                 240

Ala

<210> SEQ ID NO 4
<211> LENGTH: 241
<212> TYPE: PRT
<213> ORGANISM: Mus musculus

<400> SEQUENCE: 4

Met Asn Arg Cys Trp Ala Leu Phe Leu Pro Leu Cys Cys Tyr Leu Arg
1               5                   10                  15

Leu Val Ser Ala Glu Gly Asp Pro Ile Pro Glu Glu Leu Tyr Glu Met
                20                  25                  30

Leu Ser Asp His Ser Ile Arg Ser Phe Asp Asp Leu Gln Arg Leu Leu
            35                  40                  45

His Arg Asp Ser Val Asp Glu Asp Gly Ala Glu Leu Asp Leu Asn Met
        50                  55                  60

Thr Arg Ala His Ser Gly Val Glu Leu Glu Ser Ser Arg Gly Arg
65                  70                  75                  80

Arg Ser Leu Gly Ser Leu Ala Ala Ala Glu Pro Ala Val Ile Ala Glu
                85                  90                  95

Cys Lys Thr Arg Thr Glu Val Phe Gln Ile Ser Arg Asn Leu Ile Asp
                100                 105                 110

Arg Thr Asn Ala Asn Phe Leu Val Trp Pro Pro Cys Val Glu Val Gln
            115                 120                 125

Arg Cys Ser Gly Cys Cys Asn Asn Arg Asn Val Gln Cys Arg Ala Ser
        130                 135                 140

Gln Val Gln Met Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Ile Val Thr Pro Arg Pro Val Thr Arg Ser
            180                 185                 190

Pro Gly Thr Ser Arg Glu Gln Arg Ala Lys Thr Pro Gln Ala Arg Val
        195                 200                 205

Thr Ile Arg Thr Val Arg Ile Arg Arg Pro Pro Lys Gly Lys His Arg
    210                 215                 220

Lys Phe Lys His Thr His Asp Lys Ala Ala Leu Lys Glu Thr Leu Gly
225                 230                 235                 240

Ala

<210> SEQ ID NO 5
<211> LENGTH: 161

```
<212> TYPE: PRT
<213> ORGANISM: Homo sapiens

<400> SEQUENCE: 5

Arg Ser Leu Gly Ser Leu Thr Ile Ala Glu Pro Ala Met Ile Ala Glu
 1               5                  10                  15

Cys Lys Thr Arg Thr Glu Val Phe Glu Ile Ser Arg Arg Leu Ile Asp
            20                  25                  30

Arg Thr Asn Ala Asn Phe Leu Val Trp Pro Pro Cys Val Glu Val Gln
        35                  40                  45

Arg Cys Ser Gly Cys Cys Asn Asn Arg Asn Val Gln Cys Arg Pro Thr
    50                  55                  60

Gln Val Gln Leu Arg Pro Val Gln Val Arg Lys Ile Glu Ile Val Arg
65                  70                  75                  80

Lys Lys Pro Ile Phe Lys Lys Ala Thr Val Thr Leu Glu Asp His Leu
                85                  90                  95

Ala Cys Lys Cys Glu Thr Val Ala Ala Ala Arg Pro Val Thr Arg Ser
            100                 105                 110

Pro Gly Gly Ser Gln Glu Gln Arg Ala Lys Thr Pro Gln Thr Arg Val
        115                 120                 125

Thr Ile Arg Thr Val Arg Val Arg Arg Pro Lys Gly Lys His Arg
130                 135                 140

Lys Phe Lys His Thr His Asp Lys Thr Ala Leu Lys Glu Thr Leu Gly
145                 150                 155                 160

Ala

<210> SEQ ID NO 6
<211> LENGTH: 119
<212> TYPE: PRT
<213> ORGANISM: Homo sapiens

<400> SEQUENCE: 6

Met Asn Arg Cys Trp Ala Leu Phe Leu Ser Leu Cys Cys Tyr Leu Arg
 1               5                  10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu
        115

<210> SEQ ID NO 7
<211> LENGTH: 20
<212> TYPE: DNA
<213> ORGANISM: Mus musculus

<400> SEQUENCE: 7
tcaaggtggc caaagtggag                                          20
```

```
<210> SEQ ID NO 8
<211> LENGTH: 20
<212> TYPE: DNA
<213> ORGANISM: Mus musculus

<400> SEQUENCE: 8
ctctctgtga caaggaagct                                               20

<210> SEQ ID NO 9
<211> LENGTH: 20
<212> TYPE: DNA
<213> ORGANISM: Mus musculus

<400> SEQUENCE: 9
atcgccgagt gcaagacgcg                                               20

<210> SEQ ID NO 10
<211> LENGTH: 20
<212> TYPE: DNA
<213> ORGANISM: Mus musculus

<400> SEQUENCE: 10
aagcaccatt ggccgtccga                                               20

<210> SEQ ID NO 11
<211> LENGTH: 20
<212> TYPE: DNA
<213> ORGANISM: Mus musculus

<400> SEQUENCE: 11
acagagactg agcgctgaca                                               20

<210> SEQ ID NO 12
<211> LENGTH: 20
<212> TYPE: DNA
<213> ORGANISM: Mus musculus

<400> SEQUENCE: 12
ttccaagaag gaaggaagca                                               20

<210> SEQ ID NO 13
<211> LENGTH: 30
<212> TYPE: DNA
<213> ORGANISM: Mus musculus

<400> SEQUENCE: 13
ggatccatga actttctgct gctgtcttgg                                    30

<210> SEQ ID NO 14
<211> LENGTH: 27
<212> TYPE: DNA
<213> ORGANISM: Mus musculus

<400> SEQUENCE: 14
ttctggcttt gtcctgtctt tctttgg                                       27

<210> SEQ ID NO 15
<211> LENGTH: 20
<212> TYPE: DNA
<213> ORGANISM: Mus musculus

<400> SEQUENCE: 15
cagcttgctc cttcctcatc                                               20
```

<210> SEQ ID NO 16
<211> LENGTH: 20
<212> TYPE: DNA
<213> ORGANISM: Mus musculus

<400> SEQUENCE: 16
tctggagagc aaaccaacca                                          20

<210> SEQ ID NO 17
<211> LENGTH: 20
<212> TYPE: DNA
<213> ORGANISM: Mus musculus

<400> SEQUENCE: 17
tgtccaaggt ctgaagaaga                                          20

<210> SEQ ID NO 18
<211> LENGTH: 20
<212> TYPE: DNA
<213> ORGANISM: Mus musculus

<400> SEQUENCE: 18
caggacaaac accacatcca                                          20

<210> SEQ ID NO 19
<211> LENGTH: 20
<212> TYPE: DNA
<213> ORGANISM: Mus musculus

<400> SEQUENCE: 19
caagcggtcg tgaatgacac                                          20

<210> SEQ ID NO 20
<211> LENGTH: 21
<212> TYPE: DNA
<213> ORGANISM: Mus musculus

<400> SEQUENCE: 20
cactgccttg actgtcttaa g                                        21

<210> SEQ ID NO 21
<211> LENGTH: 21
<212> TYPE: DNA
<213> ORGANISM: Mus musculus

<400> SEQUENCE: 21
gtgggccgct ctaggcacca a                                        21

<210> SEQ ID NO 22
<211> LENGTH: 24
<212> TYPE: DNA
<213> ORGANISM: Mus musculus

<400> SEQUENCE: 22
ctctttgatg tcacgcacga tttc                                     24

<210> SEQ ID NO 23
<211> LENGTH: 21
<212> TYPE: DNA
<213> ORGANISM: Mus musculus

<400> SEQUENCE: 23

```
gtgggccgct ctaggcacca a                                          21

<210> SEQ ID NO 24
<211> LENGTH: 24
<212> TYPE: DNA
<213> ORGANISM: Mus musculus

<400> SEQUENCE: 24
ctctttgatg tcacgcacga tttc                                       24

<210> SEQ ID NO 25
<211> LENGTH: 20
<212> TYPE: DNA
<213> ORGANISM: Mus musculus

<400> SEQUENCE: 25
tcaaggtggc caaagtggag                                            20

<210> SEQ ID NO 26
<211> LENGTH: 20
<212> TYPE: DNA
<213> ORGANISM: Mus musculus

<400> SEQUENCE: 26
ctctctgtga caaggaagct                                            20

<210> SEQ ID NO 27
<211> LENGTH: 20
<212> TYPE: DNA
<213> ORGANISM: Mus musculus

<400> SEQUENCE: 27
atcgccgagt gcaagacgcg                                            20

<210> SEQ ID NO 28
<211> LENGTH: 20
<212> TYPE: DNA
<213> ORGANISM: Mus musculus

<400> SEQUENCE: 28
aagcaccatt ggccgtccga                                            20

<210> SEQ ID NO 29
<211> LENGTH: 20
<212> TYPE: DNA
<213> ORGANISM: Mus musculus

<400> SEQUENCE: 29
tgtccaaggt ctgaagaaga                                            20

<210> SEQ ID NO 30
<211> LENGTH: 20
<212> TYPE: DNA
<213> ORGANISM: Mus musculus

<400> SEQUENCE: 30
caggacaaac accacatcca                                            20

<210> SEQ ID NO 31
<211> LENGTH: 20
<212> TYPE: DNA
<213> ORGANISM: Mus musculus

<400> SEQUENCE: 31
```

```
caagcggtcg tgaatgacac                                                    20

<210> SEQ ID NO 32
<211> LENGTH: 21
<212> TYPE: DNA
<213> ORGANISM: Mus musculus

<400> SEQUENCE: 32
cactgccttg actgtcttaa g                                                  21

<210> SEQ ID NO 33
<211> LENGTH: 23
<212> TYPE: DNA
<213> ORGANISM: Mus musculus

<400> SEQUENCE: 33
ggaagagtga gcggccatca agg                                                23

<210> SEQ ID NO 34
<211> LENGTH: 22
<212> TYPE: DNA
<213> ORGANISM: Mus musculus

<400> SEQUENCE: 34
ctgctggaga ggttattcct cg                                                 22

<210> SEQ ID NO 35
<211> LENGTH: 1089
<212> TYPE: PRT
<213> ORGANISM: Homo sapiens

<400> SEQUENCE: 35

Met Gly Thr Ser His Pro Ala Phe Leu Val Leu Gly Cys Leu Leu Thr
 1               5                  10                  15

Gly Leu Ser Leu Ile Leu Cys Gln Leu Ser Leu Pro Ser Ile Leu Pro
             20                  25                  30

Asn Glu Asn Glu Lys Val Val Gln Leu Asn Ser Ser Phe Ser Leu Arg
         35                  40                  45

Cys Phe Gly Glu Ser Glu Val Ser Trp Gln Tyr Pro Met Ser Glu Glu
     50                  55                  60

Glu Ser Ser Asp Val Glu Ile Arg Asn Glu Glu Asn Asn Ser Gly Leu
 65                  70                  75                  80

Phe Val Thr Val Leu Glu Val Ser Ala Ser Ala Ala His Thr Gly
                 85                  90                  95

Leu Tyr Thr Cys Tyr Tyr Asn His Thr Gln Thr Glu Glu Asn Glu Leu
                100                 105                 110

Glu Gly Arg His Ile Tyr Ile Tyr Val Pro Asp Pro Asp Val Ala Phe
            115                 120                 125

Val Pro Leu Gly Met Thr Asp Tyr Leu Val Ile Val Glu Asp Asp Asp
        130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205
```

```
Lys Ala Thr Ser Glu Leu Asp Leu Glu Met Glu Ala Leu Lys Thr Val
    210                 215                 220
Tyr Lys Ser Gly Glu Thr Ile Val Val Thr Cys Ala Val Phe Asn Asn
225                 230                 235                 240
Glu Val Val Asp Leu Gln Trp Thr Tyr Pro Gly Glu Val Lys Gly Lys
                245                 250                 255
Gly Ile Thr Met Leu Glu Glu Ile Lys Val Pro Ser Ile Lys Leu Val
                260                 265                 270
Tyr Thr Leu Thr Val Pro Glu Ala Thr Val Lys Asp Ser Gly Asp Tyr
        275                 280                 285
Glu Cys Ala Ala Arg Gln Ala Thr Arg Glu Val Lys Glu Met Lys Lys
    290                 295                 300
Val Thr Ile Ser Val His Glu Lys Gly Phe Ile Glu Ile Lys Pro Thr
305                 310                 315                 320
Phe Ser Gln Leu Glu Ala Val Asn Leu His Glu Val Lys His Phe Val
                325                 330                 335
Val Glu Val Arg Ala Tyr Pro Pro Arg Ile Ser Trp Leu Lys Asn
                340                 345                 350
Asn Leu Thr Leu Ile Glu Asn Leu Thr Glu Ile Thr Thr Asp Val Glu
        355                 360                 365
Lys Ile Gln Glu Ile Arg Tyr Arg Ser Lys Leu Lys Leu Ile Arg Ala
    370                 375                 380
Lys Glu Glu Asp Ser Gly His Tyr Thr Ile Val Ala Gln Asn Glu Asp
385                 390                 395                 400
Ala Val Lys Ser Tyr Thr Phe Glu Leu Leu Thr Gln Val Pro Ser Ser
                405                 410                 415
Ile Leu Asp Leu Val Asp Asp His His Gly Ser Thr Gly Gly Gln Thr
                420                 425                 430
Val Arg Cys Thr Ala Glu Gly Thr Pro Leu Pro Asp Ile Glu Trp Met
        435                 440                 445
Ile Cys Lys Asp Ile Lys Lys Cys Asn Asn Glu Thr Ser Trp Thr Ile
    450                 455                 460
Leu Ala Asn Asn Val Ser Asn Ile Ile Thr Glu Ile His Ser Arg Asp
465                 470                 475                 480
Arg Ser Thr Val Glu Gly Arg Val Thr Phe Ala Lys Val Glu Glu Thr
                485                 490                 495
Ile Ala Val Arg Cys Leu Ala Lys Asn Leu Leu Gly Ala Glu Asn Arg
                500                 505                 510
Glu Leu Lys Leu Val Ala Pro Thr Leu Arg Ser Glu Leu Thr Val Ala
        515                 520                 525
Ala Ala Val Leu Val Leu Leu Val Ile Val Ile Ile Ser Leu Ile Val
    530                 535                 540
Leu Val Val Ile Trp Lys Gln Lys Pro Arg Tyr Glu Ile Arg Trp Arg
545                 550                 555                 560
Val Ile Glu Ser Ile Ser Pro Asp Gly His Glu Tyr Ile Tyr Val Asp
                565                 570                 575
Pro Met Gln Leu Pro Tyr Asp Ser Arg Trp Glu Phe Pro Arg Asp Gly
                580                 585                 590
Leu Val Leu Gly Arg Val Leu Gly Ser Gly Ala Phe Gly Lys Val Val
        595                 600                 605
Glu Gly Thr Ala Tyr Gly Leu Ser Arg Ser Gln Pro Val Met Lys Val
    610                 615                 620
```

-continued

```
Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
            645                 650                 655

Ile Val Asn Leu Leu Gly Ala Cys Thr Lys Ser Gly Pro Ile Tyr Ile
        660                 665                 670

Ile Thr Glu Tyr Cys Phe Tyr Gly Asp Leu Val Asn Tyr Leu His Lys
    675                 680                 685

Asn Arg Asp Ser Phe Leu Ser His His Pro Glu Lys Pro Lys Lys Glu
690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
            725                 730                 735

Ala Asp Thr Thr Gln Tyr Val Pro Met Leu Glu Arg Lys Glu Val Ser
        740                 745                 750

Lys Tyr Ser Asp Ile Gln Arg Ser Leu Tyr Asp Arg Pro Ala Ser Tyr
    755                 760                 765

Lys Lys Lys Ser Met Leu Asp Ser Glu Val Lys Asn Leu Leu Ser Asp
770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
            805                 810                 815

Arg Asp Leu Ala Ala Arg Asn Val Leu Leu Ala Gln Gly Lys Ile Val
        820                 825                 830

Lys Ile Cys Asp Phe Gly Leu Ala Arg Asp Ile Met His Asp Ser Asn
    835                 840                 845

Tyr Val Ser Lys Gly Ser Thr Phe Leu Pro Val Lys Trp Met Ala Pro
850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
            885                 890                 895

Pro Gly Met Met Val Asp Ser Thr Phe Tyr Asn Lys Ile Lys Ser Gly
        900                 905                 910

Tyr Arg Met Ala Lys Pro Asp His Ala Thr Ser Glu Val Tyr Glu Ile
    915                 920                 925

Met Val Lys Cys Trp Asn Ser Glu Pro Glu Lys Arg Pro Ser Phe Tyr
930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
            965                 970                 975

Val Ala Arg Met Arg Val Asp Ser Asp Asn Ala Tyr Ile Gly Val Thr
        980                 985                 990

Tyr Lys Asn Glu Glu Asp Lys Leu Lys Asp Trp Glu Gly Gly Leu Asp
    995                 1000                1005

Glu Gln Arg Leu Ser Ala Asp Ser Gly Tyr Ile Ile Pro Leu Pro Asp
    1010                1015                1020

Ile Asp Pro Val Pro Glu Glu Asp Leu Gly Lys Arg Asn Arg His
1025                1030                1035                1040

Ser Ser Gln Thr Ser Glu Glu Ser Ala Ile Glu Thr Gly Ser Ser Ser
```

```
                    1045               1050              1055
Ser Thr Phe Ile Lys Arg Glu Asp Glu Thr Ile Glu Asp Ile Asp Met
            1060               1065              1070
Met Asp Asp Ile Gly Ile Asp Ser Ser Asp Leu Val Glu Asp Ser Phe
            1075               1080              1085
Leu

<210> SEQ ID NO 36
<211> LENGTH: 1106
<212> TYPE: PRT
<213> ORGANISM: Homo sapiens

<400> SEQUENCE: 36

Met Arg Leu Pro Gly Ala Met Pro Ala Leu Ala Leu Lys Gly Glu Leu
 1               5                  10                  15
Leu Leu Leu Ser Leu Leu Leu Leu Glu Pro Gln Ile Ser Gln Gly
                20                  25                  30
Leu Val Val Thr Pro Pro Gly Pro Glu Leu Val Leu Asn Val Ser Ser
                35                  40                  45
Thr Phe Val Leu Thr Cys Ser Gly Ser Ala Pro Val Val Trp Glu Arg
 50                  55                  60
Met Ser Gln Glu Pro Pro Gln Glu Met Ala Lys Ala Gln Asp Gly Thr
65                  70                  75                  80
Phe Ser Ser Val Leu Thr Leu Thr Asn Leu Thr Gly Leu Asp Thr Gly
                85                  90                  95
Glu Tyr Phe Cys Thr His Asn Asp Ser Arg Gly Leu Glu Thr Asp Glu
                100                 105                 110
Arg Lys Arg Leu Tyr Ile Phe Val Pro Asp Pro Thr Val Gly Phe Leu
                115                 120                 125
Pro Asn Asp Ala Glu Glu Leu Phe Ile Phe Leu Thr Glu Ile Thr Glu
                130                 135                 140
Ile Thr Ile Pro Cys Arg Val Thr Asp Pro Gln Leu Val Val Thr Leu
145                 150                 155                 160
His Glu Lys Lys Gly Asp Val Ala Leu Pro Val Pro Tyr Asp His Gln
                165                 170                 175
Arg Gly Phe Ser Gly Ile Phe Glu Asp Arg Ser Tyr Ile Cys Lys Thr
                180                 185                 190
Thr Ile Gly Asp Arg Glu Val Asp Ser Asp Ala Tyr Tyr Val Tyr Arg
                195                 200                 205
Leu Gln Val Ser Ser Ile Asn Val Ser Val Asn Ala Val Gln Thr Val
                210                 215                 220
Val Arg Gln Gly Glu Asn Ile Thr Leu Met Cys Ile Val Ile Gly Asn
225                 230                 235                 240
Glu Val Val Asn Phe Glu Trp Thr Tyr Pro Arg Lys Glu Ser Gly Arg
                245                 250                 255
Leu Val Glu Pro Val Thr Asp Phe Leu Leu Asp Met Pro Tyr His Ile
                260                 265                 270
Arg Ser Ile Leu His Ile Pro Ser Ala Glu Leu Glu Asp Ser Gly Thr
                275                 280                 285
Tyr Thr Cys Asn Val Thr Glu Ser Val Asn Asp His Gln Asp Glu Lys
                290                 295                 300
Ala Ile Asn Ile Thr Val Val Glu Ser Gly Tyr Val Arg Leu Leu Gly
305                 310                 315                 320
Glu Val Gly Thr Leu Gln Phe Ala Glu Leu His Arg Ser Arg Thr Leu
```

-continued

```
                325                 330                 335
Gln Val Val Phe Glu Ala Tyr Pro Pro Thr Val Leu Trp Phe Lys
                340                 345                 350
Asp Asn Arg Thr Leu Gly Asp Ser Ser Ala Gly Glu Ile Ala Leu Ser
                355                 360                 365
Thr Arg Asn Val Ser Glu Thr Arg Tyr Val Ser Glu Leu Thr Leu Val
                370                 375                 380
Arg Val Lys Val Ala Glu Ala Gly His Tyr Thr Met Arg Ala Phe His
385                 390                 395                 400
Glu Asp Ala Glu Val Gln Leu Ser Phe Gln Leu Gln Ile Asn Val Pro
                405                 410                 415
Val Arg Val Leu Glu Leu Ser Glu Ser His Pro Asp Ser Gly Glu Gln
                420                 425                 430
Thr Val Arg Cys Arg Gly Arg Gly Met Pro Gln Pro Asn Ile Ile Trp
                435                 440                 445
Ser Ala Cys Arg Asp Leu Lys Arg Cys Pro Arg Glu Leu Pro Pro Thr
                450                 455                 460
Leu Leu Gly Asn Ser Ser Glu Glu Ser Gln Leu Glu Thr Asn Val
465                 470                 475                 480
Thr Tyr Trp Glu Glu Gln Glu Phe Glu Val Val Ser Thr Leu Arg
                485                 490                 495
Leu Gln His Val Asp Arg Pro Leu Ser Val Arg Cys Thr Leu Arg Asn
                500                 505                 510
Ala Val Gly Gln Asp Thr Gln Glu Val Ile Val Val Pro His Ser Leu
                515                 520                 525
Pro Phe Lys Val Val Ile Ser Ala Ile Leu Ala Leu Val Val Leu
                530                 535                 540
Thr Ile Ile Ser Leu Ile Ile Leu Ile Met Leu Trp Gln Lys Lys Pro
545                 550                 555                 560
Arg Tyr Glu Ile Arg Trp Lys Val Ile Glu Ser Val Ser Ser Asp Gly
                565                 570                 575
His Glu Tyr Ile Tyr Val Asp Pro Met Gln Leu Pro Tyr Asp Ser Thr
                580                 585                 590
Trp Glu Leu Pro Arg Asp Gln Leu Val Leu Gly Arg Thr Leu Gly Ser
                595                 600                 605
Gly Ala Phe Gly Gln Val Val Glu Ala Thr Ala His Gly Leu Ser His
                610                 615                 620
Ser Gln Ala Thr Met Lys Val Ala Val Lys Met Leu Lys Ser Thr Ala
625                 630                 635                 640
Arg Ser Ser Glu Lys Gln Ala Leu Met Ser Glu Leu Lys Ile Met Ser
                645                 650                 655
His Leu Gly Pro His Leu Asn Val Val Asn Leu Leu Gly Ala Cys Thr
                660                 665                 670
Lys Gly Gly Pro Ile Tyr Ile Ile Thr Glu Tyr Cys Arg Tyr Gly Asp
                675                 680                 685
Leu Val Asp Tyr Leu His Arg Asn Lys His Thr Phe Leu Gln His His
                690                 695                 700
Ser Asp Lys Arg Arg Pro Pro Ser Ala Glu Leu Tyr Ser Asn Ala Leu
705                 710                 715                 720
```

-continued

Pro Val Gly Leu Pro Leu Pro Ser His Val Ser Leu Thr Gly Glu Ser
            725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
            755                 760                 765

Ser Asn Tyr Met Ala Pro Tyr Asp Asn Tyr Val Pro Ser Ala Pro Glu
            770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
            805                 810                 815

Leu Ala Ser Lys Asn Cys Val His Arg Asp Leu Ala Ala Arg Asn Val
            820                 825                 830

Leu Ile Cys Glu Gly Lys Leu Val Lys Ile Cys Asp Phe Gly Leu Ala
            835                 840                 845

Arg Asp Ile Met Arg Asp Ser Asn Tyr Ile Ser Lys Gly Ser Thr Phe
850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
            885                 890                 895

Phe Thr Leu Gly Gly Thr Pro Tyr Pro Glu Leu Pro Met Asn Glu Gln
            900                 905                 910

Phe Tyr Asn Ala Ile Lys Arg Gly Tyr Arg Met Ala Gln Pro Ala His
            915                 920                 925

Ala Ser Asp Glu Ile Tyr Glu Ile Met Gln Lys Cys Trp Glu Glu Lys
            930                 935                 940

Phe Glu Ile Arg Pro Pro Phe Ser Gln Leu Val Leu Leu Leu Glu Arg
945                 950                 955                 960

Leu Leu Gly Glu Gly Tyr Lys Lys Lys Tyr Gln Gln Val Asp Glu Glu
            965                 970                 975

Phe Leu Arg Ser Asp His Pro Ala Ile Leu Arg Ser Gln Ala Arg Leu
            980                 985                 990

Pro Gly Phe His Gly Leu Arg Ser Pro Leu Asp Thr Ser Ser Val Leu
            995                 1000                1005

Tyr Thr Ala Val Gln Pro Asn Glu Gly Asp Asn Asp Tyr Ile Ile Pro
1010                1015                1020

Leu Pro Asp Pro Lys Pro Glu Val Ala Asp Glu Gly Pro Leu Glu Gly
1025                1030                1035                1040

Ser Pro Ser Leu Ala Ser Ser Thr Leu Asn Glu Val Asn Thr Ser Ser
            1045                1050                1055

Thr Ile Ser Cys Asp Ser Pro Leu Glu Pro Gln Asp Glu Pro Glu Pro
            1060                1065                1070

Glu Pro Gln Leu Glu Leu Gln Val Glu Pro Glu Pro Glu Leu Glu Gln
            1075                1080                1085

Leu Pro Asp Ser Gly Cys Pro Ala Pro Arg Ala Glu Ala Glu Asp Ser
            1090                1095                1100

Phe Leu
1105

ENDOTHELIAL PRECURSOR CELLS FOR ENHANCING AND RESTORING VASCULAR FUNCTION

This application claims priority to PCT Application Ser. No. PCT/US02/25175, filed simultaneously herewith on Aug. 8, 2002, which is a continuation-in-part of U.S. application Ser. No. 10/215,271, filed Aug. 8, 2002, which claims priority to U.S. Provisional Application Ser. No. 60/357,328, filed Feb. 15, 2002, and to U.S. Provisional Application Ser. No. 60/311,238, filed Aug. 9, 2001.

GOVERNMENT FUNDING

The invention described herein was made with United States Government support under Grant Numbers HL59312, AG20918 and HL67839 awarded by the National Institutes of Health. The United States Government has certain rights in this invention.

FIELD OF THE INVENTION

The invention relates to bone marrow cells, cloned endothelial precursor cells and the stem cells from which they are derived. Such cells can be genetically modified to express useful gene products. The invention further relates to methods for using these cells for treating vascular diseases, including heart disease and atherosclerosis.

BACKGROUND OF THE INVENTION

In the United States and Western Europe, cardiovascular disease and its associated maladies, dysfunctions and complications are a principal cause of disability and the chief cause of death. One specific entity significantly contributing to this pathophysiologic process is atherosclerosis, which has been generally recognized as the leading health care problem both with respect to mortality and health care costs. The American Heart Association estimates that 953,110 persons died of cardiovascular diseases in 1997 (41.2 percent of all deaths), more than the number of mortality for cancer (539,377), accidents (95,644) and HIV (16,516) combined. Furthermore, the American Heart Association calculates that close to a quarter of the population of the United States suffers from one or more forms of cardiovascular disease. Moreover, the medical costs associated with coronary heart disease are estimated at $95 billion dollars a year. Gonzalez & Kannewurf, 55 (19) American Journal of Health-System Pharmacy S4-7 (Supp. 1, 1998).

Atherosclerosis is a disease characterized by the deposition of fatty substances, primarily cholesterol, and subsequent fibrosis in the inner layer (intima) of an artery, resulting in plaque deposition on the inner surface of the arterial wall and degenerative changes within it. The ubiquitous arterial fatty plaque is the earliest lesion of atherosclerosis and is a grossly flat, lipid-rich atheroma consisting of macrophages (white blood cells) and smooth muscle fibers. The fibrous plaque of the various forms of advanced atherosclerosis has increased intimal smooth muscle cells surrounded by a connective tissue matrix and variable amounts of intracellular and extracellular lipid. At the luminal surface of the artery, a dense fibrous cap of smooth muscle or connective tissue usually covers this plaque or lesion. Beneath the fibrous cap, the lesions are highly cellular consisting of macrophages, other leukocytes and smooth muscle cells. Deep in this cell-rich region may be areas of cholesterol crystals, necrotic debris and calcification.

If allowed to progress, the disease can cause narrowing and obstruction of the lumen of the artery, diminished or occluded blood flow and, consequently, ischemia or infarction of the predominantly affected organ or anatomical part, such as the brain, heart, intestine or extremities. The result can be significant loss of function, loss of cellular substance, emergency medical and/or surgical procedures, and significant disability or death. Alternatively, the arterial wall can be severely weakened by the infiltration of the muscular layer with the lipid (cholesterol), inflammatory white blood cells, connective tissue and calcium, resulting in soft and/or brittle areas which can become segmentally dilated (aneurysmal) and rupture or crack leading to organ, limb or even life-threatening hemorrhage.

Ischemic heart disease is the most common cause of morbidity and mortality in the population over the age of sixty-five. Sullivan, L. W. 1990. Healthy people 2000. *N Engl J Med.* 323:1065–1067; Wei, J. Y. 1992. Age and the cardiovascular system. *N Engl J Med.* 327:1735–1739; Association, A. H. 1993–1995. Heart and stroke facts statistical supplement/1994–1996. Dallas, Tex.: The Association. Elucidation of the cellular and molecular pathways that are impaired with aging is critical to the development of specific strategies to prevent and reduce the pathology of cardiovascular disease associated with advancing age.

In younger individuals, myocardial ischemia induces the development of a collateral vasculature supply that partially protects the cardiac tissue from subsequent coronary events. Hirai et al. (1989) *Circulation.* 79:791–796; Ejiri et al. (1990) *J Cardiol.* 20:31–37; Kodama et al. (1996). *J Am Coll Cardiol.* 27:1133–1139; Banerjee et al., (1993) *Int J Cardiol.* 38:263–271. However, angiogenesis is impaired in older heart and peripheral vascular beds. Hudlicka et al. (1996) *J Vasc Res.* 33:266–287; Isoyama (1994) *Drugs Aging.* 5:102–115; Tomanek et al. (1990) *Am J Physiol.* 259: H1681–1687; Anversa et al. (1994) *Am J Physiol.* 267: H1062–1073; Azhar et al. (1999) *Exp Gerontol.* 34:699–714; Rakusan et al. (1994) *Cardiovasc Res.* 28:969–972; Rivard et al. (1999) *Circulation.* 99:111–120; Reed et al. (2000) *J Cell Biochem.* 77:116–126. The etiology of the impaired angiogenic activity in the senescent heart and within aging blood vessels is not known. In fact, despite recent advances in our understanding of the molecular pathways regulating angiogenesis during embryonic development, the mechanistic alterations in angiogenic function in the senescent vasculature are not well understood.

The etiology of atherosclerotic plaques is similarly a matter of debate and uncertainty. Much research in recent years has focused upon the molecular pathways of cholesterol deposition and upon altering serum lipoprotein concentrations for achieving therapeutic effect. Goldstein et al., Science 292: 1310–12. There has been speculation that the replicative senescence of vascular endothelium plays a role in the etiology of atherosclerosis. Chang et al., 1995 Proc. Natl. Acad. Sci. 92:11190–94. Moreover, studies show that telomere length can determine the lifespan of cells. Bodnar et al., 1998 Science 279: 349–53. In addition, cells with a morphology similar to senescent cells co-localize with mature atherosclerotic plaques. Osamu et al., 1989 Am. J. Pathol. 135: 967–76. However, methods for grafting young vascular endothelial cells into an old animal have been unavailable.

Therefore, new approaches are needed for counteracting the age-associated changes in angiogenic pathways and the repair of endothelium within senescent vascular tissues.

SUMMARY OF THE INVENTION

According to the invention, administration of endothelial precursor cells can reverse the effects of aging on mammalian vascular tissues. Such administration can therefore be used for treating vascular diseases or conditions. Such cells have the ability to find their way to and then integrate into various tissues, including vascular tissues, bone marrow and cardiac tissues. After becoming associated with these tissues, the endothelial precursor cells can restore angiogenesis and/or generate myocytes. Moreover, such endothelial precursor cells can deliver PDGF to cardiac tissues, wherein the PDGF is also useful for restoring angiogenesis in the peripheral vasculature and in senescent cardiac tissues.

The invention therefore provides a method for treating a vascular condition in a mammal that involves administering to the mammal a therapeutically effective amount of endothelial precursor cells. In some embodiments, the endothelial precursor cells can express c-kit. In other embodiments, the endothelial precursor cells can express or bind platelet derived growth factor. In other embodiments, the endothelial precursor cells can induce expression of platelet derived growth factor in neighboring (e.g. co-cultured) cells.

The vascular condition can be, for example, a myocardial infarction; in this case administration of the endothelial precursor cells reduces the size of the myocardial infarction. In other embodiments, the vascular condition is atherosclerosis. The vascular condition can also be ischemia, tachycardia, congestive heart failure, peripheral vasculature disorder, hypertension, stroke, thrombosis, arrhythmia or tachycardia. While any mammal may be treated by the methods of the invention, in many embodiments, the mammal is a human.

The endothelial precursor cells can be administered intravascularly, intravenously, intraarterially, intraperitoneally, via intraventricular infusion, via infusion catheter, via balloon catheter, via bolus injection, or via direct application to tissue surfaces during surgery. A therapeutically effective amount of endothelial precursor cells can be, for example, about $10^2$ to about $10^{10}$ endothelial precursor cells, or about $10^4$ to about $10^9$ endothelial precursor cells.

In some embodiments, the endothelial precursor cells are exposed to platelet derived growth factor AB prior to administration to the mammal. According to the invention, older bone marrow normally cannot be used for treating vascular conditions, but when cultured in the presence of platelet derived growth factor, the older bone marrow takes on many of the characteristics of young bone marrow and becomes useful for treating vascular conditions.

The endothelial precursor cells can be syngeneic endothelial precursor cells originally obtained from the mammal to be treated. Administration of such cells will minimize immunological reactions that may be directed against the endothelial precursor cells. To facilitate isolation of the endothelial precursor cells, the mammal can be pre-treated with G-CSF, GM-CSF, VEGF, SCF, bFGF, SDF-1, interleukin 1 or interleukin 8 before isolation of the endothelial precursor cells.

The endothelial precursor cells employed in the methods of the invention can be derived from bone marrow, peripheral blood, umbilical cord blood, liver tissue or fat. The endothelial precursor cells can also be derived from an embryonic stem cell line. In other embodiments, the endothelial precursor cells are derived from at least one nuclear transfer unit formed in vitro by fusion of an enucleated oocyte with a somatic cell from the mammal. The endothelial precursor cells can also be derived from an inner cell mass of a blastocyst generated in vitro.

In some embodiments, the endothelial precursor cells can comprise a heterologous DNA encoding a therapeutic agent that can be expressed in the endothelial precursor cells. Such a therapeutic agent can, for example, be a platelet derived growth factor polypeptide having any one of SEQ ID NO:1, SEQ ID NO:2, SEQ ID NO:3, SEQ ID NO:4, SEQ ID NO:5 or SEQ ID NO:6. The therapeutic agent can also be a platelet derived growth factor receptor, for example, having SEQ ID NO:35 or SEQ ID NO:36. Other examples of therapeutic agents include a cytokine, a growth factor, a hormone, streptokinase, tissue plasminogen activator, plasmin, urokinase, an anti-thrombotic agent, an anti-inflammatory agent, a metalloproteinase inhibitor or a nematode-extracted anticoagulant protein.

The invention further provides methods for treating or preventing a myocardial infarction in a patient having or at risk for developing a myocardial infarction. The method involves administering to the patient a therapeutically effective amount of an agent that restores a PDGF B dependent communication pathway.

The invention also provides a method for reducing the size of a myocardial infarction in a patient at risk for developing a myocardial infarction, such a method can include administering to the patient a therapeutically effective amount of an agent that restores a PDGF B dependent communication pathway. The size of the myocardial infarction can be measured by the extent of myocardial necrosis.

The invention also provides a method of restoring cardiac angiogenic function in a patient having senescent cardiac angiogenic function. Such a method can include administering to the patient a therapeutically effective amount of an agent that restores a PDGF B dependent communication pathway.

The invention also provides a method of restoring vascular function in a patient having peripheral vasculature disorder (PVD), wherein the method comprises administering to the patient a therapeutically effective amount of an agent that restores a PDGF B dependent communication pathway.

The invention further provides a method of restoring vascular function in or near the brain of a patient in need of such restoration, wherein the method comprises administering to the patient a therapeutically effective amount of an agent that restores a PDGF B dependent communication pathway. The patient may be suffering or may have suffered a stroke.

The invention further provides a method of restoring cardioplastic potential of bone marrow cells obtained from a patient having senescent cardiac angiogenic function, wherein the method comprises administering an effective amount of PDGF AB to a culture of said bone marrow cells.

The invention also provides a method of treating cardiovascular dysfunction, wherein the method comprises administering to a patient suffering from said dysfunction, a therapeutically effective amount of cardiac myocytes, wherein said cardiac myocytes are derived from autologous stem cells and wherein said stem cells have been cultured in the presence of PDGF AB. The cardiovascular dysfunction can be at least one of myocardial infarction, ischemia, peripheral vasculature disorder (PVD), stroke, arrhythmia, tachycardia, or heart failure.

The invention further provides a method of restoring cardiac angiogenic function in a patient having senescent cardiac angiogenic function, wherein the method comprises administering to the patient a therapeutically effective amount of cardiac myocytes, wherein said cardiac myocytes are derived from autologous stem cells and wherein said stem cells have been cultured in the presence of PDGF AB.

The invention also provides a method of restoring cardioplastic potential of stem cells obtained from a patient having senescent cardiac angiogenic function, wherein the method comprises administering to a culture of said stem cells, an effective amount of PDGF AB.

The invention further provides a method of increasing the kinetics of cardiac myocyte derivation from bone marrow cells obtained from a patient having senescent cardiac angiogenic function, wherein the method involves administering to a culture of said bone marrow cells an effective amount of PDGF AB.

The invention also provides a method of increasing the kinetics of cardiac myocyte derivation from stem cells obtained from a patient having senescent cardiac angiogenic function, wherein the method comprises administering to a culture of said stem cells an effective amount of PDGF AB.

The agent that restores a PDGF B dependent communication pathway can be at least one of PDGF AB, PDGF BB, PDGF A, PDGF B, stem cells, young bone marrow endothelial precursor cells, epidermal growth factor or small molecule. The route of administration is by intravascular, intravenous, intraarterial, intraperitoneal, or intraventricular infusion, stem cell, infusion catheter, balloon catheter, bolus injection, direct application to tissue surfaces during surgery, oral or topical administration. The stem cells or young bone marrow, or endothelial precursor cells can be genetically modified to express a heterologous protein, RNA, or hormone. The stem cells or young bone marrow endothelial precursor cells can be genetically modified to over-express a native protein, RNA or hormone. The stem cells or young bone marrow endothelial precursor cells may also be modified to express, for example, cytokines, growth factors, hormones, signaling intermediates, sugar moieties, small molecules, anti-sense RNA, and to perform various biological actions that facilitate vascularization of senescent tissues.

The invention further provides cardiac myocytes exhibiting cardioplastic potential and derived from endothelial precursor cells obtained from a patient having senescent cardiac angiogenic function, said cardiac myocytes obtained through a process of culturing said endothelial precursor cell in the presence of an effective amount of PDGF, for example, PDGF AB or PDGF BB. Such endothelial precursor cells can be derived from bone marrow, peripheral blood, umbilical cord blood, organs, tissue, or fat.

The invention also provides a method of delivering platelet derived growth factor to cardiac tissues of a mammal comprising administering live endothelial precursor cells to a mammal and thereby delivering platelet derived growth factor to cardiac tissues. The platelet-derived growth factor can be PDGF B, PDGF A, PDGF AB, PDGF BB or any other form of PDGF that has activity or can combine with a PDGF polypeptide to generate an active PGDF protein.

The invention further provides a method of delivering platelet derived growth factor to cardiac tissues of a mammal comprising administering live young bone marrow cells to a mammal and thereby delivering platelet derived growth factor to cardiac tissues.

The invention also provides a method of preventing myocardial necrosis comprising administering live endothelial precursor cells to a mammal and thereby delivering platelet derived growth factor B to cardiac tissues in danger of myocardial necrosis.

The endothelial precursor cells and/or young bone marrow cells can express platelet-derived growth factor B upon association with cardiac myocytes within the cardiac tissues. Cardiac microvascular endothelial cells within the cardiac tissues can also express platelet-derived growth factor B after administration of the endothelial precursor cells and/or the young bone marrow cells. Such endothelial precursor cells and young bone marrow cells provide sustained delivery of platelet-derived growth factor B.

Administration of these cells can be intravascular, intravenous, intraarterial, intraperitoneal, via intraventricular infusion, via infusion catheter, via balloon catheter, via bolus injection, or via direct application to cardiac tissue during surgery. Administration can also be local or intravenous.

The endothelial precursor cells are derived from autologous bone marrow, peripheral blood, umbilical cord blood, organs, tissue, or fat. Such endothelial precursor cells or young bone marrow cells can also be cultured in the presence of platelet derived growth factor AB prior to administration. Endothelial precursor cells are also derived from allogeneic and xenogenic bone marrow, peripheral blood, umbilical cord blood, organs, tissues or fat. They are also derived from primitive precursor stem cells including but not limited to allogeneic biparental and parthenogenetic embryonic stem cells obtained by nuclear transfer and related technologies for reprogramming somatic cells to and embryonic state.

The cardiac tissues treated can be within a senescent heart. The mammal treated may have suffered from cardiovascular disease such as atherosclerosis, myocardial infarction, ischemia, tachycardia, or congestive heart failure.

DESCRIPTION OF THE FIGURES

FIG. 1A provides a photograph of a gel illustrating an RT-PCR analysis of PDGF-A, PDGF-B, and $\beta$-actin expression in ventricular myocardial samples isolated from young adult (3 month) and senescent mice (18 month).

FIG. 1B provides a photograph of a gel illustrating the expression profile of CMECs from 3- and 18-month-old mice co-cultured in transwells with fetal cardiac myocytes for zero to 3 days.

FIG. 1C provides a graph illustrating the fold-change in protein levels of CMECs from 3-month-old and 18-month-old mice cultured in the presence vs. the absence of fetal cardiac myocytes for 3 days.

FIG. 2A provides representative examples of neonatal cardiac transplants into young adult (3 months old) (n=20) and senescent hosts (18 months old) (n=17). Senescent hosts were also transplanted with silicon (n=8), neonatal lungs (n=8), and neonatal hearts after pinnal pretreatnient by injection of 100 ng of VEGF (n=12) or 100 ng of PDGF-AB (n=13). An arrow indicates viable/intact transplants. The majority of the cardiac allografts transplanted into the control and VEGF pretreated senescent mice resulted in a necrotic loss of both allograft and host pinnal tissue beyond the transplant site (arrowhead). Allograft viability was scored by pinnal and transplant integrity. Cardiac allograft viability in young adult and PDGF-AB-pretreated senescent hosts was confirmed by pinnal electrocardiograms (5-s tracing). *$P<0.01$ versus young adult; **$P<0.01$ versus senescent adult and $P<0.01$ versus senescent adult treated with VEGF.

FIG. 4A provides representative photographs of Masson's trichrome stained sections of 4-month-old rat hearts pretreated with PBS or PDGF-AB for 24 h before LAD ligation.

FIG. 4B provides a graph showing the myocardial infarct size scored 14 days after coronary artery ligation (control, n=13; PDGF-AB, n=12). *$P<0.02$, PDGF vs. control.

FIG. 4C provides representative photographs of Masson's trichrome staining in 24-month-old rat hearts pretreated with PBS or PDGF-AB 24 h before LAD ligation.

FIG. 4D provides a graph showing myocardial infarct size 14 days after coronary ligation (control, n=5; PDGF-AB, n=7). *$P<0.03$, PDGF vs. control.

DETAILED DESCRIPTION OF THE INVENTION

Figure 2B:
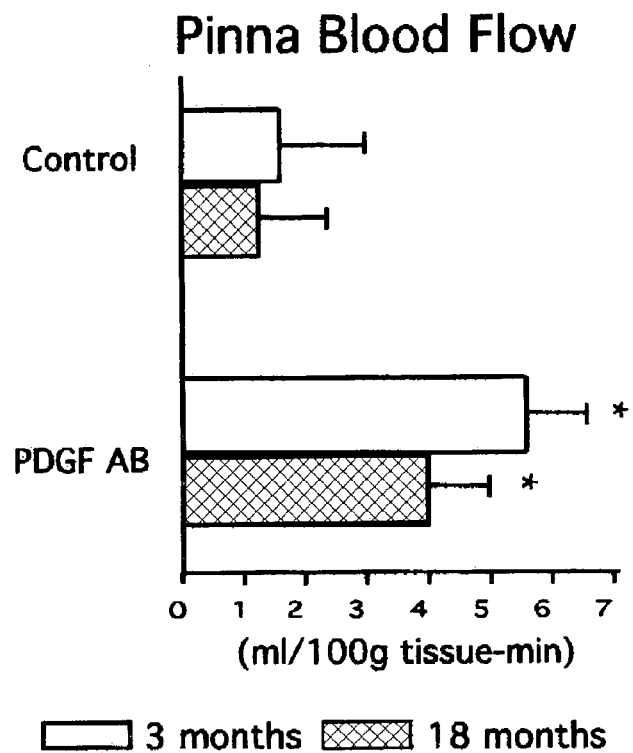
FIG. 2B provides a bar graph illustrating pinnae blood in ml/100 g tissue/min in untreated tissues and in tissues treated with PDGF AB. These results were obtained by laser Doppler measurements of capillary blood flow in the posterior auricular circulation. Pretreatment with PDGF AB significantly increased blood flow in both the young (3 month) as well as the older (18 month) hosts.

The present invention provides pharmaceutical compositions comprising an effective amount of endothelial precursor cells, for example, stem cells, embryonic endothelial cells, embryonic stem cell lines, hematopoietic stem cells, young adult bone marrow cells or older bone marrow cells that have been treated with platelet derived growth factor. The invention is also directed to methods for treating a vascular condition or a vascular disease in a mammal that include administering an effective amount of endothelial precursor cells, for example, endothelial precursor cells that express c-kit or platelet derived growth factor B. Such cells can be administered alone or in combination with platelet-derived growth factor AB (PDGF AB). Moreover, the cells can be genetically engineered to express useful gene products that can further enhance restoration and health of aging vascular tissues.

According to the invention, young endothelial precursor cells home to sites of angiogenesis in aging mammalian vessels. The ability of the young bone marrow to augment the population of aging bone marrow is illustrated by experiments described herein where LacZ+, Rosa-26 bone marrow was transplanted intravenously into intact isogeneic older mice 1 week before inducing cardiac angiogenesis. Analysis of these mice revealed that the genetically marked bone marrow ($\beta$-galactosidase-positive) cells were recruited to and engrafted within the senescent bone marrow. Hence, transplanted endothelial precursor cells become available to facilitate angiogenesis.

Moreover, further experiments described illustrate that while cardiac allografts transplanted into older mice did not become vascularized, transplantation of young bone marrow cells into old mice restored the vascularization and function of such exogenous cardiac tissue. Similar experiments where the bone marrow of old mice was transplanted failed to reverse the aging-associated decline in cardiac angiogenic function. The restoration of the senescent vascular function by the young bone marrow cells was dose-dependent in that greater numbers of young bone marrow cells improved the functioning of older vascular tissues.

In another embodiment, the invention provides pharmaceutical compositions of bone marrow cells that have been treated with PDGF. According to the invention, while bone marrow from senescent mammals fails to generate cardiac myocytes, exposure to PDGF AB restores the ability of such older bone marrow cells to generate myocytes. Such older bone marrow cells can thus be removed from a patient suffering, or in danger of suffering, from a vascular disease, the bone marrow cells can be cultured with platelet derived growth factor and then these cultured cells can be introduced back into the patient to treat or prevent the vascular disease. During this process, these bone marrow cells can also be genetically engineered to express useful gene products that can further enhance restoration and health of aging vascular tissues, particularly within the heart.

Hence, the invention provides compositions comprising cells capable of improving the function of older vascular tissues and methods for treating a variety of vascular diseases. In some embodiments, the compositions and methods of the invention promote angiogenesis and/or re-endothelialization. As used herein, angiogenesis is a process in which endothelial cells form a vascular bed to provide blood to organs through the body, including the heart. Re-endothelialization refers to the homing of circulating endothelial precursor cells to sites of intimal injury such as occurs in atherosclerotic plaques.

Vascular Diseases

The vascular diseases treated by the present invention are vascular diseases of mammals. The word mammal means any mammal. Some examples of mammals include, for example, pet animals, such as dogs and cats; farm animals, such as pigs, cattle, sheep, and goats; laboratory animals, such as mice and rats; primates, such as monkeys, apes, and chimpanzees; and humans. In some embodiments, humans are preferably treated by the methods of the invention.

According to the invention, endothelial cells within normal vascular tissues change as they grow older, exhibiting reduced angiogenesis, reduced capacity for re-endothelization and losing their ability to communicate with other cells by secreting signaling agents. These changes can lead to a diminished capacity for blood vessel formation, a reduction in blood flow to the associated organ or system, and an inability to recover from injuries or diseases that adversely affect blood vessels.

Accordingly, the invention relates to methods for treating endothelial dysfunction, or a vascular condition, or a circulatory condition, such as a condition associated with loss, injury or disruption of the vasculature within an anatomical site or system. The term "vascular condition" or "vascular disease" refers to a state of vascular tissue where blood flow is, or can become, impaired.

Many pathological conditions can lead to vascular diseases that are associated with alterations in the normal vascular condition of the affected tissues and/or systems. Examples of vascular conditions or vascular diseases to which the methods of the invention apply are those in which the vasculature of the affected tissue or system is senescent or otherwise altered in some way such that blood flow to the tissue or system is reduced or in danger of being reduced. Examples of vascular conditions that can be treated with the compositions and methods of the invention include atherosclerosis, preeclampsia, peripheral vascular disease, erectile dysfunction, cancers, renal failure, heart disease, and stroke. Vascular, circulatory or hypoxic conditions to which the methods of the invention apply also include those associated with, but not limited to, maternal hypoxia (e.g., placental hypoxia, preeclampsia), abnormal pregnancy, peripheral vascular disease (e.g., arteriosclerosis), transplant accelerated arteriosclerosis, deep vein thrombosis, erectile dysfunction, cancers, renal failure, stroke, heart disease, sleep apnea, hypoxia during sleep, female sexual dysfunction, fetal hypoxia, smoking, anemia, hypovolemia, vascular or circulatory conditions which increase risk of metastasis or tumor progression, hemorrhage, hypertension, diabetes, vasculopathologies, surgery (e.g., per-surgical hypoxia, post-operative hypoxia), Raynaud's disease, endothelial dysfunction, regional perfusion deficits (e.g., limb, gut, renal ischemia), myocardial infarction, stroke, thrombosis, frost bite, decubitus ulcers, asphyxiation, poisoning (e.g., carbon monoxide, heavy metal), altitude sickness, pulmonary hypertension, sudden infant death syndrome (SIDS), asthma, chronic obstructive pulmonary disease (COPD), congenital circulatory abnormalities (e.g., Tetralogy of Fallot) and Erythroblastosis (blue baby syndrome). In particular embodiments, the invention is a method of treating loss of circulation or endothelial dysfunction in an individual.

Thus, the invention is directed to methods of treating diseases such as stroke, atherosclerosis, acute coronary syndromes including unstable angina, thrombosis and myocardial infarction, plaque rupture, both primary and secondary (in-stent) restenosis in coronary or peripheral arteries, transplantation-induced sclerosis, peripheral limb disease, intermittent claudication and diabetic complications (including ischemic heart disease, peripheral artery disease, congestive heart failure, retinopathy, neuropathy and nephropathy), or thrombosis.

In some embodiments, the vascular condition or vascular disease arises from damaged myocardium. As used herein "damaged myocardium" refers to myocardial cells that have been exposed to ischemic conditions. These ischemic conditions may be caused by a myocardial infarction, or other cardiovascular disease. The lack of oxygen causes the death of the cells in the surrounding area, leaving an infarct that can eventually scar.

Preferably, damaged myocardium is treated with the methods and compositions of the invention before damage occurs (e.g. when damage is suspected of occurring) or as quickly as possible after damage occurs. Hence, the methods and compositions of the invention are advantageously employed on aged heart tissues that are in danger of ischemia, heart attack or loss of blood flow. The methods and compositions of the invention are also advantageously employed on recently damaged myocardium and on not so recently damaged myocardium.

As used herein "recently damaged myocardium" refers to myocardium that has been damaged within one week of treatment being started. In a preferred embodiment, the myocardium has been damaged within three days of the start of treatment. In a further preferred embodiment, the myocardium has been damaged within twelve hours of the start of treatment.

The methods and compositions of the invention can be used to prevent or to treat these vascular conditions. These methods involve administering an effective amount of endothelial precursor cells, for example, stem cells, young bone marrow cells, hematopoietic stem cells, embryonic stem cell lines or young cardiac microvascular endothelial cells. Such cells can be administered alone or in combination with platelet-derived growth factor (PDGF). Such an effective amount is effective when it stimulates the generation of myocytes or restores some vascularization in a tissue.

Isolating Endothelial Precursor Cells

According to the invention, endothelial precursor cells, hematopoietic stem cells, erythropoietic stem cells and other types of stem cells can reverse age-related defects in cardiac angiogenesis. As used herein, the term "endothelial precursor cells" includes all types of cells that can promote neogenesis or angiogenesis of vascular tissues. Examples include endothelial precursor cells, endothelial cell precursors, hematopoietic stem cells, embryonic stem cell lines, erythropoietic stem cells, young bone marrow cells, young cardiac microvascular endothelial cells and other types of stem cells. Such endothelial precursor cells are capable of populating the intact, senescent bone marrow, homing to sites of cardiac angiogenic induction, restoring pathways required for vascular function, homing to sites of intimal injury and facilitating re-endothelialization. These cells can restore and stimulate cardiac angiogenesis in an aging host, for example, by healing injured vascular tissues, reducing the size of atherosclerotic lesions, stimulating angiogenesis, generating cardiac myocytes and promoting formation of new blood vessels and new endothelial tissues.

The endothelial precursor cells employed in the invention can be stem cells or partially differentiated endothelial precursor cells. The term endothelial cell precursors is used interchangeably herein with endothelial precursor cells. Because endothelial cell precursors are present in circulating blood, they are also referred to as circulating endothelial precursor cells (see U.S. Patent Application No. 60/349,345, filed Jan. 22, 2002, now abandoned, the priority of which is claimed, and Lyden et al., 2002, supra). Such stem cells and endothelial precursor cells can be derived from nuclear transfer-derived embryonic cells from pre-implantation embryos, from in vitro fertilized embryos, parthenogenetic embryos or aborted fetuses, from young adult bone marrow-derived cells, and/or from adult stem cells.

Pluripotent stem cells are capable of developing into more than two types of mature cells, such as endothelial cells, hematopoietic cells, and at least one other type of cells. Bipotent stem cells are capable of developing into two types of mature cells, such as endothelial cells and hematopoietic cells. Progenitor cells are capable of developing into one type of mature cells, such as endothelial cells or hematopoietic cells. Pluripotent stem cells, bipotent stem cells, and progenitor cells are capable of developing into mature cells either directly, or indirectly through one or more intermediate stem or progenitor cell. An endothelial stem cell is a stem cell that is capable of maturing into at least one type of mature endothelial cell. The endothelial stem cell may be pluripotent, bipotent, or monopotent. Monopotent endothelial stem cells are also referred to as endothelial progenitor cells Pluripotent endothelial stem cells are capable of developing into mature endothelial cells and at least two other types of cells. Bipotent endothelial stem cells are capable of developing into mature endothelial cells and one other type of cells, such as hematopoietic cells. Monopotent endothelial cells, i.e. endothelial progenitor cells, are capable of developing into mature endothelial cells.

According to the invention, the term endothelial precursor cells always includes progenitor cells that can differentiate into endothelial precursor cells and/or endothelial cells. Hence, any population of stem cells (pluripotent, bipotent, monopotent, etc.) or precursor cell types can be used in the invention so long as they can generate endothelial cells. Thus, hematopoietic stem cells differentiate to form endothelial cell precursors, and endothelial cell precursors give rise to endothelial cells.

Hematopoietic stem cells and endothelial cell precursors can be isolated directly from bone marrow, fetal liver, circulating peripheral blood, and autologous umbilical cord blood. The leukocyte fraction of peripheral blood is a useful source of endothelial cell precursors. In addition, endothelial cell precursors can be produced in vitro or in vivo through the differentiation of hematopoietic stem cells. For example, in addition to giving rise to cells such as B and T lymphocytes, granulocytes, and monocytes, hematopoietic stem cells isolated from adult human bone marrow also differentiate into non-hematopoietic lineages (lin$^-$) that give rise to endothelial cell precursors (Otani et al., Nature Medicine, 2002, 8(9): 1004–1010).

Endothelial precursor cells can be identified by their surface antigens and/or by the factors they express. Such antigens include, for example, one or more vascular endothelial growth factor receptors (VEGFR). Examples of VEGFRs include FLK-1 and FLT-1. The FLK-1 receptor is also known by other names, such as VEGFR-2. Human FLK-1 is sometimes referred to in the literature and herein as KDR. Bone-marrow reconstituting hematopoietic stem cells and endothelial cell precursors both have the CD-34 antigenic determinant (U.S. Pat. No. 5,980,887, supra.) and express vascular endothelial growth factor receptor-1 (VEGFR-1) (Lyden et al., 2001, supra.). Endothelial cell precursors and vascularizing endothelial cells both express vascular endothelial growth factor receptor-2 (VEGFR-2) (Neithammer et al., 2002, supra.).

At least some endothelial precursor cells also express the CD34+ marker. The endothelial precursor cells may be further characterized by the absence or significantly lower expression levels of certain markers characteristic of mature cells. Such markers include CD1, CD3, CD8, CD10, CD13, CD14, CD15, CDT 9, CD20, CD33, and CD41A.

In addition, at least some endothelial precursor cells also express the AC133 antigen, which was described by Yin et al. in Blood 90, 5002–5112 (1997), Peicbev et al., Blood, 2000, 95(3):952–958 and by Miraglia et al. in Blood 90, 5013–5021 (1997). The AC133 antigen is expressed on endothelial and hematopoietic precursor cells, but not on mature cells.

Most, if not all, of the endothelial precursor cells express FLK-1. The CD34 marker is characteristic of precursor cells, such as angioblasts and hematopoietic precursor cells. Approximately 0.5–10% of CD34+ cells are also FLK-1+. For example, approximately 1% of bone marrow cells are CD34+. Of these, approximately 1% are FLK-1+.

High levels of c-kit RNA transcripts are found in primary bone marrow derived mast cells and mast cell lines, while somewhat lower levels are found in melanocytes and erythroid cell lines. Hence c-kit expression is another marker for endothelial precursor cells. The c-kit proto-oncogene encodes a transmembrane tyrosine kinase receptor for an unidentified ligand and is a member of the colony stimulating factor-1 (CSF-1)—platelet-derived growth factor (PDGF)—kit receptor subfamily (Besmer et al., (1986) Nature 320, 415–421; Qiu et al., (1988) EMBO J. 7, 1003–1011; Yarden et al., (1987) EMBO J. 6, 3341–3351; Majumder, S., Brown, K., Qiu, F. -H. and Besmer, P. (1988) Mol. Cell. Biol. 8, 4896–4903). c-kit is allelic with the white-spotting (W) locus of the mouse. Mutations at the W locus affect proliferation and/or migration and differentiation of germ cells, pigment cells and distinct cell populations of the hematopoietic system during development and in adult life. The W locus effects hematopoiesis through the erythroid lineages, mast cell lineages and stem cells, resulting in a macrocytic anemia which is lethal for homozygotes of the most severe W alleles, and a complete absence of connective tissue and mucosal mast cells.

A population of endothelial precursor cells can be isolated from mixed cell sources such as bone marrow. The source of cells from which isolated endothelial precursor cells are derived may be any natural or non-natural mixture of cells that contain endothelial precursor cells. The source may be derived from an embryo, or from the post-natal mammal. Preferably, the source of cells is the hematopoietic microenvironment, such as the circulating peripheral blood, preferably from the mononuclear fraction of peripheral blood, umbilical cord blood, bone marrow, fetal liver, or yolk sac of a mammal. The source of cells therefore need not be embryonic or fetal.

Isolated cells are not necessarily pure cells; instead, isolated cells are removed from their natural source, environment or from the mammal where they naturally arose. Isolated cells can also be obtained from in vitro cultures of cell lines or from cultured embryonic cells. Endothelial precursor calls can be purified from a mixed population cells, such as bone marrow cells, by extracting them or removing them from the bone marrow. However, no such purification is needed so long as no adverse immunological reaction will occur upon administration to a mammal. The term purified as applied to the endothelial precursor cell population utilized herein means that the population is significantly enriched in endothelial precursor cells relative to the crude population of cells from which the endothelial precursor cells are isolated.

Bone-marrow reconstituting hematopoietic stem cells and endothelial cell precursors can be purified, for example, from preparations of bone marrow, fetal liver, circulating blood, or from in vitro-derived cells, such as those derived from allogeneic embryonic cells, nuclear transfer-derived stem cells and parthenogenetically-derived stem cells. Any available method can be used for such purification. Methods that can be employed include, for example, fluorescence-activated cell sorting (FACS) or immunomagnetic separation (for example, see Peichev et al., Blood, 2000, 95(3): 952–958); and Otani et al., Nature Medicine, 2002, 8(9): 1004–1010, the contents of both of which are incorporated herein by reference in their entirety). For example, the purification procedure can lead at least to a two-fold, three-fold, five-fold, ten-fold, fifteen-fold, twenty-fold, or twenty-five fold increase in endothelial precursor cells over the total population. The purified population of endothelial precursor cells can contain at least 15%, at least 20%, at least 25%, at least 35%, or at least 50% of endothelial precursor cells.

The methods of the invention can also utilize cellular mixtures comprising 30%, 50%, 75%, 80%, 85%, 90% or 95% of endothelial precursor cells. The methods of the invention can also utilize cell mixtures comprising 99%, 99.9% and even 100% of endothelial precursor cells. Accordingly, cell populations utilized in the invention contain significantly higher levels of endothelial precursor cells than those that exist in nature.

Endothelial precursor cells can be identified by observing their expression patterns or by contacting the cells with a molecule that binds specifically to the extracellular portion of an antigen specific for endothelial precursor cells. The binding of the endothelial precursor cells to the molecule permits the endothelial precursor cells to be sufficiently distinguished from contaminating cells that do not express the antigen to permit identification of the endothelial precursor cells from the contaminating cells.

The cells can also be purified by genetic selection techniques available in the art. For example, a nucleic acid encoding resistance to an antibiotic (such as the neomycin) can be operably linked to a nucleic acid encoding a promoter that is specifically active in an endothelial precursor (such as a KDR promoter) to generate an expression cassette. The expression cassette can then be transfected into embryonic stem cells and the embryonic stem cells can be used to generate endothelial precursor cells that can express the neomycin resistance function. Cells that do not differentiate into endothelial precursor cells sill not be resistant to neomycin because the promoter will not be active in those cells.

The molecule used to identify endothelial precursor cells can also be used separate endothelial precursor cells from the contaminating cells. Such a molecule can be any molecule that is specifically expressed within the endothelial precursor cells or that binds specifically to an antigen that characterizes the endothelial precursor cell. The molecule can be, for example, a monoclonal antibody, a fragment of a monoclonal antibody, or, in the case of an antigen that is a receptor, the ligand of that receptor. For example, in the case of a VEGF receptor, such as FLK-1, the ligand is VEGF. Other molecules that can be used to identify and separate endothelial precursor cells from other cells include PDGF alpha receptor, VEGF-1 receptor, VEGF-2 receptor, VEGF-3 receptor, VEGF A, VEGF B, VEGF C, VEGF D, VEGF E, EGF, EGF receptor; tumor necrosis factor alpha and tumor necrosis factor receptor, and peptides discovered by phage display to specifically bind to such cells.

Either before or after the crude cell populations are purified as described above, the cells may be further enriched in precursor cells by methods known in the art. For example, human endothelial precursor cells may be pre-purified or post-purified by means of an anti-CD34 antibody, such as the anti-My-10 monoclonal antibody described by Civin in U.S. Pat. No. 5,130,144. The hybridoma cell line that expresses the anti-My monoclonal antibody is available from the American Type Culture Collection, 12301 Parklawn Drive, Rockville, Md. 20852, USA. Some additional sources of antibodies capable of selecting CD34+cells include AMAC, Westbrook, Me.; Coulter, Hialea, Fla.; and Becton Dickinson, Mountain View, Calif. CD34+ cells may also be isolated by means of comparable antibodies, which may be produced by methods known in the art, such as those described by Civin in U.S. Pat. No. 5,130,144.

In addition, or as an alternative to, the enrichment with anti-CD34 antibodies, populations of endothelial precursor cells may also be further enriched with the AC133 antibodies described by Yin et al. in Blood 90, 5002–5112 (1997) and by Miraglia et al. in Blood 90, 5013–5021 (1997). The AC133 antibodies may be prepared in accordance with Yin et al., ibid, or purchased from Miltenyi Biotec. Hence, the preferred cells of the invention express PDGF B. Such cells may also express FLK-1, CD34, or AC133.

Suitable mixtures of cells from a hematopoietic microenvironment may be harvested from a mammalian donor or from an in vitro culture by methods known in the art. For example, precursor endothelial cells may be isolated from bone marrow or from circulating peripheral blood or cells can be differentiated in vitro from a primitive stem cell. Endothelial precursor cells are mobilized (i.e., recruited) into the circulating peripheral blood by means of cytokines, such as, for example, G-CSF, GM-CSF, VEGF, SCF (c-kit ligand) and bFGF, chemokines, such as SDF-1, or interleukins, such as interleukins 1 and 8. Hence, endothelial precursor cells can be isolated from blood after recruiting those cells from bone marrow by pre-treatment with one or more of these cytokines. Alternatively, bone marrow may be obtained from a mammal, such as a human patient who will undergo autologous transplantation of the collected cells.

The endothelial precursor cells can be identified within the mixture of cells obtained by exposing the cells to a molecule that binds specifically to the antigen marker characteristic of endothelial precursor cells. The molecule is preferably an antibody or a fragment of an antibody. A convenient antigen marker is PDGF, or a VEGF receptor, for example, a FLK-1 receptor. The cells that express the antigen marker bind to the molecule. The molecule distinguishes the bound cells from unbound cells, permitting separation and isolation. If the bound cells do not internalize the molecule, the molecule may be separated from the cell by methods known in the art. For example, antibodies may be separated from cells with a protease such as chymotrypsin.

The molecule used for isolating the purified populations of endothelial precursor cells is advantageously conjugated with labels that expedite identification and separation. Examples of such labels include magnetic beads, biotin, which may be removed by avidin or streptavidin, fluorochromes, which may be used in connection with a fluorescence-activated cell sorter, and the like.

Any technique may be used for isolation as long as the technique does not unduly harm the endothelial precursor cells. Many such methods are known in the art.

In one embodiment, the molecule is attached to a solid support. Some suitable solid supports include nitrocellulose, agarose beads, polystyrene beads, hollow fiber membranes, and plastic petri dishes. For example, the molecule can be covalently linked to Pharmacia Sepharose 6MB macro beads. The exact conditions and duration of incubation for the solid phase-linked molecules with the crude cell mixture will depend upon several factors specific to the system employed, as is well known in the art. Cells that are bound to the molecule are removed from the cell suspension by physically separating the solid support from the cell suspension. For example, the unbound cells may be eluted or washed away with physiologic buffer after allowing sufficient time for the solid support to bind the endothelial stem cells.

The bound cells are separated from the solid phase by any appropriate method, depending mainly upon the nature of the solid phase and the molecule. For example, bound cells can be eluted from a plastic petri dish by vigorous agitation. Alternatively, bound cells can be eluted by enzymatically "nicking" or digesting an enzyme-sensitive "spacer" sequence between the solid phase and an antibody. Suitable spacer sequences bound to agarose beads are commercially available, for example, from Pharmacia.

The eluted, enriched fraction of cells may then be washed with a buffer by centrifugation and preserved in a viable state at low temperatures for later use according to conventional technology. The cells may also be used immediately, for example by being infused intravenously into a recipient.

In a desirable variation of the method described above, blood is withdrawn directly from the circulating peripheral blood of a donor. The blood is percolated continuously through a column containing the solid phase-linked molecule to remove endothelial precursor cells. The precursor cell-depleted blood is returned immediately to the donor's circulatory system by methods known in the art, such as hemapheresis. The blood is processed in this way until a sufficient number of precursor cells binds to the column. This method allows rare peripheral blood precursor cells to be harvested from a very large volume of blood, sparing the donor the expense and pain of harvesting bone marrow and the associated risks of anesthesia, analgesia, blood transfusion, and infection.

Other methods for isolating the purified populations of endothelial precursor cells are also known. Such methods include magnetic separation with antibody-coated magnetic beads, and "panning" with an antibody attached to a solid matrix. Methods for isolating the purified populations of endothelial precursor cells include general fluorescence activated cell sorting (FACS) protocols. In one embodiment, a labeled molecule is bound to the endothelial precursor cells, and the labeled cells are separated by a mechanical cell sorter that detects the presence of the label. The mechanical cell sorter is a florescence activated cell sorter (FACS) that is commercially available. Generally, the following FACS protocol is suitable for this procedure:

A Coulter Epics Eliter sorter is sterilized by running 70% ethanol through the systems. The lines are flushed with sterile distilled water.

Cells are incubated with a primary antibody diluted in Hank's balanced salt solution supplemented with 1% bovine serum albumin (HB) for 60 minutes on ice. The cells are washed with HB and incubated with a secondary antibody labeled with fluorescein isothiocyanate (FITC) for 30 minutes on ice. The secondary label binds to the primary antibody. The sorting parameters, such as baseline fluorescence, are determined with an irrelevant primary antibody. The final cell concentration is usually set at one million cells per ml.

While the cells are being labeled, a sort matrix is determined using fluorescent beads as a means of aligning the instrument.

Once the appropriate parameters are determined, the cells are sorted and collected in sterile tubes containing medium supplemented with fetal bovine serum and antibiotics, usually penicillin, streptomycin and/or gentamicin. After sorting, the cells are re-analyzed on the FACS to determine the purity of the sort.

In another embodiment, the invention is directed to isolated populations of precursor cells that express a suitable marker, for example, PDGF B or a VEGF receptor, such as, for example, the FLK-1 receptor. This embodiment further includes isolation of purified populations of such cells. The PDGF B+ precursor cells include, for example, endothelial precursor cells. The source of cells from which the precursor cells are obtained include both pre-natal and post-natal sources. Post-natal sources are preferred.

Generating Endothelial Precursor Cells

In addition to providing methods for isolating endothelial precursor cells, the invention provides methods for producing such cells. Hematopoietic stem cells (HSCs) and endothelial cell precursors (ECPs) produced in this manner can be genetically modified to express a useful gene product, for example, a gene product that augments repair of vascular injury or disease, or a gene product that prevents development of vascular disease. The hematopoietic stem cells and endothelial cell precursors can home to vascular tissues and provide angiogenesis (for example, in the coronary arteries of the heart), thereby restoring vascular tissues that have been injured or have become diseased.

In one embodiment of the present invention, hematopoictic stem cells and endothelial cell precursors are isolated from a human or a non-human mammal by available methods, for example, as described above in the previous section. These cells can be genetically modified in vitro to contain a genomically integrated DNA expression construct encoding a gene that confers therapeutic effect when it is expressed by endothelial cells in the heart or arteries affected with a vascular disease such as atherosclerosis.

In an alternative embodiment of the invention, healthy somatic cells are isolated from a human or a non-human mammal and used for generating totipotent or pluripotent embryo-derived stem cells (e.g., embryonic stem cells). In this embodiment, the nucleic from these somatic cells are inserted into an enucleated oocyte by available procedures to generate a nuclear transfer unit that is stimulated to divide, thereby generating totipotent or pluripotent embryo-derived stem cells. The totipotent or pluripotent embryo-derived stem cells can be induced to differentiate into hematopoietic stem cells, which in turn can differentiate to generate genetically modified endothelial cell precursors of the invention. Prior to nuclear transfer, the somatic cell can be genetically modified to contain a gene that confers a therapeutic effect when expressed by endothelial cells, or alternatively, such modifications can be introduced in the resulting stem cells.

All types of somatic cells can be utilized as donor cells for this purpose. For example, the donor cell or donor cell nucleus can be selected from the group consisting of epithelial cells, neural cells, epidermal cells, keratinocytes, hematopoietic cells, melanocytes, chondrocytes, lymphocytes, erythrocytes, macrophages, monocytes, mononuclear cells, fibroblasts, muscle cells, skin cells, lung cells, pancreatic cells, liver cells, stomach cells, intestinal cells, heart cells, bladder cells, reproductive organ cells, urethra cell, and kidney cells.

The hematopoietic stem cells and endothelial cell precursors, whether genetically modified or not, are then administered to a patient with a vascular disease, whereupon the hematopoietic stem cells or endothelial cell precursors home to sites of vascular injury or areas of ischemic injury (see, for example, Asahara et al., 1997, "Isolation of putative progenitor endothelial cells for angiogenesis," Science 275: 964–967, the contents of which are incorporated herein by reference). After reaching the site of vascular injury the hematopoietic stem cells and/or endothelial cell precursors help to prevent or repair vascular disease or vascular injury. Expression of a transgene can further enhance the therapeutic effect of these cells.

Advanced Cell Technology, Inc. and other groups have developed methods for transferring the genetic information in the nucleus of a somatic or germ cell from a child or adult into an unfertilized egg cell, and culturing the resulting cell to divide and form a blastocyst embryo having the genotype of the somatic or germ nuclear donor cell. Methods for cloning by such methods are referred to as cloning by "somatic cell nuclear transfer," because somatic donor cells are commonly used. Methods for cloning by nuclear transfer are available, and are described, for example, in U.S. Pat. No. 6,235,970 (Stice et al.) and U.S. Pat. No. 6,147,276 (Campbell et al.), and in U.S. Pat. Nos. 5,994,619 and 6,235,969 of Stice et al., the contents of all three are incorporated herein by reference in their entirety.

Methods for human therapeutic cloning have been described. For example, methods that use nuclear transfer cloning to produce cells and tissues for transplant therapies that are histocompatible with the transplant recipient are described in U.S. application Ser. No. 09/797,684 filed Mar. 5, 2001 now abandoned. This application also discloses assay methods for determining the immune-compatibility of cells and tissues for transplant the contents of which are incorporated herein by reference in their entirety. Similar methods are also described in U.S. application Ser. No. 10/227,282 ("Screening Assays for Identifying Differentiation-Inducing Agents and Production of Differentiated Cells for Cell Therapy"), filed Aug. 26, 2002, the contents of which are also incorporated herein by reference in their entirety, which further discloses screening methods that make use of gene trapped cell lines and provide means for efficiently identifying combinations of biological, biochemical, and physical agents or conditions that induce stem cells to differentiate into cell types useful for transplant therapy. Methods for producing totipotent and pluripotent stem cells are also described in U.S. application Ser. No. 09/995,659 filed Nov. 29, 2001, now abandoned, and International Application No. PCT/US02/22857 filed Jul. 18, 2002, which further describe methods for producing histocompatible cells and tissues for transplant by androgenesis and gynogenesis; and in U.S. application Ser. No. 09/520,879 filed Apr. 5, 2000, now abandoned, which discloses methods for producing "rejuvenated" or "hyper-young" cells having increased proliferative potential relative to cells of the donor animal. A method for obtaining totipotent and pluripotent stem cells from embryos generated by parthenogenesis is also reported by Cibelli et al., who describe the isolation of a non-human primate stem cell line from the inner cell mass of parthenogenetic Cynomologous monkey embryos that is capable of differentiating into cell types of all three embryonic germ layers (see Science (2002) 295:819, the contents of which are incorporated herein by reference in their entirety.) The disclosures of all of the above-listed patent applications are also incorporated herein by reference in their entirety.

A general procedure for cloning by fusion of a somatic cell is provided below. The procedure is meant to be exemplary. Many variations and modifications can be made to such a procedure by one of skill in the art without deviating from the invention.

In general, oocytes are isolated from the ovaries or reproductive tract of a human or non-human mammal, matured in vitro, and stripped of cumulus cells to prepare for nuclear transfer. Removal of the endogenous chromosomes of the oocyte is referred to as "enucleation." Enucleation of the recipient oocyte is performed after the oocyte has attained the metaphase II stage, and can be carried out before or after nuclear transfer. Enucleation can be confirmed by visualizing chromosomal DNA in TL-HEPES medium plus Hoechst 33342 (3 μg/ml; Sigma).

Individual donor cells are placed in the perivitelline space of the recipient enucleated oocyte, and the oocyte and donor cell are fused together to form a single cell (nuclear transfer unit) e.g., by electrofusion. The nuclear transfer units are activated, and are incubated in suitable medium under conditions that promote growth of the nuclear transfer unit. During this period of incubation, the nuclear transfer units can be transferred to culture plates containing a confluent feeder layer. Feeder layers of various cell types from various species, e.g., irradiated mouse embryonic fibroblasts, that are suitable for the invention are described, for example, in U.S. Pat. No. 5,945,577, the contents of which are incorporated herein by reference in their entirety.

Genetically modified nuclei can be generated and fused with enucleated oocytes as follows. Primary cultures of somatic cells are isolated and grown in vitro using available methods. Such methods are described, for example, in U.S.

Pat. No. 6,011,197 (Strelchenko et al.), and in U.S. Pat. No. 5,945,577 (Stice et al.), the contents of both of which are incorporated herein by reference in their entirety.

The somatic donor cell used for nuclear transfer to produce a nuclear transplant unit or embryo according to the present invention can be of any germ cell or somatic cell type in the body. For example, the donor cell can be a germ cell, or a somatic cell selected from the group consisting of fibroblasts, B cells, T cells, dendritic cells, keratinocytes, adipose cells, epithelial cells, epidermal cells, chondrocytes, cumulus cells, neural cells, glial cells, astrocytes, cardiac cells, esophageal cells, muscle cells, melanocytes, hematopoietic cells, macrophages, monocytes, and mononuclear cells. The donor cell can be obtained from any organ or tissue in the body; for example, it can be a cell from an organ selected from the group consisting of liver, stomach, intestines, lung, stomach, intestines, lung, pancreas, cornea, skin, gallbladder, ovary, testes, vasculature, brain, kidneys, urethra, bladder, and heart, or any other organ.

A general procedure for isolating primary cultures of fibroblast cells is as follows: Minced tissue is incubated overnight at 10° C. in trypsin, cells are washed and then are plated in tissue culture dishes and cultured in alpha-MEM medium (BioWhittaker, Walkersville, Md.) supplemented with 10% fetal calf serum (FCS) (Hyclone, Logen, Utah), penicillin (100 IU/ml) and streptomycin (50 µl/ml). The fibroblast cells can be isolated at virtually any time in development, ranging from approximately post embryonic disc stage through adult life of the animal (for example, for bovine, from day 12 to 15 after fertilization to 10 to 15 years of age).

A general procedure for stably introducing a genetic expression construct into the genomic DNA of the cultured fibroblasts by electroporation is described below. Other available transfection methods, such as microinjection or lipofection can also be used to introduce heterologous DNA into the cells.

Culture plates containing propagating fibroblast cells are incubated in trypsin EDTA solution (0.05% trypsin/0.02% EDTA; GIBCO, Grand Island, N.Y.) until the cells are in a single cell suspension. The cells are spun down at 500×g and re-suspended at a density of about 5 million cells per ml with phosphate buffered saline (PBS). A vector or nucleic acid construct containing the an expression cassette encoding the gene product of interest is added to the cells in the electroporation chamber. After providing a standard electroporation pulse, the fibroblast cells are transferred back into the growth medium (alpha-MEM medium (BioWhittaker, Walkersville, Md.) supplemented with 10% fetal calf serum (FCS) (Hyclone, Logen, Utah), penicillin (100 IU/ml) and streptomycin (50 µl/ml)).

The day after electroporation, attached fibroblast cells are selected for stable integration of the vector or nucleic acid construct by culturing them for up to 15 days in growth medium containing a selective agent that will select for cells having the vector or nucleic acid construct. At the end of the selection period, colonies of stable transgenic cells are present. Each colony is propagated independently of the others. Transgenic fibroblast cells can be further tested for expression of the gene product of interest, and genomic integration of the expression construct can be confirmed by available methods; e.g., by PCR amplification and analysis by agarose gel electrophoresis.

Stably transfected fibroblast cells are used as nuclear donors in the nuclear transfer (NT) procedure. Procedures for cloning by nuclear transfer are available in the art. For example, methods for cloning by somatic cell nuclear transfer are described in detail in U.S. Pat. No. 6,147,276 (Campbell et al.), and in co-owned and co-assigned U.S. Pat. Nos. 5,945,577 and 6,235,969 of Stice et al.

In general, oocytes are isolated from the ovaries or reproductive tract of a human or non-human mammal and are matured in vitro. The oocytes are stripped of cumulus cells to prepare for nuclear transfer. Enucleation of the recipient oocyte is performed after the oocyte has attained the metaphase II stage, and can be carried out before or after nuclear transfer. Individual donor cells (fibroblasts) are then placed in the perivitelline space of the recipient oocyte, and the oocyte and donor cell are fused together to form a single cell (an nuclear transfer unit) using electrofusion techniques; e.g., by applying a single one fusion pulse consisting of 120 V for 15 µsec to the nuclear transfer unit in a 500 µm gap chamber. The nuclear transfer units are then incubated in suitable medium.

A variety of different procedures for artificially activating oocytes are available and have been described. See U.S. application Ser. No. 09/467,076 (Cibelli et al.), filed Dec. 20, 1999, the contents of which are incorporated herein by reference in their entirety. Following activation, the nuclear transfer units are washed and cultured under conditions that promote growth of the nuclear transfer unit to have from 2 to about 400 cells. During this time, the nuclear transfer units can be transferred to well plates containing a confluent feeder layer; e.g., a feeder layer of mouse embryonic fibroblasts. Feeder layers of various cell types from various species that are suitable for the invention are described, for example, in U.S. Pat. No. 5,945,577. Multicellular non-human nuclear transfer units produced in this manner can be transferred into recipient non-human females of the same species as the donor nucleus and recipient oocyte, for development into transgenic non-human mammals. Alternatively, the nuclear transfer units can be incubated until they reach the blastocyst stage, and the inner cell mass (ICM) cells of these nuclear transfer units can be isolated and cultured in the presence or absence of a feeder layer to generate pluripotent or totipotent embryonic stem cells. These stem cells can then be differentiated to generate downstream cultured stem cells such as the mesodermal precursors to hemangioblasts.

Multicellular non-human nuclear transfer units produced in this manner can be transferred as embryos into recipient non-human females of the same species as the donor nucleus and recipient oocyte, for development into transgenic non-human mammals. Alternatively, the nuclear transfer units can be incubated in vitro until they reach the blastocyst stage, and the inner cell mass (ICM) cells of these nuclear transfer units can be isolated and cultured in the presence or absence of a feeder layer to generate pluripotent or totipotent embryo-derived stem cells, including totipotent embryonic stem cells.

Cellular Differentiation

Methods are available for isolating cells within the inner cell mass of a blastocyst produced by nuclear transfer, and culturing these to generate pluripotent and totipotent embryo-derived cell lines, including totipotent embryonic stem cell lines. For example, see U.S. Pat. Nos. 5,905,042 and 5,994,619 of Stice et al., the contents of both of which are incorporated herein by reference. Using available methods, totipotent and pluripotent stem cells derived from nuclear transfer-generated blastocysts, e.g., embryonic stem cells, can be cultured under conditions that direct or allow differentiation into a variety of partially and fully differentiated somatic cell types, including hematopoietic stem cells.

For example, see Wakayama et al., "Differentiation of embryonic stem cell lines generated from adult somatic cells by nuclear transfer, 2001, Science, 292:740–3; Talbot et al., "Spontaneous differentiation of porcine and bovine embryonic stem cells (epiblast) into astrocytes or neurons," 2002, In Vitro Cell Dev Biol Anim., 38(4):191–7; and Mitalipova et al., "Pluripotency of bovine embryonic cell line derived from precompacting embryos," 2001, Cloning, 3(2):59–67, the contents of all three of which are incorporated herein by reference. Methods for inducing the differentiation of pluripotent human blastocyst-derived embryonic stem cells into hematopoietic stem cells are also available (U.S. Pat. No. 6,280,718, Kaufman et al., "Hematopoietic differentiation of human pluripotent embryonic stem cells," the contents of which are incorporated herein by reference).

Accordingly, stem cells isolated or generated as described herein can readily be differentiated into endothelial precursor cells and hematopoietic stem cells.

Moreover, the invention provides methods for rejuvenating senescent cells that ordinarily would not be able to differentiate into other cell types, so that those senescent cells can give rise to therapeutically active cells. In particular, the invention provides a method of generating cardiac myocytes from senescent bone marrow cells that could not otherwise give rise to such cardiac myocytes. Such a method involves obtaining bone marrow cells, contacting the bone marrow cells with platelet derived growth factor AB and thereby generating cardiac myocyte from the bone marrow cells. As discussed, the bone marrow cells can be senescent cells and need not be obtained from embryonic tissues. Instead, the bone marrow cells can be obtained from an older patient, even one with a vascular disease, so that after re-introducing the cells to the patient no tissue rejection or other immunological problems will arise. Hence, the inventive methods avoid side effects and other complications.

To promote cardiac myocytes formation from bone marrow cells, the bone marrow cells can be cultured in a sufficient amount of platelet derived growth factor AB for a time and under conditions sufficient to generate myocytes. Platelet derived growth factor is commercially available and can be obtained, for example, from R&D Systems.

A sufficient amount of platelet derived growth factor AB is about 0.001 ng/mL to about 10 mg/mL, or about 0.01 ng/mL to about 1 mg/mL, or about 0.1 ng/mL to about 100 ng/mL or about 1 ng/mL to about 100 ng/mL platelet derived growth factor AB. In certain embodiments, senescent bone marrow cells were successfully treated with platelet derived growth factor AB at concentrations of about 10 ng/mL and 100 ng/mL.

The time used to generate cardiac myocytes from bone marrow by PDGF AB treatment can vary. For example, culturing bone marrow cells in the presence of PDGF AB for a time period of a few days (about 3 days) to several weeks (about 5 weeks) can lead to cardiac myocytes generation from bone marrow cells. In experiments described herein, bone marrow cells were successfully cultured for about 1 week in order to facilitate cardiac myocyte formation.

Conditions required for culturing bone marrow cells to generate cardiac myocytes comprise the conditions normally employed for culturing mammalian cells in vitro. Inclusion of vascular endothelial growth factor (VEGF, at about 10 ng/mL), fibroblast growth factor-2 (FGF-2) (at about 5 ng/mL) and heparin (at about 50 μg/mL) also helps support the generation of cardiac myocytes from bone marrow cells in vitro.

Syngeneic Hematopoietic Stem Cells and Endothelial Cell Precursors

In a useful embodiment of the invention, bone marrow or somatic cells are taken from a patient with a vascular disease. These syngeneic cells can be treated to generate useful cells for treatment of vascular diseases. For example, bone marrow cells can be cultured with platelet derived growth factor AB to generate syngeneic cardiac myocytes that can be re-administered to the patient. Such bone marrow and other somatic cells can also be genetically modified to contain a gene that confers a therapeutic effect. While the genetically modified bone marrow cells that then be administered, the genetically-modified somatic cells are cloned by somatic cell nuclear transfer to produce pluripotent embryo-derived stem cells. Such syngeneic stem cells can be induced to differentiate into hematopoietic stem cells and endothelial cell precursors that can give rise to genetically modified endothelial cells in vivo. The genetically modified hematopoietic stem cells and endothelial cell precursors are then administered to a patient as an autologous transplant, whereupon the endothelial cells derived therefrom home to sites of cardiac angiogenesis or vessel repair. Since the transplanted bone marrow cells, hematopoietic stem cells and endothelial cell precursors are syngeneic with the patient, they are histocompatible and do not elicit an immune response, unless such a response is elicited by expression of the transgene.

An alternative embodiment of the invention that does not use nuclear transfer-derived cells can be practiced as follows:

Endothelial cell precursors can also be isolated from the patient, genetically modified in vitro to contain a gene that confers a therapeutic effect, and are reintroduced to the patient as described in PCT Publication WO 99/37751 by Shahin Rafil, Larry White and Malcolm A. Moore, and U.S. Pat. No. 5,980,887 (Isner et al.), the contents of which are incorporated herein by reference in their entirety. In brief, a sample of blood is drawn form the patient, typically 50–200 ml. Prior to venipuncture, the patient can be treated with factors such as Granulocyte Colony Stimulating Factor (GCSF), which stimulates an increase in the number of circulating endothelial cell precursors. The leukocyte fraction is separated by Ficoll density gradient, then plated briefly to remove adhesive cells. A population of cells positive for antigens specific for endothelial cell precursors, including but not limited to CD34, VGEFR-2, and AC133, is then isolated. For example, the remaining cells can be treated with fluorochrome labeled antibodies to the antigens specific for endothelial cell precursors and isolated by Fluorescence Activated Cell Sorting (FACS). Alternatively, endothelial cell precursors can be isolated by magnetic beads coated with the above antibodies to the above antigens, as is available in the art. Once purified, the population of endothelial cell precursors are cultured in vitro in suitable medium (e.g., M199 media supplemented with 20% fetal bovine serum), and the cells are genetically modified using methods known in the art. Following genetic modification, the endothelial cell precursors are intravenously reintroduced to the patient.

Allogeneic, HLA-matched Endothelial Cell Precursors

Banks of bone marrow cells or of pre-made embryonic stem cell lines can be isolated, where the bone marrow cells or embryonic stem cell lines are each homozygous for at least one MHC gene. Such banks of cells serve as an alternative to using nuclear transfer cloning to produce syngeneic embryonic stem cells de novo and inducing these to differentiate into the required cells for every patient that is in need of therapeutic transplant. However, homozygous embryos generated in vitro or vivo can serve as a source of homozygous MHC stem cells.

The MHC genes of humans are also referred to as HLA (human leukocyte antigen) genes or alleles. Such MHC and HLA genes are highly polymorphic, and banks of different embryonic stem cell lines and different bone marrow isolates with different MHC and HLA genes will include a large number of different embryonic stem cell lines. Once such banks of bone marrow isolates or embryonic stem cells with homozygous MHC alleles are produced, it is possible to provide a patient in need of cell transplant with MHC-matched cells and tissues by selecting and/or expanding a line of bone marrow cells of embryonic stem cells that has MHC allele(s) that match one of those of the patient. The bone marrow or embryonic stem cells can be treated with PDGF AB or other agents to differentiate into the type of cells that the patient requires. Methods for preparing a bank of embryonic stem cell lines that are homozygous for the MHC alleles, and for using these to provide MHC-matched cells and tissues for transplantation therapies are described in co-pending U.S. Provisional Patent Application No. 60/382,616, entitled, "A Bank of Nuclear Transfer-Generated Stem Cells for Transplantation Having Homozygous MHC Alleles, and Methods for Making and Using Such a Stem Cell Bank, filed May 24, 2002, now abandoned, the disclosure of which is incorporated herein by reference in its entirety.

Therefore, in another useful embodiment of the invention, the bone marrow and nuclear donor cells that are genetically modified are not obtained from the patient. Instead, they are taken from a person who has HLA alleles that match those of the patient. More simply, the bone marrow or nuclear donor cells are taken from a person who has homozygous HLA alleles that match at least one HLA allele of the patient. A bank of samples of viable nuclear donor cells, each sample made up of cells having homozygous HLA alleles that match an HLA allele found in the population, is prepared and maintained for practicing this embodiment. See U.S. Provisional Patent Application No. 60/382,616 now abandoned. As described above for syngeneic transplant therapy, genetically modified, HLA-matched hematopoietic stem cells and endothelial cell precursors produced by the invention are administered to a patient as a heterologous transplant, to give rise to endothelial cells that home to and incorporate into the tumor vasculature to disrupt or inhibit tumor angiogenesis. Since the transplanted hematopoietic stem cells and endothelial cell precursors are HLA-matched to the patient, they are partially histocompatible with the patient, and so do not elicit the strong rejection response that would be elicited by a completely allogeneic transplant.

In an alternative embodiment, cells of one or more of the established human embryonic stem cell lines are genetically modified, and available methods are used to induce the genetically modified embryonic stem cells to differentiate into hematopoictic stem cells and endothelial cell precursors. These hematopoietic stem cells and endothelial cell precursors can then give rise to genetically modified endothelial cells that confer a therapeutic effect when recruited into a sites of vascular injury or ischemic myocardium. Alternatively, hematopoietic stem cells and endothelial cell precursors can be isolated directly from a young person other than the patient and when appropriate to the needs of that patient, genetically modified, to confer a therapeutic effect. The hematopoietic stem cells and endothelial cell precursors obtained from differentiating embryonic stem cells or directly from a person other than the patient can then be transplanted into the patient.

Genetic Modification of Somatic Cells, Stem Cells and Endothelial Cell Precursors Transgenic cells of the invention that are genetically modified to contain a stably integrated gene that is expressed in endothelial cells and that confers a therapeutic effect are obtained by methods available in the art. Recombinant expression vectors are made and introduced into the cells using standard echniques, e.g., electroporation, lipid-mediated transfection, or calcium-phosphate mediated transfection, and cells containing stably integrated expression constructs are selected or otherwise identified, also using standard techniques known in the art. Methods for making recombinant DNA expression constructs, introducing them into eukaryotic cells, and identifying cells in which the expression construct is stably integrated and efficiently expressed, are described, for example, in Sambrook, et al., Molecular Cloning: A Laboratory Manual, 2d Edition, Cold Spring Harbor Laboratory Press (1989); Sambrook, et al., Molecular Cloning: A Laboratory Manual, 2d Edition, Cold Spring Harbor Laboratory Press (2001). Such methods useful for practicing the present invention are also described, for example, in U.S. Pat. No. 5,980,887.

A variety of different types of genes that confer a therapeutic effect when expressed in endothelial cells in sites of vascular injury or I-ischemic myocardium. For examples, endothelial precursor cells of the invention can be used to administer therapeutic agents such as enzymes, peptides and/or proteins with biological activity, nucleic acids or genes that encode therapeutic polypeptides, expression vectors or other nucleic acid constructs, for example, naked plasmid DNAs, any vector carrying one or more genes, any sense or anti-sense RNA, or any ribozyme. Nucleic acids encoding such therapeutic agents are introduced into endothelial precursor cells based upon their ability to optimally treat one or more vascular conditions. For example, the endothelial precursor cell can be designed to help control, diminish or otherwise facilitate improved arterial blood flow in the region of the atherosclerotic lesion.

Such therapeutic agents include, for example, thrombolytic agents such as streptokinase, tissue plasminogen activator, plasmin and urokinase, anti-thrombotic agents such as tissue factor protease inhibitors (TFPI), anti-inflammatory agents, metalloproteinase inhibitors, nematode-extracted anticoagulant proteins (NAPs) and the like. Other examples of therapeutic agents that can be expressed in the endothelial precursor cells of the invention include the following: agents that modulate lipid levels (for example, HMG-CoA reductase inhibitors, thyromimetics, fibrates, agonists of peroxisome proliferator-activated receptors (PPAR) (including PPAR-alpha, PPAR-gamma and/or PPAR-delta)); agents that modulate oxidative processes such as modifiers of reactive oxygen species; agents that modulate insulin resistance or glucose metabolism (e.g. agonists of PPAR-alpha, PPAR-gamma and/or PPAR-delta, modifiers of DPP-IV, and modifiers of glucocorticoid receptors); agents that modulate expression of receptors or adhesion molecules or integrins on endothelial cells or smooth muscle cells in any vascular location; agents that modulate the activity of endothelial cells or smooth muscle cells in any vascular location; agents that modulate inflammation associated receptors (e.g. chemokine receptors, RAGE, toll-like receptors, angiotensin receptors, TGF receptors, interleukin receptors, TNF receptors, C-reactive protein receptors, and other receptors involved in inflammatory signaling pathways including the activation of NF-kb); agents that modulate proliferation, apoptosis or necrosis of endothelial cells, vascular smooth muscle, lymphocytes, monocytes, and neutrophils that adhere to or within the vessel; agents that modulate production, degradation, or cross-linking of any extracellular matrix proteins (e.g. collagen, elastin, and proteoglycans); agents that modulate activation, secretion or lipid loading of any cell type within mammalian vessels; agents that modulate the activation or proliferation of dendritic cells within mammalian vessels; and agents that modulate the activation or adhesion of platelets within blood vessels.

The endothelial precursor cells utilized in the methods of the invention express, or over-express, platelet-derived growth factor ("PDGF"). In some embodiments, the endothelial precursor cells are genetically modified to have a recombinant or transgenic PDGF DNA, for example, a PDGF DNA operably linked to a promoter useful for over-expression of a PDGF gene product.

Naturally occurring, platelet-derived growth factor is a disulfide-bonded dimer having two polypeptide chains, namely the "A" and "B" chains, with the A chain being approximately 60% homologous to the B chain. Naturally occurring PDGF is found in three dimeric forms, namely PDGF-AB heterodimer, PDGF-BB homodimer, or PDGF-AA homodimer. Hannink et al., Mol. Cell. Biol., 6, 1304–1314 (1986). PDGF-AB has been identified as a predominate naturally occurring form. However, some data indicates that the PDGF-BB homodimer may be effective for wound healing. Each monomeric subunit of the biologically active dimer, irrespective of whether it is an A chain monomer or a B chain monomer, contains eight cysteine residues. Some of these cysteine residues form interchain disulfide bonds that hold the dimer together. As used herein, the term PDGF means any PDGF polypeptide or protein, including PDGF A, PDGF B, PDGF AB, PDGF BB, and PDGF AA.

The A polypeptide of human PDGF can be any mammalian PDGF A polypeptide including, for example, human, mouse, rat, rabbit, goat, bovine, horse, sheep and any other mammalian PDGF A polypeptide. The following sequence is one example of an amino acid sequence of a human PDGF A polypeptide (SEQ ID NO:1):

```
  1  MRTWACLLLL GCGYLAHALA EEAEIPRELI ERLARSQIHS
 41  IRDLQRLLEI DSVGAEDALE TNLRAHGSHT VKHVPEKRPV
 81  PIRRKRSIEE AIPAVCKTRT VIYEIPRSQV DPTSANFLIW
121  PPCVEVKRCT GCCNTSSVKC QPSRVHHRSV KVAKVEYVRK
161  KPKLKEVQVR LEEHLECACA TSNLNPDHRE EETGRRRESG
201  KKRK
```

A nucleic acid that encodes a human PDGF A polypeptide can be found in the NCBI database at accession number X03795, gi:35365. See website at www.ncbi.nih.nlm.gov.

The following sequence is an example of a mouse PDGF A sequence (SEQ ID NO:2).

```
  1  MRTWACLLLL GCGYLAHALA EEAEIPRELI ERLARSQIHS
 41  IRDLQRLLEI DSVGAEDALE TSLRAHGSHA INHVPEKRPV
 81  PIRRKRSIEE AVPAVCKTRT VIYEIPRSQV DPTSANFLIW
121  PPCVEVKRCT GCCNTSSVKC QPSRVHHRSV KVAKVEYVRK
161  KPKLKEVQVR LEEDLECACA TSNLNPDHRE EETDVR
```

A nucleic acid that encodes a mouse PDGF A polypeptide can be found in the NCBI database at accession number NM 008808, gi:6715565. See website at www.ncbi.nih.nlm.gov.

Other sequences for PDGF A can readily be obtained by one of skill in the art, for example, in the GenBank database of sequences. Variability in these and other sequences is permitted so long as the PDGF A polypeptide can dimerize with PDGF B and/or function in cell-to-cell communication.

The PDGF B polypeptide found in human platelets has been identified as a 109 amino acid cleavage product (PDGF-$B_{109}$) of a 241 amino acid precursor polypeptide Johnsson et al., EMBO Journal, 3(5), 921–928 (1984). An example of a human sequence for the PDGF B polypeptide is provided below (SEQ ID NO:3).

```
  1  MNRCWALFLS LCCYLRLVSA EGDPIPEELY EMLSDHSIRS
 41  FDDLQRLLHG DPGEEDGAEL DLNMTRSHSG GELESLARGR
 82  RSLGSLTIAE PAMIAECKTR TEVFEISRRL IDRTNANFLV
121  WPPCVEVQRC SGCCNNRNVQ CRPTQVQLRP VQVRKIEIVR
161  KKPIFKKATV TLEDHLACKC ETVAAARPVT RSPGGSQEQR
201  AKTPQTRVTI RTVRVRRPPK GKHRKFKHTH DKTALKETLG
241  A
```

A nucleic acid that encodes a human PDGF B polypeptide can be found in the NCBI database at accession number X02811, gi:35371. See website at www.ncbi.nih.nlm.gov.

The following sequence is an example of a mouse PDGF B sequence (SEQ ID NO:4).

```
  1  MNRCWALFLP LCCYLRLVSA EGDPIPEELY EMLSDHSIRS
 41  FDDLQRLLHR DSVDEDGAEL DLNMTRAHSG VELESSSRGR
 81  RSLGSLAAAE PAVIAECKTR TEVFQISRNL IDRTNANFLV
121  WPPCVEVQRC SGCCNNRNVQ CRASQVQMRP VQVRKIEIVR
161  KKPIFKKATV TLEDHLACKC ETIVTPRPVT RSPGTSREQR
201  AKTPQARVTI RTVRIRRPPK GKHRKFKHTH DKAALKETLG
241  A
```

A nucleic acid that encodes a mouse PDGF B polypeptide can be found in the NCBI database at accession number NM 011057, gi:6755009. See website at www.ncbi.nih.nlm.gov.

As recognized by one of skill in the art, these PDGF polypeptides from different mammalian species have similar amino acid sequences. According to the invention any PDGF polypeptide from any mammalian species can be utilized in the practice of the invention so long as the PDGF polypeptide can stimulate endothelial cells to promote angiogenesis.

A 109 amino acid PDGF B polypeptide is believed to be the mature form of PDGF in humans and constitutes a cleavage product of the PDGF-B precursor protein. Homology with the precursor protein begins at amino acid 82 of the 241 amino acid precursor protein and continues for 109 amino acids yielding, for example, a polypeptide with the following sequence (SEQ ID NO:5):

```
 82  RSLGSLTIAE PAMIAECKTR TEVFETSRRL IDRTNANFLV
121  WPPCVEVQRC SGCCNNRNVQ CRPTQVQLRP VQVRKIEIVR
161  KKPIFKKATV TLEDHLACKC ETVAAARPVT RSPGGSQEQR
201  AKTPQTRVTI RTVRVRRPPK GKHRKFKHTH DKTALKETLG
241  A
```

Another form of PDGF-B (PDGF-B$_{119}$), corresponds to the first 119 amino acids of the PDGF-B precursor protein (SEQ ID NO:6):

```
  1  MNRCWALFLS LCCYLRLVSA EGDPIPEELY EMLSDHSIRS
 41  FDDLQRLLHG DPGEEDGAEL DLNMTRSHSG GELESLARGR
 82  RSLGSLTIAE PAMIAECKTR TEVFEISRRL IDRTNANFL
```

This PDGF-B$_{119}$ form has also been identified as a major cleavage product of the precursor protein when the entire gene is encoded into a transfected mammalian host. See U.S Pat. No. 5,149,792.

Human platelet-derived growth factor is believed to be the major mitogenic growth factor in serum for connective tissue cells. PDGF can positively affect mitogenesis in arterial smooth muscle cells, fibroblast cells lines, and glial cells. Deuel et al., J. Biol. Chem., 256(17), 8896–8899 (1981). See also, e.g., Heldin et al., J. Cell Physiol., 105, 235 (1980) (brain glial cells); Raines and Ross, J. Biol. Chem., 257, 5154 (1982) (monkey arterial smooth muscle cells).

In some embodiments, the endothelial precursor cells are genetically modified to have a recombinant or transgenic PDGF receptor DNA, for example, a PDGF receptor DNA operably linked to a promoter useful for over-expression of a PDGF receptor. Examples of amino acid and nucleotide sequences for the PDGF receptor(s) can be found in the NCBI database. See website at www.ncbi.nih.nlm.gov. One example of a sequence for the human PDGF alpha receptor is provided below (accession number PFHUGA, gi:66814, SEQ ID NO:35):

```
  1  MGTSHPAFLV LGCLLTGLSL ILCQLSLPSI LPNENEKVVQ
 41  LNSSFSLRCF GESEVSWQYP MSEEESSDVE IRNEENNSGL
 81  FVTVLEVSSA SAAHTGLYTC YYNHTQTEEN ELEGRHIYIY
121  VPDPDVAFVP LGMTDYLVIV EDDDSAIIPC RTTDPETPVT
161  LHNSEGVVPA SYDSRQGFNG TFTVGPYICE ATVKGKKFQT
201  IPENVYALKA TSELDLEMEA LKTVYKSGET IVVTCAVFNN
241  EVVDLQWTYP GEVKGKGITM LEEIKVPSIK LVYTLTVPEA
281  TVKDSGDYEC AARQATREVK EMKKVTISVH EKGFIEIKPT
321  PSQLEAVNLH EVKHFVVEVR AYPPPRISWL KNNLTLIENL
361  TEITTDVEKI QEIRYRSKLK LIRAKEEDSG HYTIVAQNED
401  AVKSYTFELL TQVPSSILDL VDDHHGSTGG QTVRCTAEGT
441  PLPDIEWMIC KDIKKCNNET SWTILANNVS NIITEIHSRD
481  RSTVEGRVTF AKVEETIAVR CLAKNLLGAE NRELKLVAPT
521  LRSELTVAAA VLVLLVIVII SLIVLVVIWK QKPRYEIRWR
561  VIESISPDGH EYIYVDPMQL PYDSRWEFPR DGLVLGRVLG
601  SGAFGKVVEG TAYGLSRSQP VMKVAVKMLK PTARSSEKQA
641  LMSELKIMTH LGPHLNIVNL LGACTKSGPI YIITEYCFYG
681  DLVNYLHKNR DSFLSHHPEK PKKELDIFGL NPADESTRSY
721  VILSFENNGD YMDMKQADTT QYVPMLERKE VSKYSDIQRS
761  LYDRPASYKK KSMLDSEVKN LLSDDNSEGL TLLDDLLSFTY
801  QVARGMEFLA SKNCVHRDLA ARNVLLAQGK IVKICDFGLA
841  RDIMHDSNYV SKGSTFLPVK WMAPESIFDN LYTTLSDVWS
881  YGILLWEIFS LGGTPYPGMM VDSTFYNKIK SGYRMAKPDH
921  ATSEVYEIMV KCWNSEPEKR PSFYHLSEIV ENLLPGQYKK
961  SYEKIHLDFL KSDHPAVARM RVDSDNAYIG VTYKNEEDKL
1001 KDWEGGLDEQ RLSADSGYII PLPDIDPVPE EEDLGKRNRH
1041 SSQTSEESAI ETGSSSSTFI KREDETIEDI DMMDDIGIDS
1081 SDLVEDSFL
```

An example of a sequence for the human PDGF beta receptor is provided below (accession number NP 002600, gi:4505683, SEQ ID NO:36):

```
  1  MRLPGAMPAL ALKGELLLLS LLLLLEPQIS QGLVVTPPGP
 41  ELVLNVSSTF VLTCSGSAPV VWERMSQEPP QEMAKAQDGT
 81  FSSVLTLTNL TGLDTGEYFC THNDSRGLET DERKRLYIPV
121  PDPTVGFLPN DAEELFIFLT EITEITIPCR VTDPQLVVTL
161  HEKKGDVALP VPYDHQRGFS GIFEDRSYIC KTTIGDREVD
201  SDAYYVYRLQ VSSINVSVNA VQTVVRQGEN ITLMCIVIGN
241  EVVNFEWTYP RKESGRLVEP VTDFLLDMPY HIRSILHIPS
281  AELEDSGTYT CNVTESVNDH QDEKAINITV VESGYVRLLG
321  EVGTLQFAEL HRSRTLQVVF EAYPPPTVLW FKDNRTLGDS
361  SAGEIALSTR NVSETRYVSE LTLVRVKVAE AGHYTMRAFH
401  EDAEVQLSFQ LQINVPVRVL ELSESHPDSG EQTVRCRGRG
441  MPQPNIIWSA CRDLKRCPRE LPPTLLGNSS EEESQLETNV
481  TYWEEEQEFE VVSTLRLQHV DRPLSVRCTL RNAVGQDTQE
521  VIVVPHSLPF KVVVISAILA LVVLTIISLI ILIMLWQKKP
561  RYEIRWKVIE SVSSDGHEYI YVDPMQLPYD STWELPRDQL
601  VLGRTLGSGA FGQVVEATAH GLSHSQATMK VAVKMLKSTA
641  RSSEKQALMS ELKIMSHLGP HLNVVNLLGA CTKGGPIYII
681  TEYCRYGDLV DYLHRNKHTF LQHHSDKRRP PSAELYSNAL
721  PVGLPLPSHV SLTGESDGGY MDMSKDESVD YVPMLDMKGD
761  VKYADIESSN YMAPYDNYVP SAPERTCRAT LINESPVLSY
801  MDLVGFSYQV ANGMEFLASK NCVHRDLAAR NVLICEGKLV
841  KICDFGLARD IMRDSNYISK GSTFLPLKWM APESIFNSLY
```

```
-continued

881  TTLSDVWSFG  ILLWEIFTLG  GTPYPELPMN  EQFYNAIKRG

921  YRMAQPAHAS  DEIYEIMQKC  WEEKFEIRPP  FSQLVLLLER

961  LLGEGYKKKY  QQVDEEFLRS  DHPAILRSQA  RLPGFHGLRS

1001  PLDTSSVLYT  AVQPNEGDND  YIIPLPDPKP  EVADEGPLEG

1041  SPSLASSTLN  EVNTSSTISC  DSPLEPQDEP  EPEPQLELQV

1081  EPEPELEQLP  DSGCPAPRAE  AEDSFL
```

A nucleic acid that encodes such a human PDGF beta receptor can be found in the NCBI database at accession number NM 002609, gi:15451788. See website at www.ncbi.nih.nlm.gov.

Other members of the PDGF family that may have utility when expressed by the endothelial precursor cells of the invention include vascular endothelial cell growth factor ("VEGF", sometimes also referred to as "vascular permeability factor, or "VPF") and placental growth factor ("PLGF"). Tischer et al., Biochem. Biophys. Res. Comm., 165(3), 1198–1206 (1989) and Maglione et al., Proc. Natl. Acad. Sci. USA, 88, 9267–9271 (1991), respectively. Both VEGF and PLGF form disulfide-bonded dimers from the eight highly conserved cysteine residues that appear in the PDGF homologous region of each monomeric unit of these PDGF family members. Tischer et al. and Maglione et al., ibid. The receptors for VEGF and PLGF are also in the same receptor subfamily as the PDGF receptors. Consequently, these "newer" members of the PDGF family are thought to be potentially useful as therapeutic products in wound repair and, according to the invention can be used herein to treat and prevent vascular conditions.

Hence, the endothelial precursor and other cells of the invention can be modified to express a therapeutic agent such as those described herein. Such genetic modifications can be performed by procedures available to one of skill in the art. For example, a nucleic acid encoding the therapeutic agent can be placed within an expression cassette or expression vector, and the cassette or vector can be introduced into the cell. The expression cassette can be placed within a vector to generate an expression vector.

Any vector that can replicate in a selected cell can be utilized in the invention. In general, the vector is an expression vector that provides the nucleic acid segments needed for expression of the therapeutic agent polypeptides. Various vectors are publicly available. The vector may, for example, be in the form of a plasmid, cosmid, viral particle, or phage. Vector components generally include, but are not limited to, one or more of a signal sequence, an origin of replication, one or more marker genes, an enhancer element, a promoter, and a transcription termination sequence.

The therapeutic agent nucleic acid sequences may be inserted into the vector by a variety of procedures. In general, DNA is inserted into an appropriate restriction endonuclease site(s) using techniques known in the art. See generally, Sambrook et al., 1989, Molecular Cloning, A Laboratory Manual, 2d ed., Cold Spring Harbor Laboratory Press, Cold Spring Harbor, N.Y.; Sambrook and Russell, Molecular Cloning: A Laboratory Manual, 3rd edition (Jan. 15, 2001) Cold Spring Harbor Laboratory Press, ISBN: 0879695765; Ausubel et al., *Current Protocols in Molecular Biology*, Green Publishing Associates and Wiley Interscience, NY (1989)). Construction of suitable expression vectors containing a therapeutic agent can employ standard ligation techniques that are known to the skilled artisan.

The expression cassette or vector of the invention includes a promoter. A promoter is a nucleotide sequence that controls expression of an operably linked nucleic acid sequence by providing a recognition site for RNA polymerase, and possibly other factors, required for proper transcription. A promoter includes a minimal promoter, consisting only of all basal elements needed for transcription initiation, such as a TATA-box and/or other sequences that serve to specify the site of transcription initiation. Any promoter able to direct transcription of an RNA encoding the selected therapeutic agent may be used. Accordingly, many promoters may be included within the expression cassette or vector of the invention. Some useful promoters include, constitutive promoters, inducible promoters, regulated promoters, cell specific promoters, viral promoters, and synthetic promoters. A promoter may be obtained from a variety of different sources. For example, a promoter may be derived entirely from a native gene, be composed of different elements derived from different promoters found in nature, or be composed of nucleic acid sequences that are entirely synthetic. A promoter may be derived from many different types of organisms and tailored for use within a given cell, for example, an endothelial precursor cell.

Many mammalian promoters are known in the art that may be used in conjunction with the expression cassette of the invention. Mammalian promoters often have a transcription initiating region, which is usually placed proximal to the 5' end of the coding sequence, and a TATA box, usually located 25–30 base pairs (bp) upstream of the transcription initiation site. The TATA box is thought to direct RNA polymerase II to begin RNA synthesis at the correct site. A mammalian promoter may also contain an upstream promoter element, usually located within 100 to 200 bp upstream of the TATA box. An upstream promoter element determines the rate at which transcription is initiated and can act in either orientation (Sambrook et al., "Expression of Cloned Genes in Mammalian Cells", in: Molecular Cloning: A Laboratory Manual, 2nd ed., 1989).

Mammalian viral genes are often highly expressed and have a broad host range; therefore sequences encoding mammalian viral genes often provide useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallothionein gene, also provide useful promoter sequences. Expression may be either constitutive or regulated.

A mammalian promoter may also be associated with an enhancer. The presence of an enhancer will usually increase transcription from an associated promoter. An enhancer is a regulatory DNA sequence that can stimulate transcription up to 1000-fold when linked to homologous or heterologous promoters, with synthesis beginning at the normal RNA start site. Enhancers are active when they are placed upstream or downstream from the transcription initiation site, in either normal or flipped orientation, or at a distance of more than 1000 nucleotides from the promoter. (Maniatis et al., *Science*, 236:1237 (1987); Alberts et al., Molecular Biology of the Cell, 2nd ed., 1989)). Enhancer elements derived from viruses are often times useful, because they usually have a broad host range. Examples include the SV40 early gene enhancer (Dijkema et al., *EMBO J.*, 4:761 (1985) and the enhancer/promoters derived from the long terminal repeat (LTR) of the Rous Sarcoma Virus (Gorman et al., *Proc. Natl.*

*Acad. Sci. USA,* 79:6777 (1982b)) and from human cytomegalovirus (Boshart et al., *Cell,* 41: 521 (1985)). Additionally, some enhancers are regulatable and become active only in the presence of an inducer, such as a hormone or metal ion (Sassone-Corsi and Borelli, *Trends Genet.,* 2:215 (1986); Maniatis et al., *Science,* 236:1237 (1987)).

It is understood that many promoters and associated regulatory elements may be used within the expression cassette of the invention to transcribe an encoded polypeptide. The promoters described above are provided merely as examples and are not to be considered as a complete list of promoters that are included within the scope of the invention.

The expression cassettes and vectors of the invention may contain a nucleic acid sequence for increasing the translation efficiency of an mRNA encoding a therapeutic agent of the invention. Such increased translation serves to increase production of the therapeutic agent. Because eucaryotic mRNA does not contain a Shine-Dalgamo sequence, the selection of the translational start codon is usually determined by its proximity to the cap at the 5' end of an mRNA. However, the nucleotides immediately surrounding the start codon in eucaryotic mRNA influence the efficiency of translation. Accordingly, one skilled in the art can determine what nucleic acid sequences will increase translation of a polypeptide encoded by the expression cassettes and vectors of the invention.

Termination sequences can also be included in the cassettes and vectors of the invention. Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation (Birmstiel et al., *Cell,* 41:349 (1985); Proudfoot and Whitelaw, "Termination and 3' end processing of eukaryotic RNA", in: Transcription and Splicing (eds. B. D. Hames and D. M. Glover) 1988; Proudfoot, *Trends Biochem. Sci.,* 14:105 (1989)). These sequences direct the transcription of an mRNA that can be translated into the polypeptide encoded by the DNA. Examples of transcription terminator/polyadenylation signals include those derived from SV40 (Sambrook et al., "Expression of cloned genes in cultured mammalian cells", in: Molecular Cloning: A Laboratory Manual, 1989).

As indicated above, nucleic acids encoding the therapeutic agents can be inserted into any convenient vector. Vectors that may be used include, but are not limited to, those that can be replicated in prokaryotes and eukaryotes. For example, vectors may be used that are replicated in bacteria, yeast, insect cells, and mammalian cells. Examples of vectors include plasmids, phagemids, bacteriophages, viruses, cosmids, and F-factors. However, specific vectors may be used for specific cells types. Additionally, shuttle vectors may be used for cloning and replication in more than one cell type. Such shuttle vectors are known in the art. The nucleic acid constructs or libraries may be carried extrachromosomally within a host cell or may be integrated into a host cell chromosome. Numerous examples of vectors are known in the art and are commercially available. (Sambrook and Russell, Molecular Cloning: A Laboratory Manual, 3rd edition (Jan. 15, 2001) Cold Spring Harbor Laboratory Press, ISBN: 0879695765; New England Biolab, Beverly, Mass.; Stratagene, La Jolla, Calif.; Promega, Madison, Wis.; ATCC, Rockville, Md.; CLONTECH, Palo Alto, Calif.; Invitrogen, Carlabad, Calif.; Origene, Rockville, Md.; Sigma, St. Louis, Mo.; Pharmacia, Peapack, N.J.; USB, Cleveland, Ohio). These vectors also provide many promoters and other regulatory elements that those of skill in the art may include within the nucleic acid constructs of the invention through use of known recombinant techniques.

A nucleic acid construct, or an expression vector can therefore be inserted into any mammalian vector that is known in the art or that is commercially available, for example, as provided by CLONTECH (Carlsbad, Calif.), Promega (Madision, Wis.), or Invitrogen (Carlsbad, Calif.). Such vectors may contain additional elements such as enhancers and introns having functional splice donor and acceptor sites. Nucleic acid constructs may be maintained extrachromosomally or may integrate in the chromosomal DNA of a host cell. Mammalian vectors include those derived from animal viruses, which require trans-acting factors to replicate. For example, vectors containing the replication systems of papovaviruses, such as SV40 (Gluzman, *Cell,* 23:175 (1981)) or polyomaviruses, replicate to extremely high copy number in the presence of the appropriate viral T antigen. Additional examples of mammalian vectors include those derived from bovine papillomavirus and Epstein-Barr virus. Additionally, the vector may have two replication systems, thus allowing it to be maintained, for example, in mammalian cells for expression and in a prokaryotic host for cloning and amplification. Examples of such mammalian-bacteria shuttle vectors include pMT2 (Kaufman et al., *Mol. Cell. Biol.,* 9:946 (1989)) and pHEBO (Shimizu et al., *Mol. Cell. Biol.,* 6:1074 (1986)).

The invention is directed to cells that express a heterologous protein or overexpress a native protein, and nucleic acids or expression vector encoding such a heterologous or native protein. Such cells may be used for treating and preventing vascular conditions, as described herein.

Methods for introduction of heterologous polynucleotides into mammalian cells are known in the art and include lipid-mediated transfection, dextran-mediated transfection, calcium phosphate precipitation, polybrene-mediated transfection, protoplast fusion, electroporation, encapsulation of -the polynucleotide(s) in liposomes, biollistics, and direct microinjection of the DNA into nuclei. The choice of method depends on the cell being transformed as certain transformation methods are more efficient with one type of cell than another. (Felgner et al., *Proc. Natl. Acad. Sci.,* 84:7413 (1987); Felgner et al., *J. Biol. Chem.,* 269:2550 (1994); Graham and van der Eb, *Virology,* 52:456 (1973); Vaheri and Pagano, *Virology,* 27:434 (1965); Neuman et al., *EMBO J.,* 1:841 (1982); Zimmerman, *Biochem. Biophys. Acta.,* 694:227 (1982); Sanford et al., *Methods Enzymol.,* 217:483 (1993); Kawai and Nishizawa, *Mol. Cell. Biol,* 4:1172 (1984); Chaney et al., *Somat. Cell Mol. Genet.,* 12:237 (1986); Aubin et al., *Methods Mol. Biol.,* 62:319 (1997)). In addition, many commercial kits and reagents for transfection of eukaryotic cells are available.

Following transformation or transfection of a nucleic acid into a cell, the cell may be selected for the presence of the nucleic acid through use of a selectable marker. A selectable marker is generally encoded on the nucleic acid being introduced into the recipient cell. However, co-transfection of selectable marker can also be used during introduction of nucleic acid into a host cell. Selectable markers that can be expressed in the recipient host cell may include, but are not limited to, genes that render the recipient host cell resistant to drugs such as actinomycin $C_1$, actinomycin D, amphotericin, ampicillin, bleomycin, carbenicillin, chloramphenicol, geneticin, gentamycin, hygromycin B, kanamycin monosulfate, methotrexate, mitomycin C, neomycin B sulfate, novobiocin sodium salt, penicillin G sodium salt, puromycin dihydrochloride, rifampicin, streptomycin sulfate, tetracycline hydrochloride, and erythromycin. (Davies et al., *Ann. Rev. Microbiol.*, 32: 469 (1978)). Selectable markers may also include biosynthetic genes, such as those in the histidine, tryptophan, and leucine biosynthetic pathways. Upon transfection or transformation of a cell, the cell is placed into contact with an appropriate selection agent.

Accordingly, the invention provides methods for generating and using genetically modified endothelial precursor cells that can express useful therapeutic agents.

Suicide Genes for Eliminating Grafted Endothelial Cells

The invention is also directed to genetically-modified endothelial cell precursors that express a selectable suicide gene, such as thymidine kinase (TK), which allows negative selection of grafted cells upon completion of treatment or in the event of undesired complications. TK-expressing cells can be negatively selected by the administration of gancyclovir according to methodology known in the art. Alternatively, the endothelial cell precursors can be genetically-modified to express cytosine deaminase, which causes the cells to die in the presence of added 5-fluorocytosine. The expressed gene can be lethal as a toxin or lytic agent.

Endothelial precursor cells and other cells can be genetically modified to express such "suicide genes" by available recombinant techniques, for example, as described herein.

Methods for Inducing Neovascularization

The present invention provides novel therapeutic methods employing cell therapy to treat vascular diseases, including atherosclerosis and heart disease. The invention is further directed to a method for inducing angiogenesis or neovascularization in a mammal by administering to the mammal an effective amount of a population of endothelial precursor cells, cardiac microvascular endothelial cells (CMECs), young bone marrow cells, stem cells, embryonic stem cell lines or hematopoietic stem cells.

Neovascularization refers to the development of new blood vessels from endothelial precursor cells by any means, such as by vasculogenesis, angiogenesis, or the formation of new blood vessels from endothelial precursor cells that link to existing blood vessels. Angiogenesis is the process by which new blood vessels grow from the endothelium of existing blood vessels in a developed animal. Angiogenesis is essential for wound healing and for reproduction. Endothelial precursor cells circulate in the blood and selectively migrate, or "home," to sites of active angiogenesis (see U.S. Pat. No. 5,980,887, Isner et al., the contents of which are incorporated herein by reference in their entirety).

Endothelial precursor cells may be pre-treated or co-administered with cytokines and other factors, such as, for example, PDGF, G-CSF, GM-CSF, VEGF, SCF (c-kit ligand) and bFGF, chemokines, such as SDF-1, or interleukins, such as interleukins 1 and 8. In some embodiments, endothelial precursor cells are pre-treated with such cytokines before administration to a mammal. As demonstrated herein, PDGF isoforms can also stimulate endothelial precursor cells to generate myocytes. Therefore, in some embodiments, endothelial precursor cells are pre-treated with PDGF A, PDGF B, PDGF BB or PDGF AB before administration to a mammal. Preferably, the endothelial precursor cells are pretreated with PDGF AB.

According to the invention, a platelet-derived growth factor-mediated communication exists between endothelial cells and myocytes. The PDGF dependent communication pathway comprises a series of cellular and biochemical events. Such a pathway involves cardiac myocytes that induce endothelial cells and endothelial precursor cells to express PDGF B. The PDGF B polypeptide can combine with PDGF A to generate PDGF AB. The PDGF AB protein can then stimulate endothelial cells that express the PDGFα receptor to express VEGF as well as FLK-1 and other genes. Overall, the induction of PDGF AB expression by endothelial cells or by endothelial precursor cells promotes angiogenic function. Some variations in this pathway exist. For example, a PDGF BB dimer can form that has activity. Hence, the PDGF BB dimer can also stimulate endothelial cells to express VEGF, FLK-1 and other genes.

In the heart, cardiac microvascular endothelial cells (CMECs) communicate with neighboring cardiac myocytes via PDGF. Cardiac myocytes induce CMECs to express the PDGF B isoform that combines with the constitutively expressed PDGF A isoform to form the PDGF AB heterodimer. This results in the induction of a cascade of molecular events that maintain vascular integrity, including the endothelial expression of vascular endothelial growth factor (VEGF) and VEGF receptor-2 (Flk-1, VEGFR-2).

According to the invention, PDGF dependent pathways mediated by endothelial precursor cells can generate cardiac myocytes from mammalian bone marrow. Precursor endothelial cells can supply PDGF to aging vascular tissues that have an impaired ability to generate new blood vessels. Young adult bone marrow-derived endothelial precursor cells can recreate a platelet-derived growth factor (PDGF)-mediated communication pathway between endothelial precursor cells and cardiac myocytes and thereby contribute to the generation of cardiac myocytes. While this pathway is required for cardiac vascular development and function, the pathway is lost or disrupted in older cardiac tissues and in older bone marrow. However, administration of PDGF and/or precursor endothelial cells can rescue the cardioplastic potential of the aging bone marrow.

According to the invention, disruption of these angiogenic pathways may lead to angiogenic defects. As recognized by the invention, this PDGF dependent communication pathway is dysfunctional in the aging heart and in the aging vasculature of mammals. "Dysfunctional" as used herein means that one or more steps in the PDGF dependent communication pathway are not functioning properly, for example, endothelial cells in the aging heart do not express PDGF B in the presence of cardiac myocytes.

However, the invention provides methods of restoring PDGF B, PDGF AB and/or PDGF BB functions by delivery of exogenous growth factor or by recruitment of transplanted young bone marrow endothelial precursor cells can reverse the senescent impairment in cardiac angiogenic function. Thus, as provided herein, endothelial precursor cells can also help restore and stimulate cardiac myocyte generation. Endothelial precursor cells can be used to rejuvenate aging bone marrow from a mammal suffering from heart disease or other vascular diseases.

As described herein, when bone marrow is removed from older individuals, it cannot respond to myocytes and does not express PDGF B. However, when such older bone marrow cells are cultured with endothelial precursor cells, those bone marrow cells begin to express PDGF B, and begin to generate cardiac myocytes. Use of PDGF isoforms can enhance the speed at which cardiac myocytes are generated from all types of endothelial precursor cells. Use of an individual's own cells (e.g. bone marrow) avoids problems of cell typing, cell matching and the potential for immunological rejection of mismatched cells.

The invention provides cardiac myocytes exhibiting cardioplastic potential that can be derived from endothelial precursor cells obtained from a patient having senescent cardiac angiogenic function. These cardiac myocytes are obtained through a process of culturing the endothelial precursor cell in the presence of an effective amount of PDGF, for example, PDGF AB or PDGF BB. Such endothelial precursor cells can be derived from bone marrow, peripheral blood, umbilical cord blood, organs, tissue, or fat.

The invention further provides a method of treating a patient having senescent cardiac angiogenic function by administering endothelial precursor cells obtained from the patient having senescent cardiac angiogenic function, wherein the endothelial precursor cells were cultured in the presence of an effective amount of PDGF prior to administration. Such PDGF can be, for example, PDGF AB or PDGF BB. Such endothelial precursor cells can be derived from bone marrow, peripheral blood, umbilical cord blood, organs, tissue, or fat.

According to the invention, the actions of PDGF extend beyond the direct regulation of blood vessels and are critical in establishing and/or maintaining an environment that permits the generation of cardiac myocytes from bone marrow stem cells. The senescent impairment in cardiac myocyte-endothelial-PDGF-B expression pathway diminishes the systemic capacity to generate myocardial cells for the aging heart and contributes to the increased pathogenesis of cardiovascular disease in older persons. Since PDGF-AB enhances the generation of cardiac myocytes of bone marrow cells of all age groups, the critical downstream pathways in the precursor cells from the senescent bone marrow are likely to be intact.

The present invention provides experimental results demonstrating that aging-associated alterations in endothelial cells inhibit the induction of the PDGF B-dependent cardiac communication pathway that governs cardiac angiogenic function. Restoration of this pathway by administration of an exogenous growth factor such as PDGF AB, or transplantation of endothelial precursor cells specifically restored cardiac angiogenic function in the aging host, and provides methods and compositions for treatment of cardiovascular disease in older individuals. The present studies were performed in unirradiated, wild type aged mice demonstrating the potential utility of bone marrow endothelial precursor cells in reconstituting endothelial function in the intact vasculature without ablating the host bone marrow.

In other embodiments, the invention provides a method of delivering PDGF B to vascular tissues that includes administering an effective amount of endothelial precursor cells to a mammal. The precursor endothelial cells become localized in cardiac tissues, and other vascular tissues, and may release PDGF B to those tissues. Such release of PDGF may be sustained but need not be. A single administration of such cells may be sufficient. Administration provides a naturally functioning cell type that may only need to be administered once or twice to generate myocytes and stimulate vascularization.

Thus, the invention provides methods for restoring senescent cardiac angiogenic function by administering bone marrow endothelial precursor cells that can, for example, be recruited from young bone marrow or from PDGF-treated older bone marrow. Transplantation of endothelial precursor populations offers a simple and natural way to deliver PDGF B and angio-competent endothelial cells to sites in need of angiogenesis. Endothelial precursor cells are administered as described hereinbelow. A preferred method of administration is intravascular administration.

Administration

Endothelial precursor cells may be administered in any manner used by one of skill in the art to introduce the cells into the vascular system of the host. The cells may be introduced into a specific site in the vascular system to optimize delivery to a site that is known to have a vascular condition or disease. Such local delivery may avoid stimulation of inappropriate vascularization, for example, within a tumor that may be present in the mammal. However, endothelial precursor cells can find their way to diseased vascular tissues, so local administration may not be needed. Moreover, endothelial precursor cells may not play a large role in tumor development because recent studies suggest tumor angiogenesis may proceed, at least in part, through a unique and unexpected pathway. Hence, concerns about stimulating tumor growth may be unfounded.

Endothelial precursor cells and/or bone marrow cells may be administered by intravascular, intravenous, intraarterial, intraperitoneal, intraventricular infusion, infusion catheter, balloon catheter, bolus injection, direct application to tissue surfaces during surgery, or other convenient routes. The cells can be washed after collection, cultured in an appropriate medium to insure their viability and to enhance their numbers. Prior to administration, the cells can also be cultured in the presence of growth factors such as PDGF (e.g. PDGF AB), G-CSF, GM-CSF, VEGF, SCF (c-kit ligand), bFGF, chemokines such as SDF-1, or interleukins such as interleukins 1 and 8. Before administration, the cells can be washed again, for example, in buffered physiological saline.

The volume of cells that is injected and the concentration of cells in the transplanted solution depend on the site of administration, the vascular disease, and the species of the host. Preferably about one-half to about five microliters is injected at a time. The number of cells injected can vary, for example, about $10^2$ to about $10^{10}$ or about $10^4$ to about $10^9$ cells can be injected at one time. While a single injection may be sufficient, multiple injections may also be used for prevention or treatment of vascular diseases.

Platelet derived growth factor isoforms can be administered with or without the endothelial precursor cells or young bone marrow cells of the invention. The cells may also be designed to over-express platelet derived growth factor, as described above. PDGF polypeptides can be incorporated into pharmaceutical compositions that also contain endothelial precursor cells or young bone marrow cells and that are suitable for administration to a mammal. Such compositions may also contain a pharmaceutically acceptable carrier.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. The use of such media and agents for delivering cells is well known in the art. Except insofar as any conventional media or agent is incompatible with the cells or polypeptides provided herein, use thereof in the compositions is contemplated. Supplementary active compounds can also be incorporated into the compositions.

A pharmaceutical composition of the invention is formulated to be compatible with its intended route of administration. Examples of routes of administration include intravenous, intraarterial, intracoronary, parenteral, subcutaneous, subdermal, or subcutaneous. Solutions or suspensions used for such administration can include other components such as sterile diluents like water for dilution, saline solutions, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The composition can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions to accompany the cellular suspensions can be prepared by incorporating an active compound (e.g., a PDGF B polypeptide or PDGF AB protein) in the required amount in an appropriate solvent with a selected combination of ingredients, followed by filter sterilization. Generally, dispersions are prepared by incorporating an active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

It is especially advantageous to formulate the cells and/or compositions in dosage unit form for ease of administration and uniformity of dosage. Dosage unit form as used herein refers to physically discrete units suited as unitary dosages for the subject to be treated. Each unit can then contain a predetermined quantity of the endothelial precursor cells and other components calculated to produce the desired therapeutic effect in association with the required pharmaceutical carrier.

The cellular preparations and pharmaceutical compositions can be included in a kit, e.g., in a container, pack, or dispenser together with instructions for administration.

The following examples are intended to illustrate the invention and should not be interpreted to limit it in any manner.

EXAMPLE 1

Endothelial Precursor Cells Restore Angiogenesis

This Example provides data illustrating that endothelial dysregulation in the PDGF communication pathway underlies the impairment in senescent cardiac angiogenic potential and that young adult BM-derived endothelial precursor cells can reverse this defect and restore cardiac angiogenesis in the aging host.

Methods

Molecular Studies

Samples of the ventricular myocardium were isolated from 3 month old (n=3) and 18 month old C57B61/L mice (n=3). Total RNA was isolated (RNeasy and QIAshedder kits, Qiagen Valencia Calif.) and analyzed by RT-PCR (Hotstar Taq PCR, Qiagen) for expression of PDGF A and PDGF B as well as β-actin. Cardiac microvascular endothelial cells (CMECs) were isolated from 3 month old and 18 month old C57B61/L mice and cardiac myocytes from fetal murine hearts, as previously described. Edelberg et al. *J Clin Invest.* 1998: 102:837–43; Aird et al. *J. Cell Biol.* 1997: 138: 1117–24; Edelberg et al. *J Clin Invest.* 1998: 101: 337–43. These CMECs were then cultured in DMEM supplemented with 5% fetal calf serum, 20 U/mL heparin, 1% BME vitamins, 5 μg/mL insulin, 5 μg/mL transferrin, 5 ng/mL selenium, 100 μg/mL streptomycin, and 500 μg/mL penicillin, 4 μg/mL endothelial growth factor and 1% endothelial cell growth supplement (all from Sigma, St. Louis Mo.).

Bone marrow (BM) endothelial precursor cells were isolated from 3 and 18 month old mice as previously described. Lin et al. J Clin Invest. 2000;105:71–77. These BM endothelial precursor cells were then cultured in DMEM supplemented with 10% fetal calf serum, and 50 μg/mL heparin, 100 μg/mL streptomycin, and 500 μg/mL penicillin (all from Sigma) and 10 ng/mL vascular endothelial cell growth factor, 5 ng/mL fibroblast growth factor-2 (R & D Systems, Minneapolis Minn.). The endothelial cell cultures were expanded for two passages, confirmed by Di-Ac-LDL uptake and PECAM staining, and then plated into 12 well dishes ($10^5$ cell/well) (Costar, Cambridge Mass.).

Fetal cardiac myocytes (E15.5d) were isolated and plated in 12 mm 0.4 μm pore transwells ($10^5$ cell/ transwell) and then were transferred at different time points (0 to 48 hours) into 3-month and 18-month old bone marrow-derived endothelial precursor cells seeded wells as described in Edelberg et al. 2002 *Circulation* 105:608–13 and Edelberg et al. *J Clin Invest.* 1998; 102:837–43. As controls, cardiac microvascular endothelial cells were also isolated from 3-month and 18-month old C57B61/L mice and were cultured alone and with fetal cardiac myocytes for 48 hours as described in Edelberg et al. 2002 *Circulation* 105:608–13. At the termination of the co-culture total RNA was isolated from the endothelial cell wells and RT-PCR was performed. The following sets of oligonucleotide primers were employed:

```
mouse PDGF A:
(forward):
5'TCAAGGTGGCCAAAGTGGAG3'            (SEQ ID NO:7)

(reverse):
5'CTCTCTGTGACAAGGAAGCT3'            (SEQ ID NO:8)

mouse PDGF B:
(forward):
5'ATCGCCGAGTGCAAGACGCG3'            (SEQ ID NO:9)

(reverse):
5'AAGCACCATTGGCCGTCCGA3'            (SEQ ID NO:10)

mouse PDGFRα
(forward):
5'ACAGAGACTGAGCGCTGACA3'            (SEQ ID NO:11)

(reverse):
5'TTCCAAGAAGGAAGGAAGCA3'            (SEQ ID NO:12)

mouse VEGF-164:
(forward):
5'GGATCCATGAACTTTCTGCTGCTGTCTTGG3'  (SEQ ID NO:13)

(reverse):
5'TTCTGGCTTTGTCCTGTCTTTCTTTGG3'     (SEQ ID NO:14)

mouse Elk-1:
(forward):
5'CAGCTTGCTCCTTCCTCATC3'            (SEQ ID NO:15)

(reverse):
5'TCTGGAGAGCAAACCAACCA3'            (SEQ ID NO:16)

mouse von Willebrand Factor
(forward):
5'TGTCCAAGGTCTGAAGAAGA3'            (SEQ ID NO:17)

(reverse):
5'CAGGACAAACACCACATCCA3'            (SEQ ID NO:18)

mouse PECAM
(forward):
5'CAAGCGGTCGTGAATGACAC3'            (SEQ ID NO:19)

(reverse):
5'CACTGCCTTGACTGTCTTAAG3'           (SEQ ID NO:20)

mouse β-actin
(forward)
5'GTGGGCCGCTCTAGGCACCAA3'           (SEQ ID NO:21)

(reverse)
5'CTCTTTGATGTCACGCACGATTTC3'        (SEQ ID NO:22)
```

Cellular and secreted protein samples were isolated from additional endothelial cell cultures in the presence or absence of fetal cardiac myocytes as previously described. Edelberg et al. *J Clin Invest.* 1998;102:837–43. Secreted samples (50 μl) from endothelial cells cultured alone or in the presence of cardiac myocytes were applied to Nunc maxisrop plates (Roskilde, Denmark) for 1 hour at room temperature. The samples were then washed with PBS 3 times, followed by blocking with 5% casein in PBS. Polyclonal antibodies to PDGF A (1:500, sc-128 Santa Cruz Biotechnology, Santa Cruz Calif.) and B, (1:300 dilution sc-7878, Santa Cruz Biotechnology), VEGF (1:200, AF 493-NA, R&D Systems), were then employed. Cellular lysate samples (50 μL) were assayed with antibodies directed against Flk-1 (1:500, AF 644, R&D Systems), PDGFRα (1:200, AF322, R&D Systems), and PECAM (1:500 dilution 550274, BD Pharmigen San Diego Calif.). After washing with PBS three times the plates were developed with peroxidase-labeled donkey polyclonal antibodies to goat, rabbit, and rat IgG (1:1000, Jackson Immunoresearch Laboratories, West Grove Pa.) and assayed as previously described. Edelberg et al. *J Clin Invest.* 1998;102: 837–43. All studies were performed a minimum of 3 times.

Cardiac Allografts Transplant Studies

Cardiac angiogenic potential was measured by employing a cardiac allograft model, which allowed testing to restore angiogenic potential while controlling the age of the cardiac tissue being vascularized.

The cardiac allograft procedure involved transplanting a neonatal C57B61/L (24 hr old) murine heart into the pinnae of both syngeneic young adult (3 month old) and senescent (18 month old) murine hosts as described in Aird et al. *J. Cell Biol.* 1997: 138: 1117–24; Edelberg et al. *J Clin Invest.* 1998: 101: 337–43. The recipient mice were anesthetized with Avertin 2.5% (vol/vol) IP. After cleaning the dorsum of the pinna of the mouse ear with 70% ethanol, an incision penetrating only the epidermis, 2–5 mm in length, was made with a scalpel transverse to the longitudinal axis of the ear, 3–4 mm distal to its base on the skull. A small pocket between the skin and cartilage was then dissected with delicate curved forceps. The total donor neonatal heart was excised without the pericardial sac and inserted into the ear pocket. Gentle pressure with the tips of the forceps was applied to the ear to express air from the pocket and facilitate the adherence between donor and recipient tissues (n=20 three month old, n=17 eighteen month old).

As controls, senescent mice were transplanted with inert silicon (1×1×2 mm$^3$) (n=8) or neonatal pulmonary allografts (n=8) in place of the neonatal cardiac tissue. In addition, sets of senescent hosts were pretreated with subcutaneous pinnal injections of recombinant VEGF (R&D Systems; 100 ng/20 μL PBS) (n=12), recombinant PDGF AB (R & D Systems; 100 ng/20 μL PBS) (n=12) or vehicle alone (n=8) 1 day prior to receiving cardiac allograft transplants. In addition, at the time of cardiac or pulmonary allograft transplantation sets of young adult mice were also treated with single subcutaneous pinnal injections of antibodies to neutralize PDGF AB (10 μg in 20 μL PBS, AB-20-NA, R&D Systems; n=8 cardiac, 8 pulmonary allografts) or non-immune control rabbit IgG (10 μg in 20 μL PBS, AB-105-C, R&D Systems; n=8 cardiac, 8 pulmonary allografts). Allograft viability was scored by pinnal and transplant integrity. In addition, pinnal electrocardiograms were recorded as previously described to further document the viability of the cardiac allografts. Edelberg et al. *J Clin Invest.* 1998: 101: 337–43.

Auricular Angiogenesis Studies

Young adult (3 month old) and senescent mice (18 month old) received mid-pinnal injections of PDGF AB (100 ng/20 μL PBS) or PBS alone (n=8 for each group). Two days later the blood flow through both the middle and posterior auricular arteries was surgically interrupted by severing the base of the ear, thereby rendering the posterior auricular arterial circulation dependent on collateral flow from the intact anterior auricular artery, as previously described. Baker et al. 1999 *Br. J. Plast. Surg.* 52: 133–42. The functional blood flow to the posterior vascular bed was then assessed by laser Doppler with an Advance Laser Flowmeter ALF21/21D (Advance, Tokyo) as previously described. Rendell et al. 1998 *Microvasc. Res.* 55: 3–13.

Following completion of the rheology studies, the mice received intracardiac injections of lysine-fixable biotinylated-dextran (2×10$^6$ M.W.; 50 μL of 10$^{-5}$ M in PBS; Molecular Probes, Eugene Oreg.) to stain the perfused vasculature. Samples were fixed by 4% paraformaldehyde in PBS and then incubated with streptavidin-horse radish peroxidase and then developed with DAB. Histological measurements were performed with digital microscopy to assess functional vascular density of the posterior auricular vasculature as previously described. Thurston et al. 1999 *Science* 286: 2511–14.

Bone Marrow Transplantation

Bone marrow transplantation was performed as previously described. Spangrude et al. 1988 *Science* 241: 58–62. Briefly, 3 and 18 month old C57B1/6 mice, as well as 3-month-old B6.129S7-Gtrosa26 (Rosa-26) mice were used. Friedrich et al. 1991 *Genes Dev.* 5: 1513–23. These mice were sacrificed and tibias and femurs were removed and trimmed of muscle and extraossial tissue. All the cells in the Rosa-26 express LacZ, therefore transplantation of the Rosa-26 bone marrow into the wild-type isogeneic senescent hosts facilitated the identification of the transplanted cells by X-gal staining. The bones were cut proximally and distally, and the bone marrow flushed with 2% bovine serum albumin in PBS. The cellular pellets were washed with and resuspended in PBS. The bone marrow cells were then injected into intact, unirradiated wild-type 18-month-old host C57B1/6 mice by tail vein injection with 300 µL of cells (3 month old C57B1/6: $10^7$ cells, n=16; $10^6$, n=12; $10^5$, n=6; 18 month old C57B1/6, $10^7$, n=6; 3 month old Rosa-26, $10^7$, n=6). The survival rates of all mice transplanted with exogenous bone marrow was 100%. One week after bone marrow transplantation the mice received pinnal cardiac allografts as described above. Seven day later mice receiving Rosa-26 bone marrow were sacrificed and the bone marrow and exogenous cardiac tissue with surrounding pinnal tissue were sectioned and stained for β-galactosidase activity as well as von Willebrand factor as previously described. Aird et al. *J. Cell Biol.* 1997: 138: 1117–24.

Results

Induction of PDGF B is Impaired in Senescent Endothelial Cells

RT-PCR analysis revealed that PDGF A was expressed in ventricular myocardial samples from both the young adult and senescent heart. See FIG. 1A. PDGF B expression, however, was detected only in young adult cardiac samples (FIG. 1A) suggesting that endothelial expression of PDGF B may be down regulated in the senescent heart.

Cardiac endothelial cells were isolated from both 3 and 18 month old wild-type mice and then co-cultured in the presence of fetal cardiac myocytes by using the transwell procedure described above. Endothelial cells of both young and senescent hearts constitutively expressed PDGF A. See FIGS. 1A and B. PDGF α-receptor (PDGFRα) was also expressed in the endothelial cells from both the young adult and senescent hearts. See FIGS. 1B and 1C. However, only the young adult CMECs expressed PDGF B in the presence of the fetal cardiac myocytes. See FIG. 1B. A significant increase in protein levels of PDGF B was observed in CMECs from 3-month-old hearts but not from 18-month-old hearts. See FIGS. 1B and 1C.

In addition to the differences in PDGF B expression, the expression pattern of other pro-angiogenic genes was also altered in the CMECs from aging mice. See FIGS. 1B and C. Unlike the young adult CMECs in which VEGF was induced in the co-culture with the cardiac myocytes, the senescent heart-derived endothelial cells expressed VEGF when cultured in isolation. However, VEGF mRNA levels decreased in senescent CMEC when cardiac myocytes were present. Furthermore, the expression of Flk-1 (VEGFR-2), the principal mitogenic receptor for VEGF, was significantly reduced in the senescent cells. Collectively, these results suggest that a disruption in cell-to-cell communication may be a primary defect in the aging heart. In particular, aging CMECs do not appear to respond to cardiac myocytes in the same manner as young CMECs.

PDGF AB Restores Cardiac Angiogenesis in Pinnal Allograft Transplants

The potential functional significance of the dysregulation in cell-to-cell communication within senescent mouse heart tissues was then examined. These studies employed a syngeneic neonatal murine cardiac allograft-pinnal transplant model. Aird et al. *J. Cell Biol.* 1997:138: 1117–24. This model effectively recreates the organ bed specific regulation of endothelial cells recruited from host peripheral vascular beds (id.). In these studies, endogenous PDGF AB was either neutralized by injection of anti-PDGF AB antibodies or enhanced by addition of exogenous PDGF AB.

Table 1 illustrates that neutralization of PDGF AB by injection of anti-PDGF AB into the pinnae of young mice at the time of transplantation significantly reduced the viability of cardiac allografts (3/8 viable vs. 8/8 viable with control antibody, p<0.05). The viability of pulmonary transplant engraftment was unaltered by neutralization of PDGF AB (8/8 viable vs. 8/8 viable with control antibody). Similarly, injection of anti-PDGFR-α antibodies at the time of transplantation significantly reduced cardiac allograft viability. Hence, PDGF AB and PDGFR-α are needed for survival of cardiac allografts. PDGFR-α is believed to be the major receptor that mediates the PDGF pathway, whereas PDGFR-β may have only a minor role.

TABLE 1

PDGF AB is Needed for Survival of Pinnal Cardiac Allograft Antibody Pretreatment

| Pinnal allograft | IgG | Anti-PDGF-AB | Anti-PDGFR-α | Anti-PDGFR-β |
|---|---|---|---|---|
| Heart viability | 9/9 | 3/8* | 3/7† | 7/7 |
| Lung viability | 8/8 | 8/8 | ND | ND |

IgG indicates immunoglobulin G; ND, not determined.
*P < 0.05 vs. IgG heart and anti-PDGF-AB lung trials;
†P < 0.05 vs. IgG and anti-PDGFR-β heart trials.

Cardiac allograft survival was markedly impaired in the aging mice as compared to the young adult mice. See FIG. 2A. However, wound healing was preserved in the older hosts, as demonstrated by the integrity of silicon implants. The viability of the pulmonary allografts suggested that the aging-associated changes were due to diminished senescent endothelial angiogenic function.

Various molecular mediators that were observed to be down regulated in senescent cardiac tissues were then tested to ascertain whether these molecules could restore cardiac angiogenic potential in aging mice. The subcutaneous pinnal administration of VEGF failed to improve the success of cardiac transplantation in the aging mice. See FIG. 2A. However, injection of PDGF AB into senescent implantation sites restored the viability of senescent allografts to that of the young adult hosts. See FIG. 2A. These data suggest that an aging-associated decrease in endothelial cell PDGF B gene expression underlies the impaired function in senescent cardiac angiogenic potential observed in vivo. Moreover, in these studies the PDGF B expressed in the transplanted tissue appeared to be insufficient to induce effective vascularization in the senescent hosts.

Figure 2C:
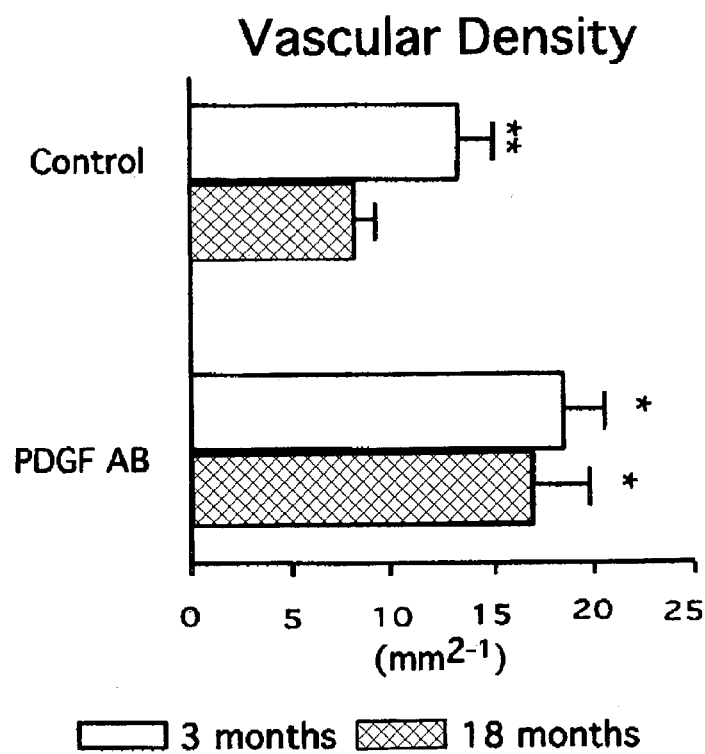
FIG. 2C provides a bar graph illustrating vascular density per square mm in untreated tissues and in tissues treated with PDGF AB. These results were obtained by histological measurements of vascular density in the posterior auricular circulation. Histological assessment confirmed that PDGF AB increased collateral vascular density in the pinnae of both the young and senescent mice.

In order to define the mechanism mediating the restoration of senescent angiogenic function, the direct effects of PDGF AB pretreatment on the pinnal vasculature of the aged mice were tested. In particular, the development of functional blood vessels in both young adult and senescent mice was assessed using the murine cardiac allograft model, where induction of angiogenesis is essential for cardiac engraftment. Laser Doppler measurements demonstrated that pretreatment with PDGF AB significantly increased blood flow in both the young as well as the older hosts. See FIG. 2B. In addition, histological assessment confirmed that the rheologic effects of PDGF AB were mediated by increasing collateral vascular density in the pinnae of both the young and senescent mice. See FIGS. 2B and 2C. These results suggest that PDGF AB restores the defects in senescent cardiac angiogenic function. Moreover, the auricular studies suggest that the PDGF AB rescue of the cardiac transplants is mediated by enhancing the vascular potential in the aging murine host.

Bone Marrow Endothelial Precursor Cells Restore Cardiac Angiogenic Function

Previous work suggested that some bone marrow-derived cells might be involved in post-natal angiogenesis. Shi et al. 1998 Blood 92: 362–67; Asahara et al. 1997 Science 275: 964–67; Kalka et al. 2000 Proc. Natl. Acad. Sci. U.S.A. 97:3422–27; Takahashi 1999 Nat. Med. 5: 434–38. Bone marrow endothelial precursor cells of young mice were tested to ascertain whether they could offer a novel means of restoring the PDGF-dependent angiogenic pathways in the aging vasculature. In particular, the capacity of young bone marrow endothelial precursor cells was tested to see whether they could reconstitute the critical cardiac myocyte-mediated PDGF regulatory pathways.

Figure 3A:
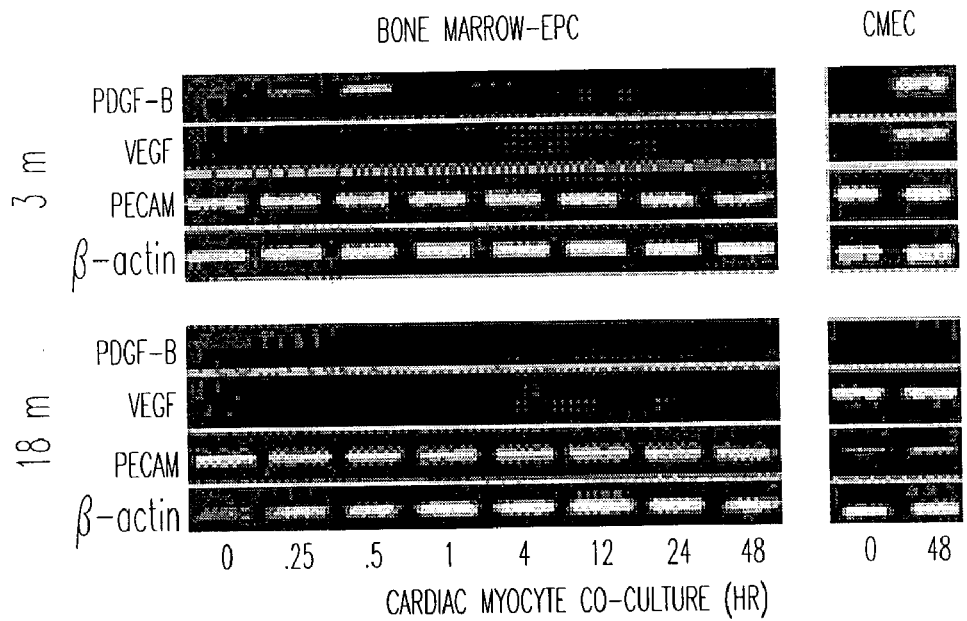
FIG. 3A illustrates the temporal gene expression profiles of bone marrow-derived endothelial precursor cells (EPCs) co-cultured for 0 to 48 hours with cardiac myocytes. By way of comparison, the temporal gene expression profiles of cardiac microvascular endothelial cells (CMECs) co-cultured for 0 and 48 hours with cardiac myocytes are shown. The top panels show the expression profiles of EPCs and CMECs isolated from 3-month-old mice, whereas the bottom panels show the expression profiles of EPCs and CMECs isolated from 18-month-old mice. As illustrated, the young EPCs and CMECs express PDGF B, whereas the older EPCs and CMECs do not.
Figure 3B:
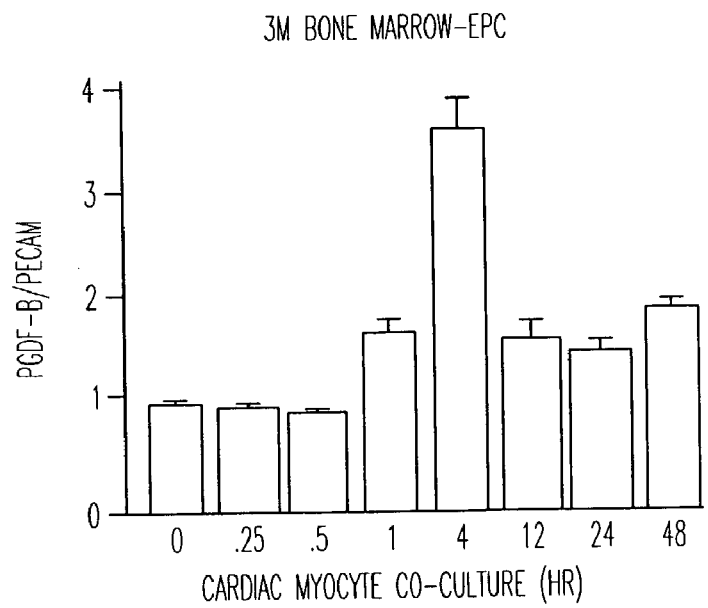
FIG. 3B provides a graph illustrating the PDGF-B/PECAM protein ratio in 3-month-old bone marrow-derived EPCs that were co-cultured with cardiac myocytes.

FIGS. 3A and 3B show that PDGF B expression was induced in young bone marrow endothelial precursor cells and in young cardiac microvascular endothelial cells when these cells were co-cultured with cardiac myocytes. However, no such induction of PDGF B expression was observed in older bone marrow or cardiac microvascular endothelial cells. See FIG. 3A. PDGF B expression was induced in these young cells within about one hour of exposure to cardiac myocytes.

Figure 3C:
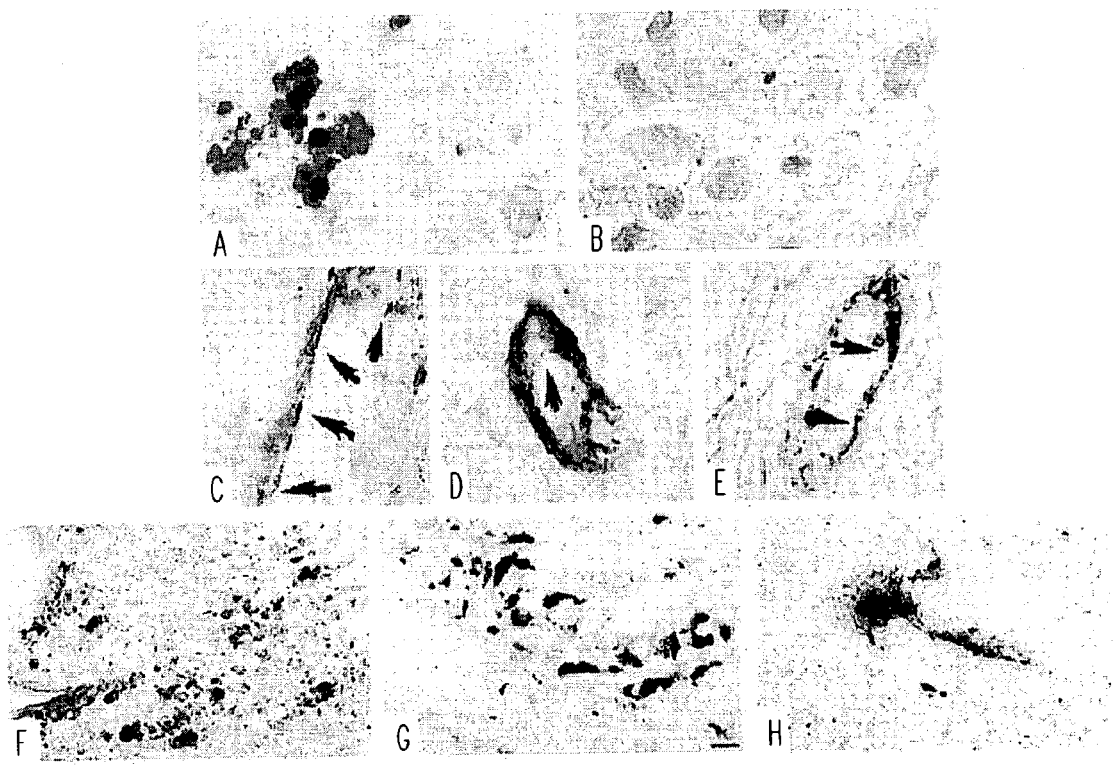
FIG. 3C provides representative photomicrographs of X-gal stained tissue sections from 18-month-old mice receiving $10^7$ bone marrow cells from 3-month-old Rosa-26 ($\beta$-galactosidase (+)) mice one week before cardiac engraftment. Aging wild-type host bone marrow with young transgenic cells (a), young transgenic cell incorporation in (b through e) and around (f and g) the wild-type cardiac myocardium transplanted into the aging hosts. Co-staining for von Willebrand factor of intraallograft with arrows highlighting transgenic cells (c through e) and periallograft pinnal tissue (g) and for PDGF-B of intraallograft tissue (h); bar=25 $\mu$m (a, b, f, and g) and 10 $\mu$m (c, d, e, and h).

Bone marrow from young LacZ+ Rosa-26 mice was then transplanted intravenously into intact, unirradiated older mice. Analysis of these mice revealed that β-galactosidase-positive cells were engrafted in the senescent (older) bone marrow. See FIG. 3C. FIG. 3C provides representative photomicrographs of X-gal stained tissue sections from 18-month-old mice that had received $10^7$ bone marrow cells from 3-month-old Rosa-26 (β-galactosidase (+)) mice one week before cardiac engraftment. The transplanted young bone marrow cells were incorporated both within and around the host cardiac myocardium (FIG. 3Cb–g). The bone marrow of older mice that had received young transgenic cells also stained positively for β-galactosidase (FIG. 3Ca). Cells within the allograft exhibited co-staining with both von Willebrand factor and β-galactosidase (arrows highlight the transgenic cells in FIGS. 3Cc through 3Ce). vWF is a marker for cardiac myocyte-endothelial PDGF communication. Edelberg et al. *J Clin Invest.* 1998;102: 837–43. Cells within the periallograft pinnal tissue also co-stained with both von Willebrand factor and β-galactosidase (FIG. 3Cg). Cells within the allograft also stained positively for PDGF-B (FIG. 3Ch). Hence, β-galactosidase-positive bone marrow endothelial precursor cells that co-stained with von Willebrand factor were recruited into the vascularization of the cardiac allografts in the peri-and intra-allograft microvasculature. See FIG. 3C(c–e, g). Bone marrow endothelial precursor cells that co-stained with β-galactosidase and PDGF-B were also recruited into the vascularization of the cardiac allografts in the intra-allograft microvasculature. See FIG. 3C(h).

Figure 3D:
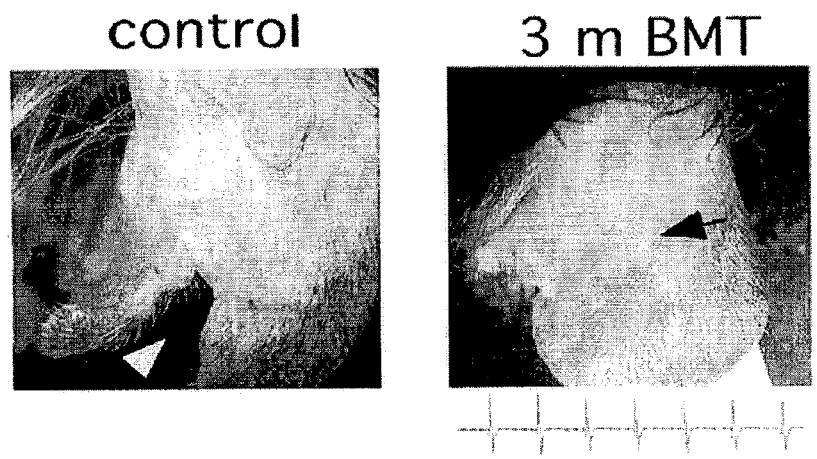
FIG. 3D provides representative examples of pinnal cardiac allografts in 18-month-old hosts with either no bone marrow transplantation (control) or $10^7$ bone marrow cells from 3-month-old donor (BMT) one week before cardiac engraftment. The arrow indicates the location of the viable cardiac allograft. The arrowhead provides the location of necrotic loss for both cardiac allograft and host pinnal tissue.
Figure 3E:
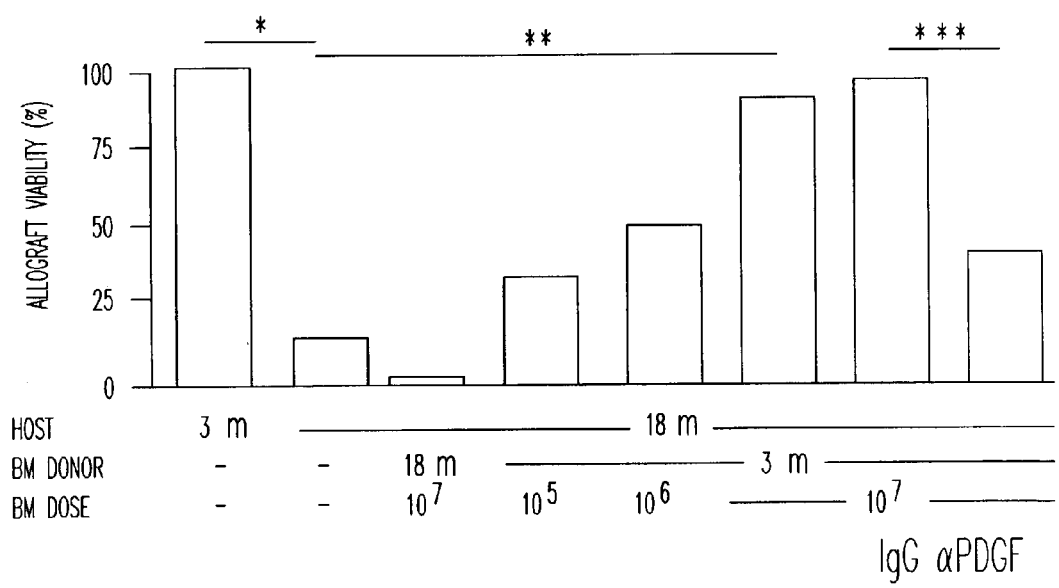
FIG. 3E provides a bar graph illustrating the viability of cardiac allografts in young and senescent control hosts (3-month-old, 8/8; 18-month-old, 1/8) and senescent hosts receiving bone marrow cells isolated from 18-month-old donors ($10^7$ cells, 0/6), and from 3-month-old donors ($10^5$ cells, 2/6; $10^6$ cells, 6/12; and $10^7$ cells, 15/16) alone or with pinnal antibody pretreatment (IgG, 7/7; anti-PDGF-AB, 3/7). *$P<0.05$ 3-month-old vs. 18-month-old transplant hosts; $P<0.05$ 18-month-old hosts control vs. transplantation with 3 month-old bone marrow; *$P<0.05$ IgG vs. anti-PDGF AB.

Remarkably, transplantation of bone marrow from 3-month-old mice into intact aging murine hosts maintained the viability and restored the functioning of the exogenous cardiac tissue. See FIG. 3D. However, transplantation of bone marrow from 18-month-old mice failed to reverse the aging-associated decline in cardiac angiogenic function. See FIGS. 3D and 3E. The restoration of the senescent vascular function was a dose dependent response in that the more young bone marrow cells transplanted, the better the viability of the allograft. See FIG. 3E. These data suggest that a subpopulation of the cells that give rise to BM endothelial precursor cells mediates the in vivo reconstitution of the cardiac microvascular communication.

PDGF-AB Protects the Endogenous Heart from Myocardial Infarction

Experiments were conducted to ascertain whether PDGF-AB pretreatment could significantly reduce the extent of myocardial infarction after LAD ligation. Quantification of myocardial infarction size by Masson's trichrome stain revealed that PDGF-AB reduced the size of myocardial infarction by approximately half in the young adults (FIG. 4A and 4B). Similarly, the infarction size in 24-month-old heart pre-injected with PDGF-AB was approximately half the size of infarctions in control-injected hearts (FIG. 4C and 4D). Treatment at the time of coronary ligation, however, had no effect on myocardial infarction size (15.7±3.1%; n=3). Hence, a period of pretreatment may be needed.

EXAMPLE 2

PDGF-AB Stimulates Cardiac Myocyte Derivation from Aging Bone Marrow

This Example provides data illustrating that aging bone marrow cells failed to generate cardiac myocytes and fail to express PDGF-B. However, addition of PDGF-AB restored the cardioplastic potential of aging bone marrow cells and stimulated formation of functional cardiac myocytes that expressed myosin heavy chain and exhibited chronotropic activity in vivo.

Methods

Cell Isolation and Culture

Bone marrow cells were isolated from 3 and 18 month-old wild-type C57B1/6 mice (Harlan Sprague-Dawley, Indianapolis, Ind.; n=3 each). The mice were sacrificed and the tibias and femurs removed and cut proximally and distally. The bone marrow was flushed with 2% BSA in PBS. The cellular pellets were washed with PBS and plated into 12-well dishes with Iscove's Modified Dulbecco's Medium supplemented with 10% fetal calf serum, 50 µg/mL heparin, 100 µg/mL penicillin, 100 µg/mL streptomycin, 5 ng/mL fibroblast growth factor-2, and 10 ng/mL vascular endothelial growth factor. Additional studies were performed with and without supplemented of PDGF-AB (R&D Systems, 10 ng/mL).

Motion Analysis

Live cells were examined and recorded in real-time under phase microscopy using a Nikon TE 200 inverted microscope equipped with an Orca ER digital camera and imaging software (Simple PCI, Compix). Movies were exported in AVI format. In addition, single frames were obtained to measure systolic and diastolic diameters ($D_s$ and $D_d$, respectively), in order to calculate changes in cell volume ($\Delta V = [(D_d^3 - D_s^3)/D_d^3]*100\%$, n=10)

Immunostaining

At the termination of the bone marrow cultures the cells were methanol fixed and stained with monoclonal antibodies for Troponin-T (cardiac isoform) (Clone 13-11, Neomarkers). Immune complexes were visualized using a Vectastain Elite ABC-Nova Red (Vector Laboratories).

Molecular Studies

Total RNA was isolated from individual wells at weekly intervals for 4 weeks (RNeasy, Qiagen) and cDNA was synthesized (Sensicript Reverse Transcriptase, Qiagen). Semi-quantitative PCR was then performed in triplicate using the following primers:

```
β-actin:
(forward)
5'GTGGGCCGCTCTAGGCACCAA3',      (SEQ ID NO:23)

(reverse)
5'CTCTTTGATGTCACGCACGATTTC3';   (SEQ ID NO:24)

PDGF-A:
(forward)
5'TCAAGGTGGCCAAAGTGGAG3',       (SEQ ID NO:25)

(reverse)
5'CTCTCTGTGACAAGGAAGCT3';       (SEQ ID NO:26)

PDGF-B:
(forward)
5'ATCGCCGAGTGCAAGACGCG3',       (SEQ ID NO:27)

(reverse)
5'AAGCACCATTGGCCGTCCGA3';       (SEQ ID NO:28)

von Willebrand Factor (vWF):
(forward):
5'TGTCCAAGGTCTGAAGAAGA3',       (SEQ ID NO:29)

(reverse):
5'CAGGACAAACACCACATCCA3';       (SEQ ID NO:30)

PECAM:
(forward):
5'CAAGCGGTCGTGAATGACAC3',       (SEQ ID NO:31)

(reverse):
5'CACTGCCTTGACTGTCTTAAG3';      (SEQ ID NO:32)

αMHC:
(forward):
5'GGAAGAGTGAGCGGCCATCAAGG3',    (SEQ ID NO:33)

(reverse):
5'CTGCTGGAGAGGTTATTCCTCG3'.     (SEQ ID NO:34)
```

Cardiac Myocyte Chronotropic Analysis

In order to assess phenotypic in vivo cardiac chronotropic activity, bone marrow-derived cardiac myocyte aggregates derived from 3 and 18-month-old murine bone marrow cells were transplanted into syngeneic adult hosts as previously described (n=5 each). Edelberg et al. (2002) *J Appl Physiol.* 92:581–5. Briefly, sets of mice were anesthetized with Avertin IP and prepared for aggregate engraftment by subcutaneous pinnal injections of PDGF-AB (20 ng/20 µL PBS). The following day, myocyte aggregates were physically dissociated and suspended in PBS ($5 \times 10^4$ cells/20 µL). These suspensions were transferred into a subdermal pinnal pocket, which was then sealed via gentle pressure with forceps. Electrocardiographic (ECG) activity of the endogenous heart and transplanted aggregates to assess chronotropic activity was performed 5–7 days post-transplantation following anesthetization with Avertin IP. ECG data was acquired as previously described. Christini et al. *Amer J Physiol.* 2001 ;280:H2006–2010. Following baseline recordings, chronotropic adenergic responsiveness was measured through local administration of isoproterenol (100 ng/10 µL PBS). Statistical significance was determined by student's t-test.

Results

Cardioplastic Potential of Young Bone Marrow Cells

Figure 5:
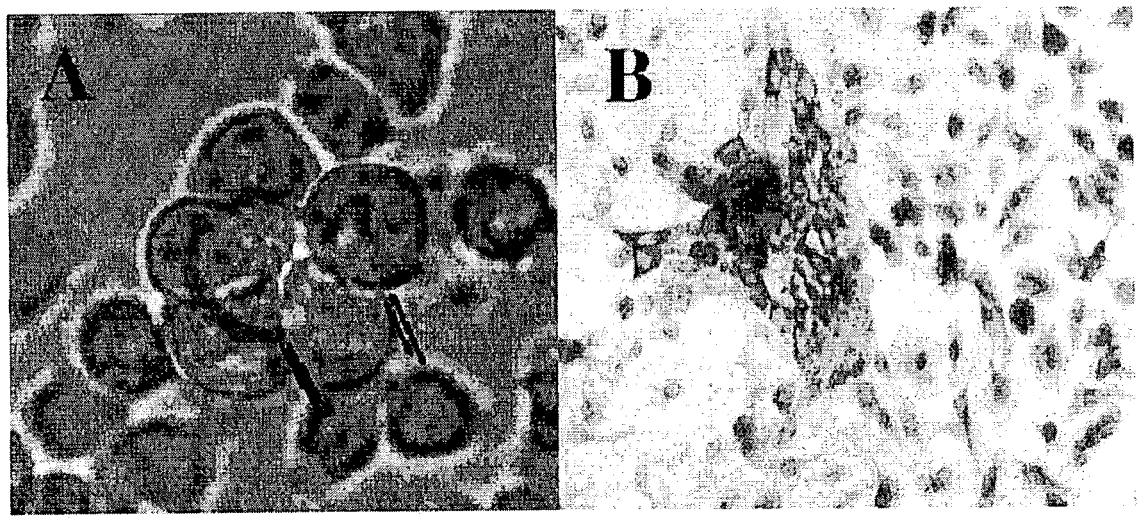
FIG. 5A provides a photomicrograph of a representative 3-month-old bone marrow-derived cardiac myocyte aggregate that exhibited spontaneous chronotropy after 4 weeks of tissue culture: parallel bars represent single cell diastole (outside bars) and systole (inside bars) (15±4% cell volume change) (bar=10 $\mu$m) (movie on disc).
FIG. 5B provides a photomicrograph of representative 3-month-old bone marrow-derived cell cultures immunostained for troponin T (bar=25 $\mu$m).

Bone marrow cells harvested from 3-month old mice grown under conditions supporting endothelial cells developed spontaneous chronotropic activity indicative of cardiac myocyte cultures (FIG. 5A). Bone marrow cells harvested from 18-month old mice grown under similar conditions did not exhibit such chronotropic activity. The cardioplastic potential of the young bone marrow cultures was further evidenced by immunostaining for troponin T (FIG. 5B), however, older bone marrow cultures did not stain positively for troponin T. These results indicate that the molecular pathways regulating the differentiation of cardiac myocytes from the aging bone marrow are impaired.

In order to develop strategies to restore the generation of cardiac myocytes from aging bone marrow cells, older bone marrow cells were exposed to factors involved in the cardiac myocyte-endothelial communication pathway. Molecular analysis revealed that PDGF isoforms were induced at the same time as cardiac myocyte-specific α myosin heavy chain (αMHC), however, vWF was expressed after PDGF and αMHC (FIG. 6A). vWF is a marker for cardiac myocyte-endothelial PDGF communication. Edelberg et al. *J Clin Invest.* 1998; 102:837–43. Addition of PDGF-AB increased the kinetics of cardiac myocyte generation as evidenced by αMHC expression in half the time of the bone marrow cells cultured in the absence of unsupplemented media (FIG. 6B).

The in vivo viability of the bone marrow-derived cardiac myocytes was confirmed by transplantation of the cells into pinna of syngeneic mice. After transplantation, electropotential signals were observed from the bone marrow-derived cardiac myocyte aggregates. Greater than 80% increase in chronotropic activity was observed (226+/−60 vs. 120+/−18 depolarizations/min, baseline, p<0.05) (FIG. 7C).

Restoring Cardioplastic Potential of Aging Bone Marrow Cells

Figure 6A:
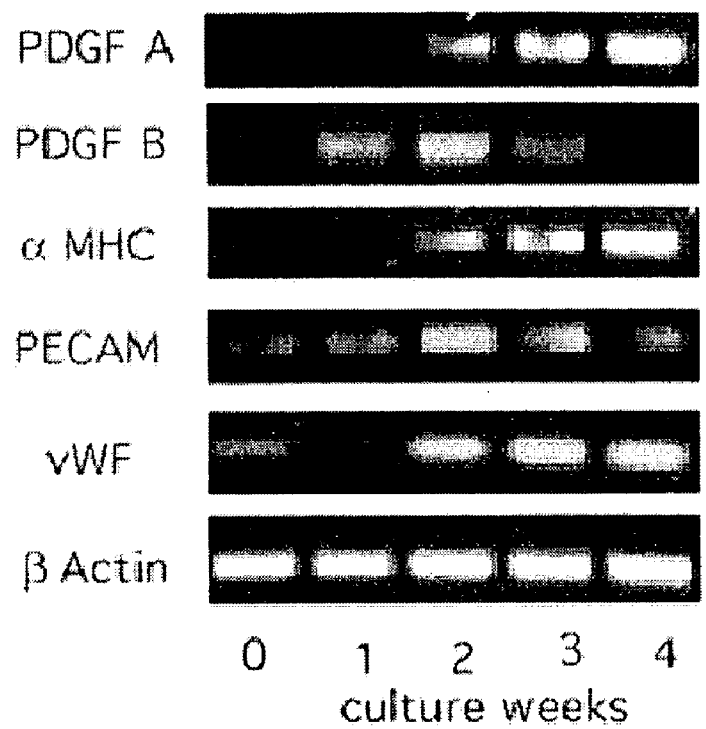
FIG. 6A provides a representative gel of RT-PCR products illustrating temporal gene expression of 3-month-old bone marrow-derived cells.
Figure 6B:
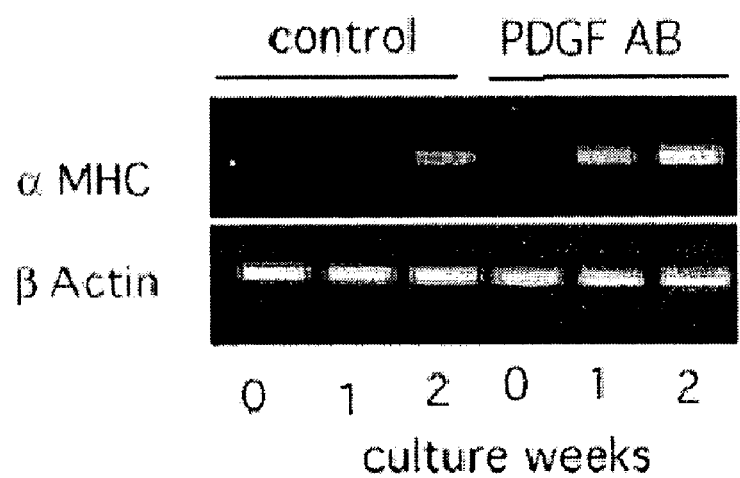
FIG. 6B provides a representative gel of RT-PCR products illustrating temporal gene expression of 3-month-old bone marrow-derived cells in the presence and absence of exogenous PDGF.
Figure 6C:
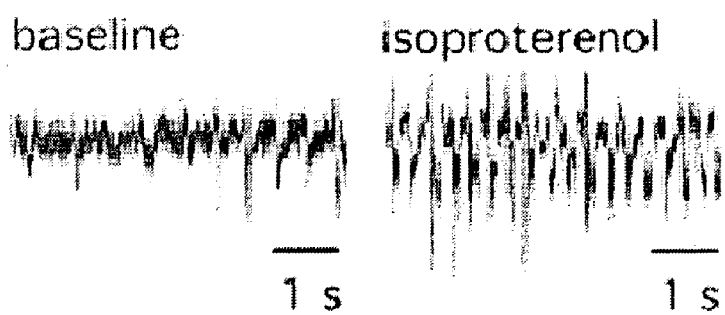
FIG. 6C provides a representative graph of in vivo chronotropic activity as a function of time in a 3-month-old bone marrow-derived cardiac myocyte before and after adrenergic stimulation.
Figure 7A:
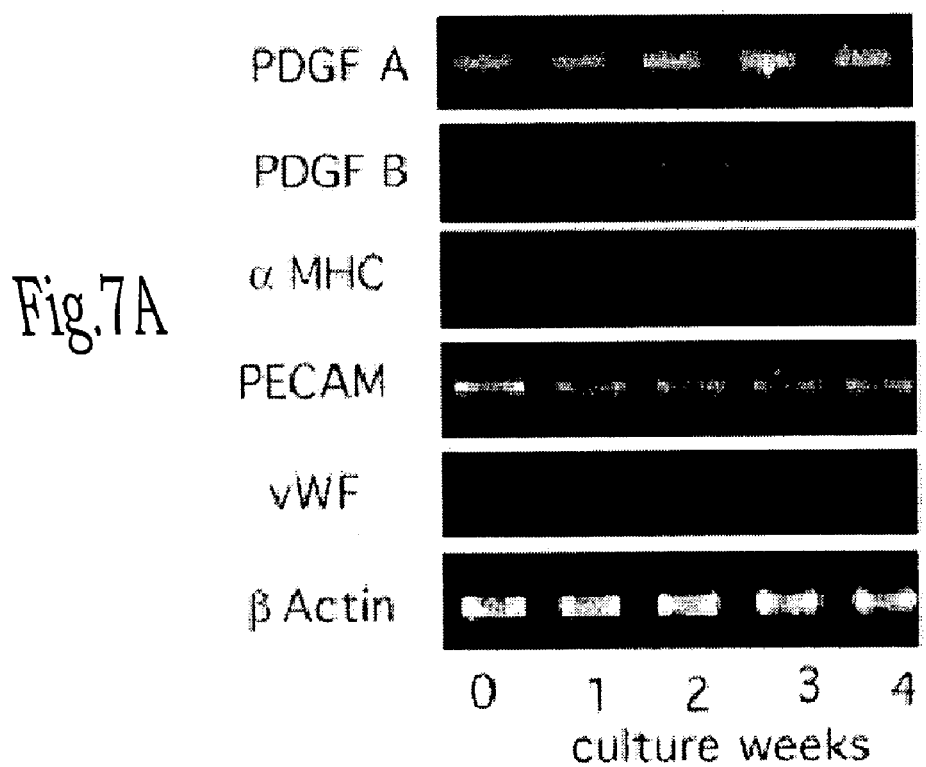
FIG. 7A provides a representative gel of RT-PCR products illustrating temporal gene expression profiles of 18-month-old bone marrow-derived cells.
Figure 7B:
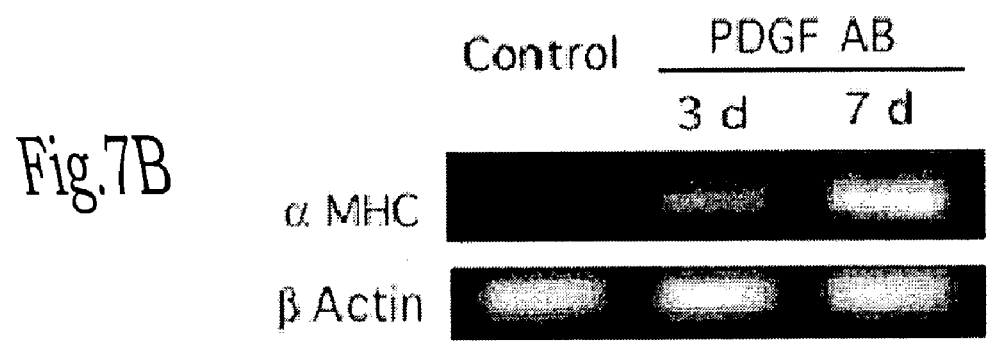
FIG. 7B provides a representative gel of RT-PCR products illustrating $\alpha$MHC expression in 18-month-old bone marrow-derived cells in the presence and absence (control) of exogenous PDGF. As a further control, $\beta$-actin expression was also observed FIG. 7C provides a representative graph of in vivo chronotropic activity as a function of time in a PDGF-induced 18-month-old bone marrow-derived cardiac myocyte before and after adrenergic stimulation.
Figure 7C:
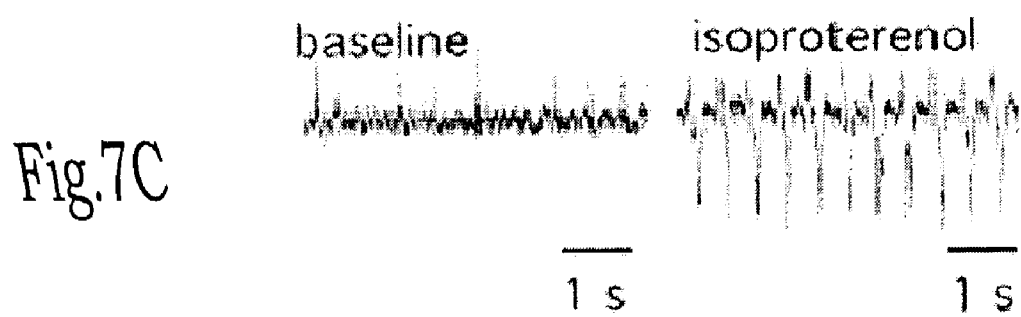

Unlike young bone marrow, cells derived from the aging bone marrow did not express PDGF-B, αMHC, or vWF (compare FIG. 6A and FIG. 7A). However, as shown FIG. 7B, 18-month-old bone marrow cultured in the presence of exogenous PDGF-AB did express αMHC. Moreover, the resultant cardiac myocyte aggregates derived from these cultures demonstrated phenotypic electrocardiographic activity in vivo (see FIGS. 6C and 7C). Greater than a 60% fold increase in chronotropic activity was observed in 18-month-old bone marrow cultured in the presence of exogenous PDGF-AB (137+/−10 depolarizations/min, baseline,) compared to 18-month-old bone marrow cultured in the absence of exogenous PDGF-AB (83+/−24 depolarizations/min, baseline, p<0.05)(FIG. 7C).

These results indicate: (1) PDGF mediates the generation of cardiac myocytes from young bone marrow, (2) when PDGF-B induction does not occur in aging bone marrow cells, cardiac myocyte generation is impaired, and (3) addition of exogenous PDGF can stimulate and/or restore myocyte generation from bone marrow cells.

EXAMPLE 3

Transplanted Genetically-Modified Endothelial Precursor Cells are Incorporated and Participate in Neovascularization of Syngeneic Adult Cows This Example describes experiments where a marker gene was inserted into the genome of primary cultures of bovine fibroblasts, the fibroblasts were fused with enucleated bovine oocytes, and fetal liver cells were isolated from the resulting embryos. After these fetal liver cells were injected intravenously into syngeneic adult cows, the marker gene was detected in the vascular endothelium of the cows.

Methods

Fibroblast Isolation

General procedures were employed for isolating and growing fibroblast cells from skin and lung tissue. See, for example, U.S. Pat. No. 6,011,197 (Strelchenko et al.), and in U.S. Pat. No. 5,945,577 (Stice et al.), the contents of both of which are incorporated herein by reference in their entirety.

The methods employed were generally as follows. Minced tissue was incubated overnight at 10° C. in trypsin EDTA solution (0.05% trypsin/0.02% EDTA; GIBCO, Grand Island, N.Y.). The following day, tissue and any disassociated cells were incubated for one hour at 37° C. in pre-warmed trypsin-EDTA solution (0.05% trypsin/0.02% EDTA; GIBCO, Grand Island, N.Y.) and subjected to three consecutive washes and further trypsin incubations of one hour. Fibroblast cells were then plated in tissue culture dishes and cultured in alpha-MEM medium (Bio Whittaker, Walkersville, Md.) supplemented with 10% fetal calf serum (FCS) (Hyclone, Logen, Utah), penicillin (100 IU/ml) and streptomycin (50 µl/ml).

Such fibroblast cells can be isolated at virtually any time in development, ranging from approximately post embryonic disc stage through adult life of the animal (for example, for bovine animals, from day 12 to 15 after fertilization to 10 to 15 years of age).

Genetic Modification of Nuclear Transfer Donor Cells

Culture plates containing propagating fibroblast cells were incubated in trypsin EDTA solution (0.05% trypsin/0.02% EDTA; GIBCO, Grand Island, N.Y.) until the cells were in a single cell suspension. The cells were spun down at 500×g and re-suspended at 5 million cells per ml with phosphate buffered saline (PBS). A reporter gene construct containing the cytomegalovirus promoter operably linked to a beta-galactosidase, neomycin phosphotransferase fusion gene (beta-GEO) is added to the cells in the electroporation chamber at 50 µg/ml final concentration. After providing a standard electroporation pulse, the fibroblast cells were transferred back into the growth medium (alpha-MEM medium (BioWhittaker, Walkersville, Md.) supplemented with 10% fetal calf serum (FCS) (Hyclone, Logen, Utah), penicillin (100 IU/ml) and streptomycin (50 µl/ml)).

The day after electroporation, attached fibroblast cells were selected for stable integration of the reporter gene by culturing them for up to 15 days in growth medium containing G418 (400 µg/ml). The neomycin phosphotransferase portion of the beta-GEO gene confers resistance to G418, and cells that do not contain and express the beta-GEO gene are killed by the selection procedure. At the end of the selection period, colonies of stable transgenic cells were present. Each colony was propagated independently of the others. Transgenic fibroblast cells were stained with X-gal to observe expression of beta-galactosidase, and genomic integration of the expression construct was confirmed by PCR amplification of the beta-GEO gene and analysis using agarose gel electrophoresis.

Cloning by Nuclear Transfer, with Transgenic Fibroblasts as Nuclear Donors

The stably transfected Neo$^r$ fibroblast cells described above were used as nuclear donors for nuclear transfer into enucleated oocytes using procedures available in the art. See U.S. Pat. No. 6,147,276 (Campbell et al.); U.S. Pat. Nos. 5,945,577 and 6,235,969 of Stice et al.

Oocytes were isolated from bovine ovaries and stripped of cumulus cells to prepare for nuclear transfer. Enucleation of the recipient oocyte was performed after the oocyte attained the metaphase II stage with a beveled micropipette at approximately 18 to 24 hrs post maturation (hpm). Such enucleation can be carried out before or after nuclear transfer. Enucleation was confirmed in TL-HEPES medium plus Hoechst 33342 (3 µg/ml; Sigma). Individual donor cells (fibroblasts) were then placed in the perivitelline space of the recipient oocyte, and the oocyte and donor cell were fused together to form a single cell (a nuclear transfer unit) using a single one fusion pulse consisting of 120 V for 15 µsec to the nuclear transfer unit in a 500 µm gap chamber. In some experiments, nuclear transfer and electrofusion was performed at 24 hrs post maturation. The nuclear transfer units were then incubated in CR1aa medium.

Nuclear transfer units were activated as described in U.S. application Ser. No. 09/467,076 (Cibelli et al.), filed Dec. 20, 1999 now abandoned, the contents of which are incorporated herein by reference in their entirety. Following activation, the nuclear transfer units were washed and cultured under conditions that promote growth of the nuclear transfer unit to from 2 to about 400 cells. In particular, the nuclear transfer units were transferred to the wells of plates containing a confluent feeder layer of mouse embryonic fibroblasts as described in U.S. Pat. No. 5,945,577. After multicellular embryos were formed, they were implanted into cows to develop into fetal animals.

In the case of human applications, this example would apply in every respect with the exception that the human endothelial precursor cell would be produced from cloned human embryonic stem cells derived from pre-implantation (<14 day-old) embryos. The nuclear transfer units can be incubated until they reach the blastocyst stage, and the inner cell mass (ICM) cells of these nuclear transfer units can be isolated and cultured in the presence or absence of a feeder layer to generate pluripotent or totipotent embryonic stem cells.

The fetal calves were aborted, and fetal liver cells were isolated and injected intravenously into syngeneic adult cows. That is, in each transplant, the cloned, transplanted cells were administered to the same animal from which the donor fibroblasts used to generate the transplanted cells were originally obtained. At 414 days post transplantation, arterial tissue was removed from one of the treated cows (animal # 31) and endothelial cells from the arterial tissue were isolated and expanded. The endothelial cell outgrowths were analyzed to detect cells containing the transgene (Neo$^r$).

Transplanted Cells Participate in Neovascularization in a Transplant Recipient

Bovine fibroblasts were isolated and stably transfected with a recombinant DNA construct comprising a Neo$^r$ gene under control of a CMV promoter; stably transfected fibroblasts were cloned by nuclear transfer to generate multicellular bovine embryos; and these were implanted into cows to develop into fetal animals, as described above. Transgenic fetuses were aborted and fetal liver/bone marrow cells were isolated and intravenously injected into an adult cow (animal #33), also as described above.

Matrigel (BD) was defrosted overnight in 4° C., and aliquots of 20 ml were mixed with 2 micrograms heparin (Sigma) and 4 micrograms human vascular endothelial growth factor (PeproTech). Matrigel is a basement membrane extract. It is polymerizable into a rigid stable gel upon heating at 24°–37° C. A more complete discussion of Matrigel can be found in U.S. Pat. No. 4,829,000. The Matrigel mixture was injected with pre-cooled syringe subcutaneously at a suitable site. During injection of the Matrigel, the needle was kept in place for approximately 5 min. while lifting up the skin with the needle point, in order to allow the Matrigel to solidify as a plug.

After 14–21 days the animal was sacrificed and the Matrigel plugs are removed and cut into two portions. One part of the plug was fixed in 4% paraformaldehyde, embedded in paraffin, sectioned, and H & E stained. Sections were examined by light microscopy, and the number of blood vessels that have formed in the plug was evaluated. The other part of the Matrigel plug was digested by addition of Dispase (Invitrogen) for 5–10 minutes at 37° C. until the gel was liquefied and cells were released. The cells were expanded in-vitro and were evaluated to determine their cell type and to detect cells that have the Neo$^r$ transgene. Other tissues of the cow, e.g., bone marrow, endothelium, lymph node, etc. were also analyzed to detect and identify cells that have a Neo$^r$ transgene.

Results

Transplanted cells are incorporated into the vascular endothelium of a transplant recipient At 414 days post transplantation, arterial tissue was removed from one of the cows treated with Neo$^r$ endothelial precursor cells (animal #31) and endothelial cells from the arterial tissue were isolated and expanded. The endothelial cell outgrowths were analyzed to detect cells containing the transgene (Neo$^r$). Of five separate endothelial cell outgrowths, one of them (20%) was positive for the Neo$^r$ gene.

Bone marrow stem cells of a cow that received the transplant were isolated and cultured to form primary hematopoietic colonies. Eight pools were made of cells from the primary hematopoietic colonies, each pool consisting of cells from about 40 colonies, and the pools were tested for the presence of cells containing the Neo$^r$ transgene. Two of the eight pools tested positive for the Neor transgene, indicating that approximately 1–2% of the hematopoietic stem cells in the cow's bone marrow were derived from the transplanted transgenic cells. Neo$^r$ positive cells were also detected in the lymph nodes of the cow that received the transplant.

These results indicate that transplanted transgenic, nuclear transfer-derived hematopoietic stem cells are not rejected by a syngeneic recipient mammal that has an intact and functioning immune system, even though they have heterologous mitochondria. These results also demonstrate that the transplanted cells become established in the bone marrow and lymph tissue of the transplant recipient and give rise to differentiated endothelial precursor cells that incorporate into the vascular endothelium of the transplant recipient. Thus, immune rejection of stem cells need not be a problem, and stem cells can repopulate the vascular endothelium to facilitate repair and rejuvenation of the aging vascular system of mammalian tissues.

EXAMPLE 4

Transplantation and Engrafting of Genetically Modified Murine Endothelial Cells

This Example shows that fetal liver hematopoietic stem cells possess the ability to transdifferentiate and repair damaged tissue (infarcted myocardium) at the site of injection while expressing a transgenic marker gene, and differentiate into vascular endothelium.

Methods

The methods employed generally involve isolating somatic cells from 129/SV EV mice and genetically modifying the cells by insertion of an expression construct directing expression of the LacZ gene into their genomic DNA. Such transgenic murine cells were then used as nuclear donor cells, and cloned, transgenic fetal mice carrying the LacZ gene were produced by somatic cell nuclear transfer.

The methods employed are described in more detail below. Methods for cloning mice by somatic cell nuclear transfer are provided in Wakayama et al., 1998, "Full-term development of mice from enucleated oocytes injected with cumulus cell nuclei," Nature 394:369–374, the contents of which are incorporated herein by reference in their entirety. Methods employed for culturing murine blastocysts produced nuclear transfer to generate an isogenic embryonic stem cell line, for genetically modifying the nuclear transfer-derived embryonic stem cells by homologous recombination, and for inducing the genetically modified embryonic stem cells to differentiate in vitro to form hematopoietic precursors that can be therapeutically engrafted into mice in need of the transplant were similar to those described in Rideout, 3rd, et al., "Correction of a genetic defect by nuclear transplantation and combined cell and gene therapy," 2002, Cell, 109(1):17–27; the contents of which are incorporated herein by reference in their entirety.

Nuclear Transfer and Embryo Culture

Cloned 129/Sv-ROSA26::LacZ fetuses were produced by piezo-actuated microinjection (Prime Tech, Japan) essentially as described previously (Wakayama et al., 1998, nature 394:369–74; Wakayama and Yanagimachi, 1999, Nature Genetics, 22:127). Nucleus donor cells were isolated from primary cultures derived from tail tip biopsies of 8-week-old 129/Sv-ROSA26::lacZ males and cultured at 37° C. in 5% (v/v) $CO_2$ in humidified air in gelatin-coated 3.5 cm$^2$ flasks for 10–14 days in Dulbecco's modified ES medium (DMEM; GIBCO) supplemented with 15% (v/v) FCS. Immediately prior to use, cells were dissociated by treatment with trypsin and the reaction quenched by the addition of DMEM prior to washing three times in PBS. A 1–3 ml aliquot of the resultant nucleus donor cell suspension was mixed with a 10–20 ml drop of HEPES-buffered CZB containing polyvinylpyrrolidone (Mr 360,000) and the nuclei were injected into enucleated B6D2FT oocytes within 1 h of mixing. After approximately one hour, nuclear transfer oocytes were activated by exposure to $SrCl_2$ for 1 h and then incubated in KSOM (Specialty Media, N.J.) lacking $SrCl_2$ at 37° C. in 5% (v/v) $CO_2$ in humidified air (Wakayama et al., 1998). Cleaved (2-cell) embryos were transferred the next day (E1.5) to the oviducts of pseudopregnant CD1 surrogate mothers. Cloned fetuses recovered at 11 to 13 days gestation were used as a source of liver cells.

Isolation of c-Kit Positive Liver Cells

On two separate occasions cloned embryos were obtained. In the first instance, a group of four embryos at 12–13 days gestation were obtained and in the second instance, two embryos at 11 and 13 days gestation were obtained. Embryonic liver cells were obtained by mechanically disaggregating embryos though a 40 micrometer cell strainer (Becton Dickinson, Franklin Lakes, N.J.) and selected for c-kit+ cells. A total of $1.67 \times 10^7$ nucleated cells were obtained after disaggregation from the first group, and $5.8 \times 10^6$ cells were obtained from the second group. Cells were incubated with PE-conjugated anti-c-kit antibody (BD Pharmingen, San Diego, Calif.), and sorted on a MoFlow cell sorter (Dako Cytomation, Fort Collins, Colo.). In the first study $5 \times 10^5$ c-kit+ cells were obtained, and in the second study, $1.95 \times 10^5$ c-kit+ cells were obtained. The cells were suspended in 1 ml phosphate buffered saline with 10% fetal calf serum at 4° C.

The c-kit-positive fetal liver hematopoietic stem cells were injected into adult mice suffering from myocardial infarction. Prior to injection of the fetal cells, myocardial infarction was induced in adult 129 SV EV mice by occlusion of the left descending coronary artery near its origin. Four to six hours later, approximately 10,000 c-kit-positive fetal liver cells were injected at each of two sites in opposite regions of the border zone, adjacent to the non-contracting dead portion of the left ventricular wall (n=10). Control groups consisted of untreated infarcted mice (n=0) and sham-operated animals (n=9).

Results

The three groups of treated, untreated and sham-operated mice were sacrificed one month after surgery or sham operation. Infarct size was measured by the fraction of myocytes lost by the entire left ventricle inclusive of the interventricular septum. The dimension of the infarct was similar in the two groups of mice exposed to permanent coronary artery ligation. In the treated animals, infarct size was 56±5%, for which the total number of myocytes was $2.72 \pm 0.30 \times 10^6$, and the number of myocytes lost was $1.54 \pm 0.13 \times 10^6$. In the untreated animals, infarct size was 54±6%, for which the total number of myocytes was $2.72 \pm 0.30 \times 10^6$, and the number of myocytes lost was $1.48 \pm 0.15 \times 10^6$.

In the untreated mice at one month after surgery, the healing process was completed and the area of infarcted myocardium was a compact scarred area. Analysis of the connective tissue present in the scarred area identified the presence of both collagen type III and collagen type I.

In contrast, myocardial regeneration within the infarct occurred in all mice injected with fetal liver cells. Newly formed myocytes were recognized by the expression of Î±-sarcomeric actin, cardiac myosin heavy chain, connexin 43, and N-cadherin antibody labeling. Importantly, the developed myocardium also possessed coronary capillaries, which were identified by factor VIII antibody and Griffonia simplicifolia lectin labeling. Coronary resistance arterioles were numerous and were detected by Î±-smooth muscle actin antibody staining. The arterioles and capillaries contained in their lumen red blood cells, which were stained by TER-119 antibody. The presence of red blood cells in the lumen strongly suggested that the generated vessels were connected with the primary coronary circulation. Labeling with β-galactosidase antibody documented that these new structures, including myocytes, endothelial cells and smooth muscle cells, were all β-galactosidase-positive and were of fetal liver cell origin.

LacZ gene expression was assayed at the site of injection in both the myocardium and the endothelium. Most of the LacZ gene-containing cells that were detected in the repaired tissue were myocardial, but endothelial cells containing the LacZ were detected as well.

Quantitatively, in mice treated with fetal liver cells, the band of regenerated myocardium had an average volume of $7.4 \pm 3.0$ mm$^3$ and occupied 38±11% of the infarcted scarred tissue. Together, $8.2 \pm 2.6 \times 10^6$ new myocytes were formed. The volume of these myocytes varied from 200 to 2,700 μm$^3$, averaging 690±160 μm$^3$. There were 250±60 capillaries and 30±10 arterioles per mm$^2$ of reconstituted myocardium. The extent of tissue replacement reduced the size of the infarct by 18%, from 56 to 46% of the entire left ventricle. The reduction of infarct size was not sufficient to attenuate the remodeling of the post-infarcted heart. Chamber diameter, chamber volume, the wall thickness-to-chamber radius ratio and the left ventricular mass-to-chamber volume ratio were not statistically different from those evaluated in infarcted untreated mice. However, measurements of hemodynamic parameters obtained before sacrifice in the closed-chest preparation showed an improvement of left ventricular end-diastolic pressure in infarcted mice with myocardial regeneration induced by the injection of fetal liver cells. Additionally, diastolic wall stress was reduced by nearly 30% in this group. Thus, fetal liver cells regenerate infarcted myocardium and ameliorate the diastolic properties of the infarcted ventricle.

REFERENCES

1. Makino S, Fukuda K, Miyoshi S, et al. Cardiomyocytes can be generated from marrow stromal cells in vitro. *J Clin Invest.* 1999; 103:697–705.
2. Malouf N N, Coleman W B, Grisham J W, et al. Adult-derived stem cells from the liver become myocytes in the heart in vivo. *Am J Pathol.* 2001;158:1929–35.
3. Orlic D, Kajstura J, Chimenti S, et al. Bone marrow cells regenerate infarcted myocardium. *Nature.* 2001;410:701–5.
4. Jackson K A, Majka S M, Wang H, et al. Regeneration of ischemic cardiac muscle and vascular endothelium by adult stem cells. *J Clin Invest.* 2001;107:1395–402.
5. Hakuno D, Fukuda K, Makino S, et al. Bone Marrow-Derived Regenerated Cardiomyocytes (CMG Cells) Express Functional Adrenergic and Muscarinic Receptors. *Circulation.* 2002;105:380–386.
6. Rafii S, Shapiro F, Pettengell R, et al. Human bone marrow microvascular endothelial cells support long-term proliferation and differentiation of myeloid and megakaryocytic progenitors. *Blood.* 1995;86:3353–63.
7. Davis T A, Lee K P. Ex vivo expansion of primitive murine hematopoietic progenitor cells on porcine endothelial cells. *Transplant Proc.* 1997;29:2005.
8. Mohle R, Salemi P, Moore M A, Rafii S. Expression of interleukin-5 by human bone marrow microvascular endothelial cells: implications for the regulation of eosinophilopoiesis in vivo. *Br J Haematol.* 1997;99:732–8.
9. Rafil S, Mohle R, Shapiro F, et al. Regulation of hematopoiesis by microvascular endothelium. *Leuk Lymphoma.* 1997;27:375–86.
10. Yourey P A, Gohari S, Su J L, Alderson R F. Vascular endothelial cell growth factors promote the in vitro development of rat photoreceptor cells. *J Neurosci.* 2000;20: 6781–8.
11. Palmer T D, Willhoite A R, Gage F H. Vascular niche for adult hippocampal neurogenesis. *J Comp Neurol.* 2000; 425:479–94.

12. Wang T, FitzGerald T J, Haregewoin A. Differential expression of nitric oxide synthases in EGF-responsive mouse neural precursor cells. *Cell Tissue Res.* 1999;296: 489–97.
13. Edelberg J M, Tang L, Hattori K, et al. Young Adult Bone Marrow-Derived Endothelial Precursor Cells Restore Aging-Impaired Cardiac Angiogenic Function. *Circ. Res.* 2002;90:e89-e93.
14. Edelberg J M, Aird W C, Wu W, et al. PDGF mediates cardiac microvascular communication. *J Clin Invest.* 1998; 102:837–43.
15. Edelberg J M, Lee S H, Kaur M, et al. Platelet-Derived Growth Factor-AB Limits the Extent of Myocardial Infarction in a Rat Model: Feasibility of Restoring Impaired Angiogenic Capacity in the Aging Heart. *Circulation.* 2002;105:608–613.
16. Weinsaft J W, Edelberg J M. Aging-Associated Changes in Vascular Activity—A Potential Link to Geriatric Cardiovascular Disease. *Amer J Geriatric Cardiology.* 2001; 10:348–354.
17. Edelberg J M, Jacobson J T, Gidseg D S, et al. Enhanced myocyte-based biosensing of the blood-borne signals regulating chronotropy. *J Appl Physiol.* 2002;92:581–5.
18. Christini D J, Walden J, Edelberg J M. Direct biologically-based biosensing of dynamic physiological Function. *Amer J Physiol.* 2001;280:H2006–2010.
19. Betsholtz C. Role of platelet-derived growth factors in mouse development. *Int J Dev Biol.* 1995;39:817–25.
20. Ataliotis P, Mercola M. Distribution and functions of platelet-derived growth factors and their receptors during embryogenesis. *Int Rev Cytol.* 1997;172:95–127.

All publications and patents are incorporated by reference herein, as though individually incorporated by reference. The invention is not limited to the exact details shown and described, for it should be understood that many variations and modifications may be made while remaining within the spirit and scope of the invention defined by the claims.

What is claimed:

1. A method for administering platelet derived growth factor to cardiac tissues of a mammal comprising administering to the mammal a therapeutically effective amount of allogeneic or autologous bone marrow-derived PDGF B+ and PDGFRα+ endothelial precursor cells that endogenously express the platelet derived growth factor.

2. A method for treating ischemia in a cardiac tissue of a mammal comprising administering to the mammal a therapeutically effective amount of allogeneic or autologous PDGF B+ and PDGFRα+ bone marrow-derived endothelial precursor cells that endogenously express and bind platelet derived growth factor B and promote formation of cardio myocytes.

* * * * *

UNITED STATES PATENT AND TRADEMARK OFFICE
CERTIFICATE OF CORRECTION

PATENT NO.         : 7,135,171 B2
APPLICATION NO.    : 10/367639
DATED              : November 14, 2006
INVENTOR(S)        : Edelberg et al.

It is certified that error appears in the above-identified patent and that said Letters Patent is hereby corrected as shown below:

On the Title page, in field (75), in "Inventors", in column 1, lines 1-5, after "Jay Edelberg, New York, NY (US)" delete "; Shahin Rafii, Great Neck, NY (US); Mun Hong, New York, NY (US); Robert P. Lanza, Clinton, MA (US); Michael D. West, Southborough, MA (US)".

On the Title page, in field (56), under "Other Publications", in column 2, line 10, delete "Gowth Factos" and insert -- Growth Factors --, therefor.

On the Title page, in field (56), under "Other Publications", in column 2, line 32, delete "Facto-AB" and insert -- Factor-AB --, therefor.

In column 80, line 3, in Claim 2, after "express" delete "and bind".

Signed and Sealed this

Twenty-seventh Day of February, 2007

JON W. DUDAS
*Director of the United States Patent and Trademark Office*